United States Patent
Jin et al.

(10) Patent No.: US 10,079,348 B2
(45) Date of Patent: Sep. 18, 2018

(54) MATERIAL FOR ORGANIC ELECTROLUMINESCENT DEVICE AND ORGANIC ELECTROLUMINESCENT DEVICE COMPRISING SAME

(71) Applicant: SAMSUNG DISPLAY CO., LTD., Yongin-si, Gyeonggi-do (KR)

(72) Inventors: Xiulan Jin, Yokohama (JP); Hiroaki Itoi, Yokohama (JP); Junta Fuchiwaki, Yokohama (JP); Asami Sakamoto, Yokohama (JP); Hideo Miyake, Yokohama (JP); Ichiro Imada, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 124 days.

(21) Appl. No.: 15/073,549

(22) Filed: Mar. 17, 2016

(65) Prior Publication Data

US 2017/0012204 A1 Jan. 12, 2017

(30) Foreign Application Priority Data

Jul. 8, 2015 (JP) .................................. 2015-136619

(51) Int. Cl.
*H01L 51/00* (2006.01)
*C07D 307/91* (2006.01)
(Continued)

(52) U.S. Cl.
CPC ........ *H01L 51/0072* (2013.01); *C07D 209/88* (2013.01); *C07D 307/91* (2013.01);
(Continued)

(58) Field of Classification Search
None
See application file for complete search history.

(56) References Cited

U.S. PATENT DOCUMENTS

| 8,980,442 | B2 * | 3/2015 | Yabunouchi | .......... C07C 211/61 257/40 |
| 2003/0147845 | A1 * | 8/2003 | Saavedra | .............. C07C 291/08 424/78.26 |
| 2010/0219404 | A1 * | 9/2010 | Endo | ..................... H01L 51/006 257/40 |

(Continued)

FOREIGN PATENT DOCUMENTS

| JP | 2009-29726 A | 2/2009 |
| JP | 2009-267255 A | 11/2009 |

(Continued)

*Primary Examiner* — Robert S Loewe
(74) *Attorney, Agent, or Firm* — Lewis Roca Rothgerber Christie LLP

(57) ABSTRACT

A material for an organic electroluminescent device having high emission efficiency is represented by following Formula 1:

Formula 1

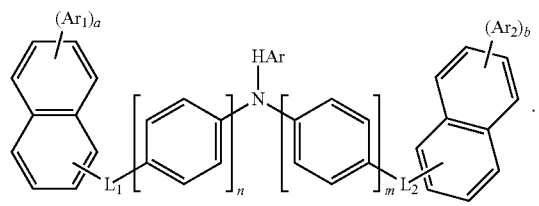

(1)

The material represented by Formula 1 may be included in at least one layer selected from a plurality of layers between an anode and an emission layer of an organic EL device.

10 Claims, 2 Drawing Sheets

(51) Int. Cl.
*C07D 209/88* (2006.01)
*H01L 51/50* (2006.01)
(52) U.S. Cl.
CPC ...... *H01L 51/0058* (2013.01); *H01L 51/0061* (2013.01); *H01L 51/0073* (2013.01); *H01L 51/5056* (2013.01)

(56) References Cited

U.S. PATENT DOCUMENTS

| | | | | |
|---|---|---|---|---|
| 2011/0215308 A1* | 9/2011 | Im | ......................... | H01L 51/006 257/40 |
| 2012/0074395 A1* | 3/2012 | Yabunouchi | .......... | C07C 211/54 257/40 |
| 2012/0119197 A1* | 5/2012 | Nishimura | ........... | C07D 209/86 257/40 |
| 2012/0319091 A1* | 12/2012 | Kato | ................... | C07D 307/91 257/40 |
| 2013/0299806 A1* | 11/2013 | Kato | .................... | H01L 51/006 257/40 |
| 2014/0319472 A1 | 10/2014 | Cho et al. | | |
| 2015/0025207 A1* | 1/2015 | Canich | ................. | C08F 110/06 526/126 |

FOREIGN PATENT DOCUMENTS

| | | |
|---|---|---|
| JP | 2013-65867 A | 4/2013 |
| KR | 10-2013-0024521 A | 3/2013 |
| WO | WO 2010/050778 A1 | 5/2010 |
| WO | WO 2010/061824 A1 | 6/2010 |
| WO | WO 2010114017 A1 * 10/2010 ........... C07C 211/54 |
| WO | WO 2011/021520 A1 | 2/2011 |

* cited by examiner

MATERIAL FOR ORGANIC ELECTROLUMINESCENT DEVICE AND ORGANIC ELECTROLUMINESCENT DEVICE COMPRISING SAME

CROSS-REFERENCE TO RELATED APPLICATION

This U.S. non-provisional patent application claims priority to and the benefit of Japanese Patent Application No. 2015-136619, filed on Jul. 8, 2015, the entire content of which is hereby incorporated by reference.

BACKGROUND

1. Field

One or more aspects of embodiments of the present disclosure herein relate to a material for an organic electroluminescent device and an organic electroluminescent device including the same. One or more aspects of embodiments of the present disclosure relate to a hole transport material for an organic electroluminescent device having high emitting efficiency and long life expectancy.

2. Description of the Related Art

In recent years, organic electroluminescent (EL) displays (that are image displays) have been actively developed. Unlike liquid crystal displays and/or the like, organic EL displays are self-luminescent displays, which display images by recombining holes and electrons (respectively injected from an anode and a cathode) in an emission layer, and emitting light from a luminescent material in the emission layer, wherein the luminescent material includes an organic compound.

An example organic EL device may include an anode, a hole transport layer disposed (e.g., positioned) on the anode, an emission layer disposed on the hole transport layer, an electron transport layer disposed on the emission layer, and a cathode disposed on the electron transport layer. Holes injected from the anode travel via the hole transport layer into the emission layer. Meanwhile, electrons injected from the cathode travel via the electron transport layer into the emission layer. The holes and the electrons injected into the emission layer recombine to generate excitons within the emission layer. The organic EL device can emit light generated by deactivation radiation of the excitons. However, organic EL devices are not limited to the above-described configuration, and may be embodied in various forms.

When the organic devices are applied in displays, organic EL devices having high efficiency are desired. However, in the blue light-emitting region of the organic EL device, it may be difficult to ascertain whether the driving voltage is suitably high and emission efficiency is sufficient, with respect to those in the green light- and red light-emitting regions. To achieve high efficiency of the organic EL device, normalization, stabilization of the hole transport layer, and enhancement of durability are desired.

As a hole transport material used in the hole transport layer, various compounds such as, for example, aromatic amine-based compounds have been disclosed, however, these compounds may result in insufficient emission efficiency and life expectancy of the device. For example, amine derivatives having substituent aryl group or heteroaryl group may be advantageous for extension of life expectancy of an organic EL device. However, the organic EL device employing these materials may nevertheless lack the sufficient emission efficiency and life expectancy. Thus, an organic EL device having improved life expectancy is desired. This is especially true if the emission efficiency of the organic EL device in the blue light-emitting region is low with respect to the red light- and green light-emitting regions.

SUMMARY

One or more aspects of embodiments of the present disclosure are directed toward a material for an organic electroluminescent (EL) device having high emission efficiency, and an organic EL device including the material.

In some embodiments of the present disclosure, a material for an organic EL device having high emission efficiency and long life expectancy in a green to blue light-emitting region of an organic EL device may be used (e.g., may be included) in at least one layer disposed between an emission layer and an anode.

An embodiment of the present inventive concept provides a material for an organic EL device, represented by following Formula 1:

Formula 1

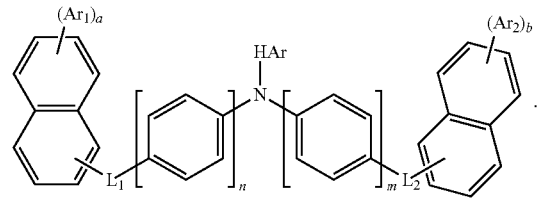

In Formula 1, $Ar_1$ and $Ar_2$ may each independently be selected from a substituted or unsubstituted alkyl group having a carbon atom number of 1 to 30, a substituted or unsubstituted aryl group having a carbon atom number of 6 to 30, a substituted or unsubstituted heteroaryl group having a carbon atom number of 5 to 30, a silyl group, a halogen atom, deuterium, and hydrogen; $L_1$ and $L_2$ may each independently be a single bond or an unsubstituted arylene group having 6 to 30 ring-forming carbon atoms; a and b may be each independently an integer selected from 0 to 4, provided that a sum of a and b is greater than or equal to 1 ($a+b \geq 1$); n and m may be each independently 1 or 2; and HAr may be represented by Formula 2:

Formula 2

HAr = 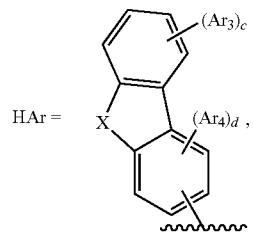

wherein, in Formula 2, X may be selected from $CR_1R_2$, $NAr_5$, O, and S; $Ar_3$ to $Ar_4$ may each independently be selected from a substituted or unsubstituted alkyl group having a carbon atom number of 1 to 30, a substituted or unsubstituted aryl group having a carbon atom number of 6 to 30, a substituted or unsubstituted heteroaryl group having a carbon atom number of 5 to 30, a silyl group, a halogen atom, deuterium, and hydrogen; $Ar_5$ may be selected from a substituted or unsubstituted alkyl group having a carbon atom number of 1 to 30, a substituted or unsubstituted aryl group having a carbon atom number of 6 to 30, a substituted or unsubstituted heteroaryl group having a carbon atom number of 5 to 30; $R_1$ and $R_2$ may be each independently selected from a substituted or unsubstituted aryl group having a carbon atom number of 6 to 30, a substituted or unsubstituted alkyl group having a carbon atom number of 1 to 30, a silyl group, a halogen atom, deuterium, and hydrogen; c may be an integer selected from 0 to 4; and d may be an integer selected from 0 to 3.

In an embodiment of the inventive concept, the material for an organic EL device may enhance emission efficiency and life expectancy of the organic EL device by including an amine moiety having a heteroaryl group.

In an embodiment of the inventive concept, HAr may be a substituted or unsubstituted heteroaryl group having 6 to 30 ring-forming carbon atoms.

In an embodiment of the inventive concept, the material for an organic EL device may enhance emission efficiency and life expectancy of the organic EL device by including an amine moiety having a heteroaryl group.

In an embodiment, $Ar_1$ and $Ar_2$ may each be hydrogen.

In an embodiment of the inventive concept, the material for an organic EL device may enhance emission efficiency and life expectancy of the organic EL device by including an amine moiety having a heteroaryl group.

In an embodiment, $Ar_3$ and $Ar_4$ may each be hydrogen, and Ary may be a phenyl group or a naphthyl group.

In an embodiment of the inventive concept, the material for an organic EL device may enhance emission efficiency and life expectancy of the organic EL device by including an amine moiety having a heteroaryl group.

In an embodiment of the inventive concept, the material for an organic EL device may be included in at least one layer of an organic EL device.

In an embodiment of the inventive concept, an organic EL device may include an anode, an emission layer, and a plurality of layers between the anode and the emission layer, and the material for an organic EL device may be included in at least one layer selected from the plurality of layers between the emission layer and the anode of the organic EL device.

In an embodiment of the inventive concept, the organic EL device may achieve extension of life expectancy by including the material for an organic EL device in at least one layer disposed between an emission layer and anode.

BRIEF DESCRIPTION OF THE DRAWINGS

The accompanying drawings are included to provide a further understanding of the present inventive concept, and are incorporated in and constitute a part of this specification. The drawings illustrate example embodiments of the inventive concept and, together with the description, serve to explain principles of the inventive concept. In the drawings.

DETAILED DESCRIPTION

Figure 1:
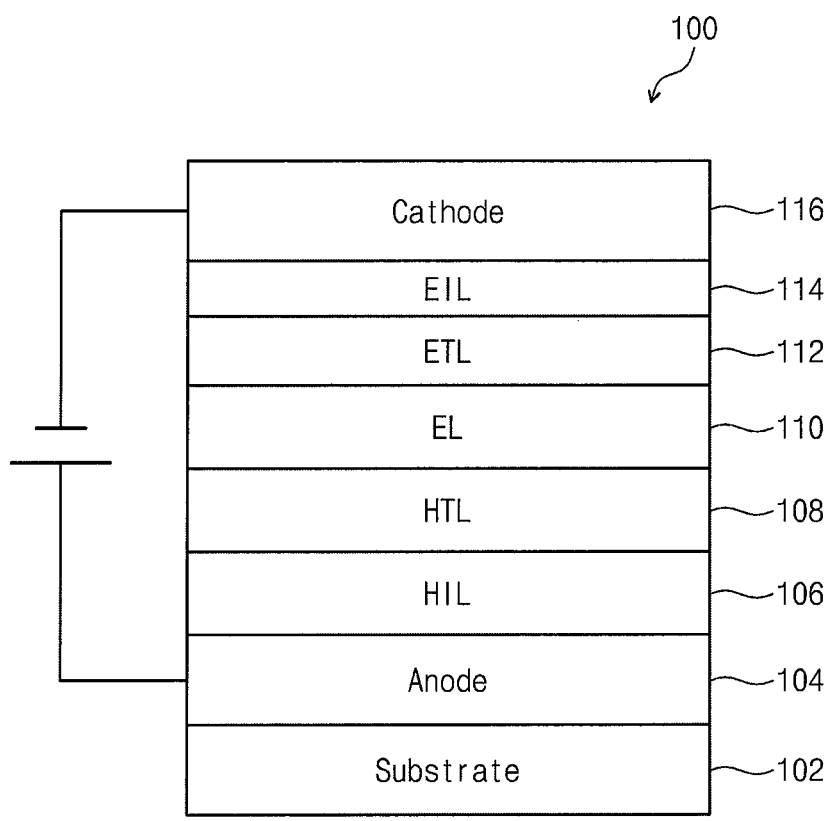
FIG. 1 is a schematic diagram showing an organic electroluminescent (EL) device 100 according to an embodiment of the inventive concept.

Example embodiments of the inventive concept will be described below in more detail with reference to the accompanying drawings. The inventive concept may, however, be embodied in different forms and should not be construed as limited to the embodiments set forth herein. Rather, these embodiments are provided for illustrative purposes only, and to explain the scope of the inventive concept to those skilled in the art.

In an organic electroluminescent (EL) device, low driving voltage may be achieved by introducing a material in which an amine moiety includes a heteroaryl group and has high planarity, thus resulting in a relatively high (or suitable) carrier resistance. In addition, a material in which an amine moiety includes a heteroaryl group having relatively high hole transportability may achieve high efficiency.

Hereinafter, a material for an organic EL device according to an embodiment of the inventive concept and an organic EL device including the material will be described with reference to drawings. The material for an organic EL device of an embodiment of the inventive concept, and the organic EL device including the material may, however, be embodied in many different forms and should not be construed as limited to the description in the embodiments set forth herein. In the drawings, same elements (or elements having the same function) are designated by the same reference numerals, and duplicative explanations thereof will not be provided.

A material for an organic EL device according to an embodiment of the inventive concept may be an amine compound represented by following Formula 1:

Formula 1

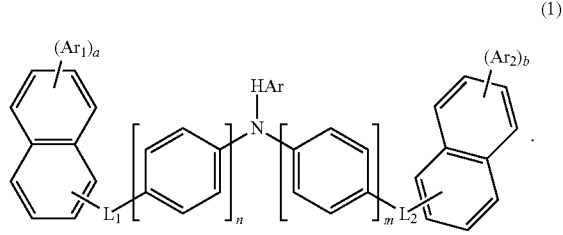

(1)

In Formula 1, $Ar_1$ and $Ar_2$ may each independently be selected from a substituted or unsubstituted alkyl group having a carbon atom number of 1 to 30, a substituted or unsubstituted aryl group having a carbon atom number of 6 to 30, a substituted or unsubstituted heteroaryl group having a carbon atom number of 5 to 30, a silyl group, a halogen atom, deuterium, and hydrogen; $L_1$ and $L_2$ may each independently be a single bond or an unsubstituted arylene group having 6 to 30 ring-forming carbon atoms; a and b may each independently be an integer from 0 to 4, provided that a sum of a and b is greater than or equal to 1 (a+b≥1); and n and m may be each independently 1 or 2; and HAr may be represented by Formula 2:

Formula 2

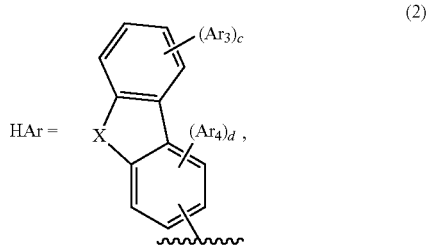

HAr = (structure with X, (Ar₃)$_c$, (Ar₄)$_d$)    (2)

wherein, in Formula 2, X may be selected from $CR_1R_2$, $NAr_5$, O, and S; $Ar_3$ to $Ar_4$ may each independently be selected from a substituted or unsubstituted alkyl group having a carbon atom number of 1 to 30, a substituted or unsubstituted aryl group having a carbon atom number of 6 to 30, a substituted or unsubstituted heteroaryl group having a carbon atom number of 5 to 30, a silyl group, a halogen atom, deuterium, and hydrogen; $Ar_5$ may be selected from a substituted or unsubstituted alkyl group having a carbon atom number of 1 to 30, a substituted or unsubstituted aryl group having a carbon atom number of 6 to 30, a substituted or unsubstituted heteroaryl group having a carbon atom number of 5 to 30; $R_1$ and $R_2$ may be each independently selected from a substituted or unsubstituted aryl group having a carbon atom number of 6 to 30, a substituted or unsubstituted alkyl group having a carbon atom number of 1 to 30, a silyl group, a halogen atom, deuterium, and hydrogen; c may be an integer selected from 0 to 4; and d may be an integer selected from 0 to 3.

As used herein, the expression "a group having a carbon atom number of X" may refer to a group having X carbon atoms.

In some embodiments, HAr may be a substituted or unsubstituted heteroaryl group having 6 to 30 ring-forming carbon atoms.

The heteroaryl group having 6 to 30 ring-forming carbon atoms used in, for example, HAr may be a pyridyl group, a quinolyl group, an isoquinolyl group, a benzofuryl group, a benzothiophenyl group, a benzothienyl group, an indolyl group, a benzoxazolyl group, a benzothiazolyl group, a quinoxalyl group, a benzoimidazolyl group, a dibenzofuryl group, a dibenzothienyl group, a carbazolyl group, etc., but is not limited thereto.

In Formula 1, the alkyl group having a carbon atom number of 1 to 30 used in, for example, $Ar_1$ and $Ar_2$ may be a methyl group, an ethyl group, a propyl group, an isopropyl group, an n-butyl group, an s-butyl group (e.g., sec-butyl group), an isobutyl group, a t-butyl group, an n-pentyl group, an n-hexyl group, an n-heptyl group, an n-octyl group, a hydroxyl methyl group, a 1-hydroxyl ethyl group, a 2-hydroxyl ethyl group, a 2-hydroxyl isobutyl group, a 1,2-dihydroxyl ethyl group, a 1,3-dihydroxyl isopropyl group, a 2,3-dihydroxyl-t-butyl group, a 1,2,3-trihydroxyl propyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc., but is not limited thereto.

In Formula 1, the aryl group having a carbon atom number of 6 to 30 used in, for example, $Ar_1$ and $Ar_2$, may be a phenyl group, a naphthyl group, an anthracenyl group, a phenantolyl group, a biphenyl group, a terphenyl group, a quaterphenyl group, a fluorenyl group, a triphenylenyl group, a biphenylenyl group, a pyrenyl group, a benzofluoranthenyl group, a chrysenyl group, a phenylnaphthyl group, a naphthyl phenyl group, etc., and in some embodiments may be a phenyl group, a naphthyl group, and/or a biphenyl group. However, the aryl group having a carbon atom number of 6 to 30 is not limited to the examples mentioned above.

In addition, the heteroaryl group having a carbon atom number of 5 to 30 used in, for example, $Ar_1$ and $Ar_2$ may be a pyridyl group, a quinolyl group, an isoquinolyl group, a benzofuryl group, a benzothienyl group, an indolyl group, a benzoxazolyl group, a benzothiazolyl group, a quinoxalyl group, a benzoimidazolyl group, a dibenzofuryl group, a dibenzothienyl group, a carbazolyl group, etc., but is not limited thereto.

Additionally, the silyl group used in, for example, $Ar_1$ and $Ar_2$ may be a trialkylsilyl group, a triarylsilyl group, a monoalkyldiarylsilyl group, and/or a dialkylmonoarylsilyl group, and in some embodiments, may be a trimethylsilyl group, a triphenylsilyl group, etc.

Further, the substituent group of $Ar_1$ and/or $Ar_2$ may be a phenyl group, an alkoxy group, and/or an alkyl group having a carbon atom number of 1 to 6. Non-limiting examples of the alkyl group having a carbon atom number of 1 to 6 may include a methyl group, an ethyl group, an n-propyl group, an i-propyl group (e.g., isopropyl group), an n-butyl group, an s-butyl group, a t-butyl group, an n-pentyl group, an n-hexyl group, a c-propyl group (e.g., cyclopropyl group), a c-butyl group (e.g., cyclobutyl group), a c-pentyl group (e.g., cyclopentyl group), a c-hexyl group (e.g., cyclohexyl group), etc. Non-limiting examples of the alkoxy group having a carbon atom number of 1 to 6 may include a methoxy group, an ethoxy group, an n-propoxy group, an i-propoxy group (e.g., isopropoxy group), an n-butoxy group, an s-butoxy group (e.g., sec-butoxy group), a t-butoxy group, an n-pentoxy group, an n-hexoxy group, a c-propoxy group (e.g., cyclopropoxy group), a c-butoxy group (e.g., cyclobutoxy group), a c-pentoxy group (e.g., cyclopentoxy group), a c-hexoxy group (e.g., cyclohexoxy group), etc.

In Formula 1, the arylene group having 6 to 30 ring-forming carbon atoms used in, for example, $L_1$ and $L_2$, may be, but is not limited to, a phenylene group, a biphenylene group, a terphenylene group, a naphthylene group, an anthracenylene group, a fluorenylene group, a triphenylenylene group, a quaterphenylene group, a kink-phenylene group, etc. For example, in Formula 1, the arylene group having 6 to 30 ring-forming carbon atoms used in, for example, $L_1$ and $L_2$ may be an arylene group having 6 to 12 ring-forming carbon atoms, and may include a phenylene group, a biphenylene group, a naphthylene group, etc.

In some embodiments, in Formula 1, $R_1$ and $R_2$ may each independently be selected from a substituted or unsubstituted heteroaryl group having a carbon atom number of 1 to 30, an alkyl group, a silyl group, a halogen atom, deuterium, and hydrogen.

In addition, the halogen atom used in, for example, $R_1$ to $R_2$ may be a fluorine atom (F), a chlorine atom (Cl), and/or a bromine atom (Br).

In Formulae 1 and 2, when $R_1$, $R_2$, and $Ar_1$ to $Ar_5$ each independently have a substituent group, the substituent group may be an alkyl group (such as a methyl group, an ethyl group, a propyl group, a pentyl group, and/or a hexyl group), or an aryl group (such as a phenyl group, a biphenyl group, and/or a naphthyl group). In addition, each of $Ar_1$ to $Ar_5$ may include a plurality of substituent groups. In some embodiments, the substituent groups may be linked to each other to form a saturated or unsaturated ring.

According to embodiments of the inventive concept, when the material for an organic EL device includes the amine compound having a heteroaryl group, conjugation around the amine may be substantially secured, and stability to radical may be enhanced, thereby achieving a relatively high (or suitable) carrier resistance and long life expectancy of the organic EL device.

In addition, the amine compound according to embodiments of the inventive concept may achieve high efficiency due to high hole transportability of the heteroaryl group.

Additionally, when the amine compound includes a substituent group having a relatively high planarity (e.g., a group that is substantially planar) such as a heteroaryl group that includes two benzene rings (e.g., a dibenzothiophene group, a carbazole group, and/or a dibenzofuran group), planarity of the entire compound represented by Formula 1 may be high, and thus packing may be relatively easy, thereby achieving an extremely low driving voltage.

For example, the material for an organic EL device according to an embodiment of the inventive concept may be selected from Compounds 1 to 120 (collectively denoted as Formula 3):

Formula 3

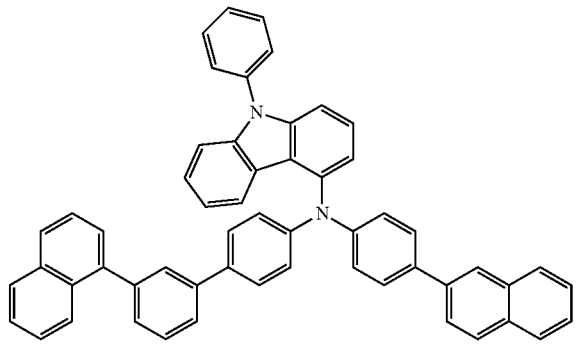

2

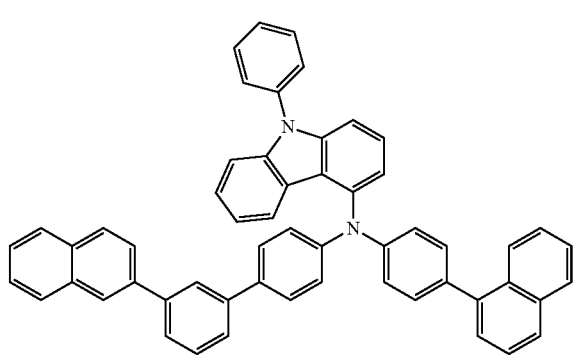

3

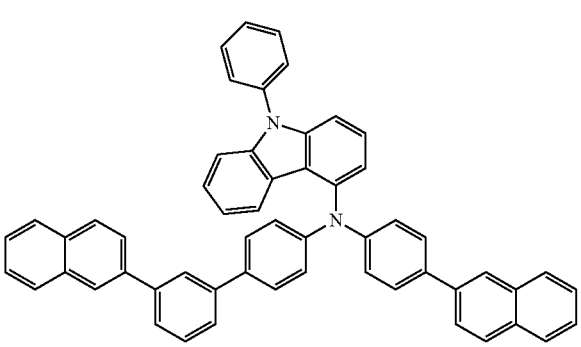

4

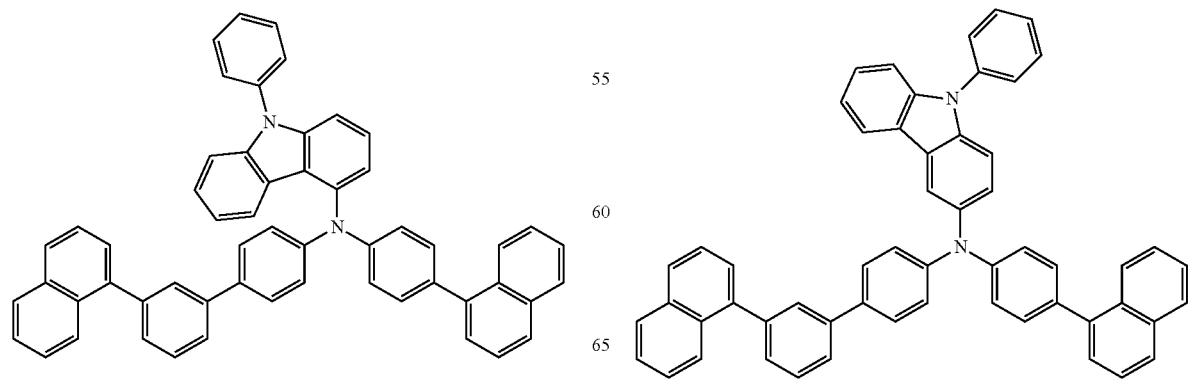

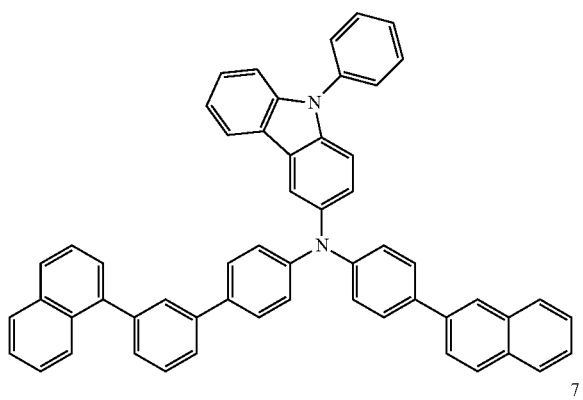
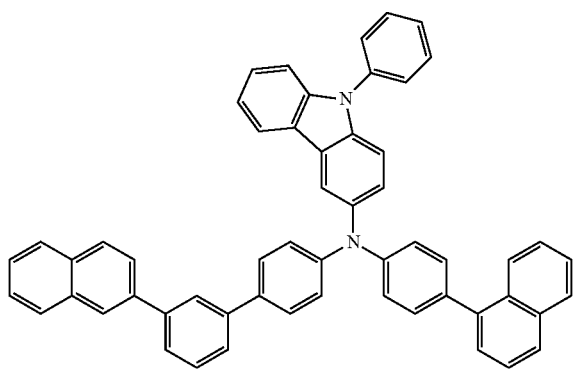
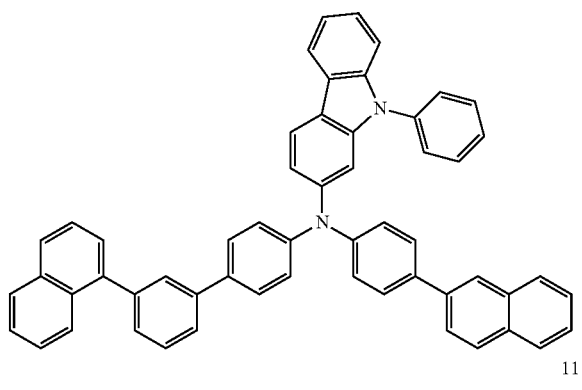

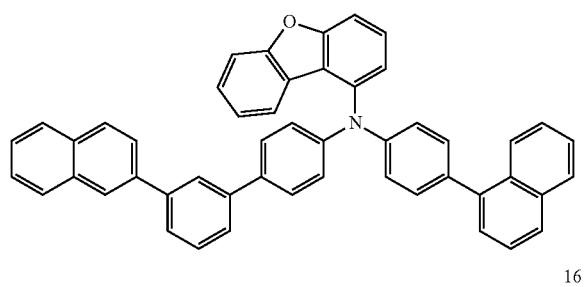
15
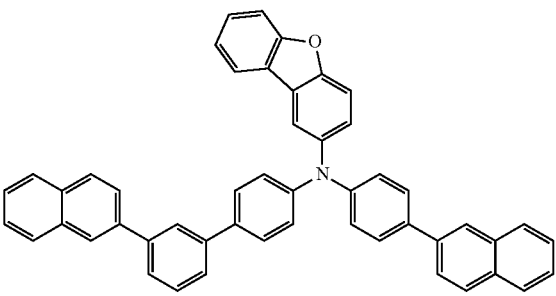
20
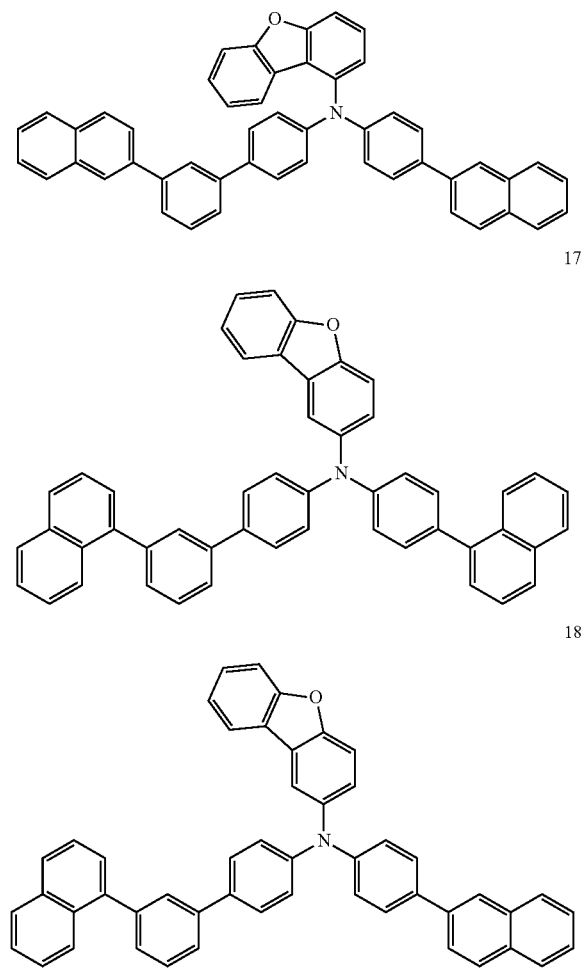
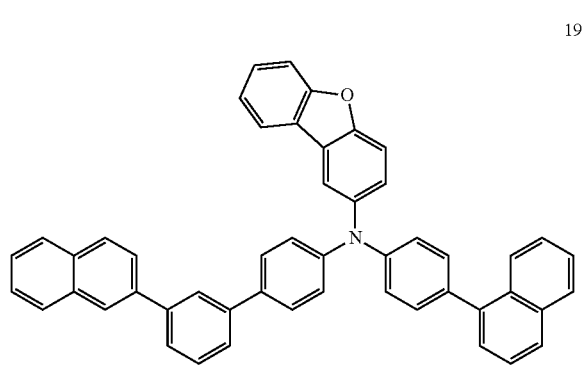
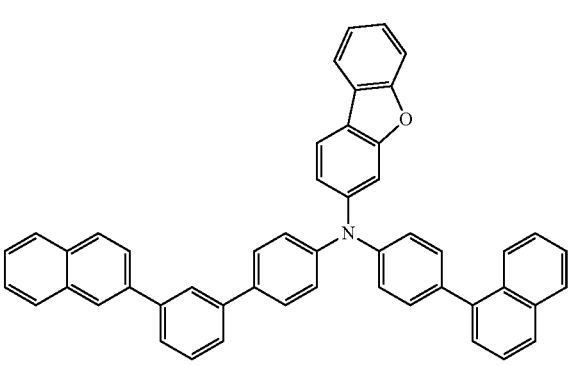

24
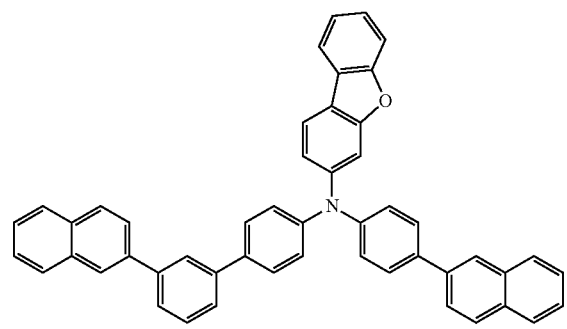
25
29
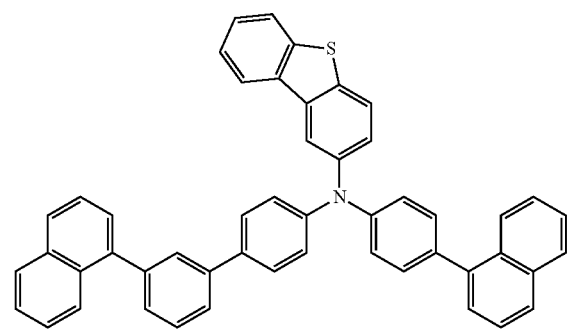
30
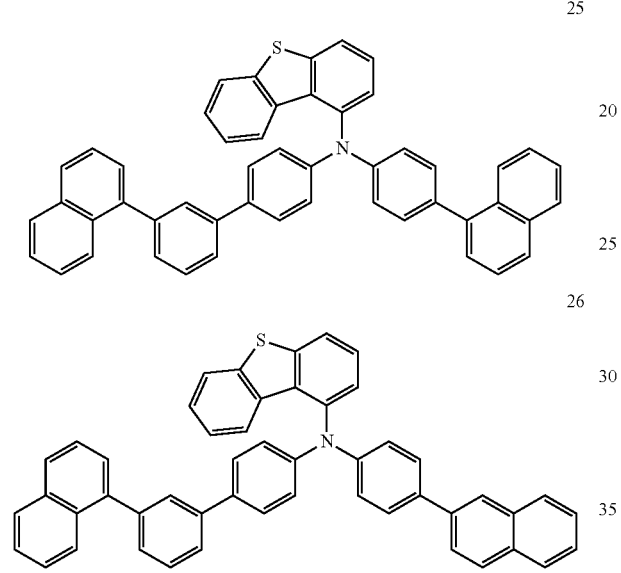
26
27
31
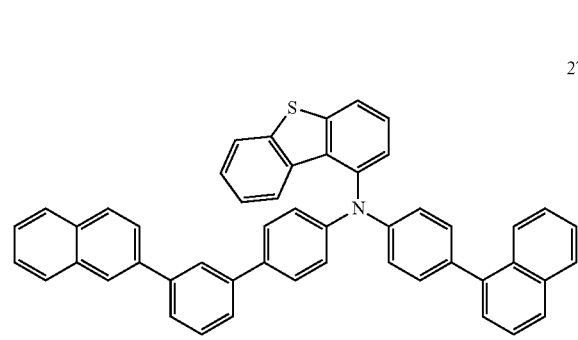
28
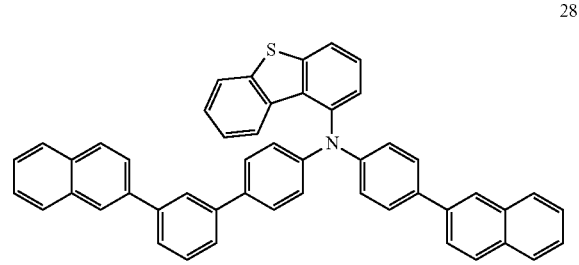
32
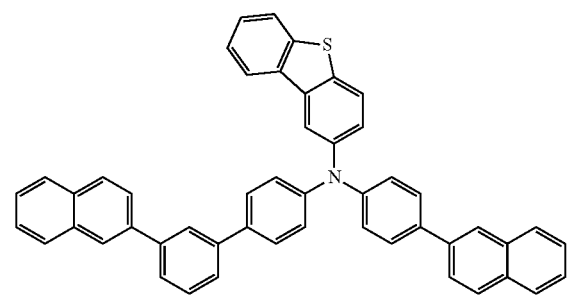

33
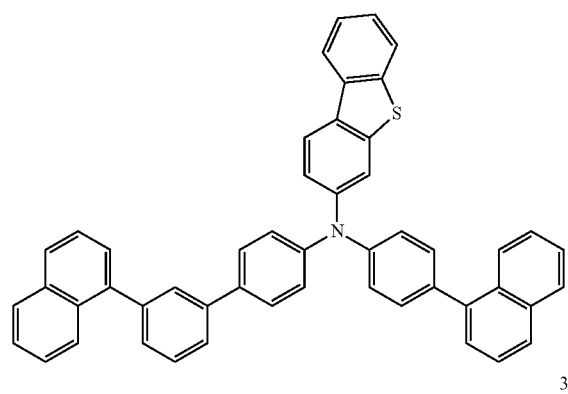
34
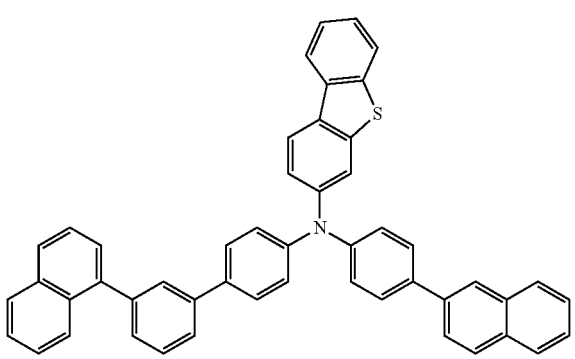
35
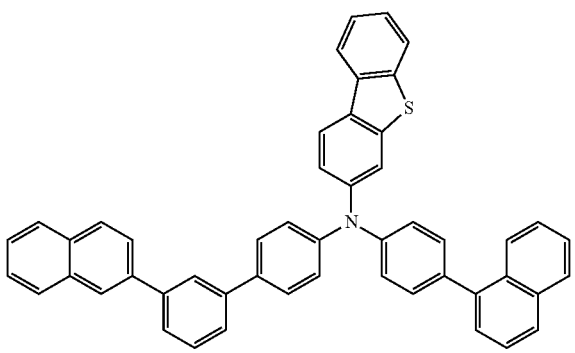
36
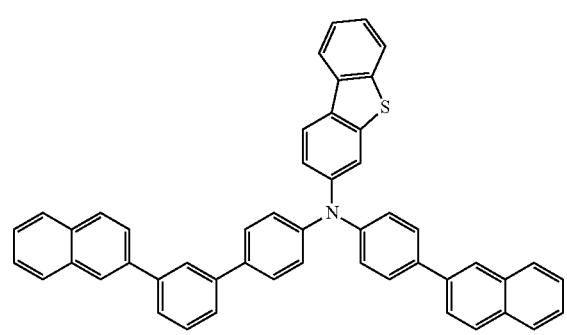
37
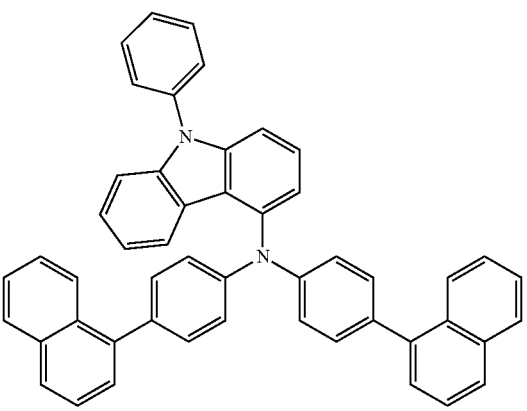
38
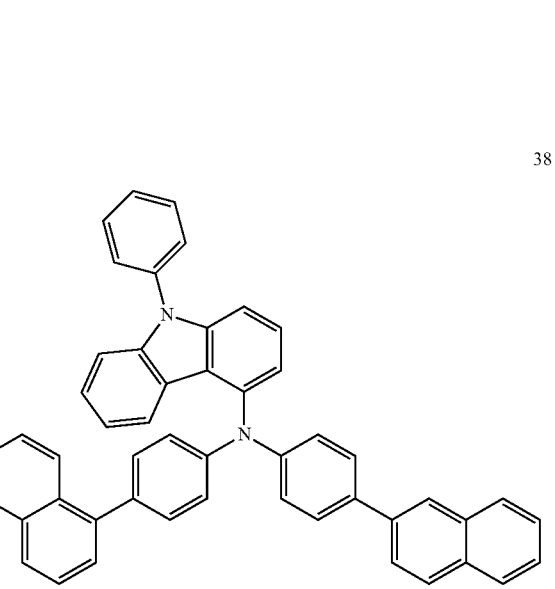
39
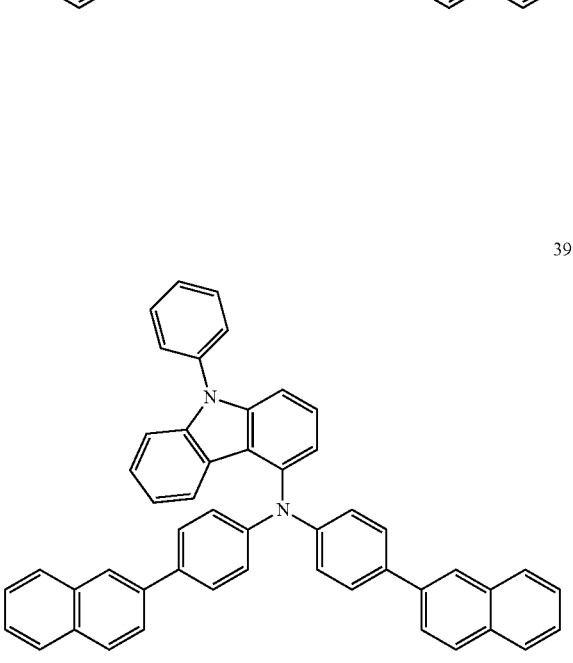

40
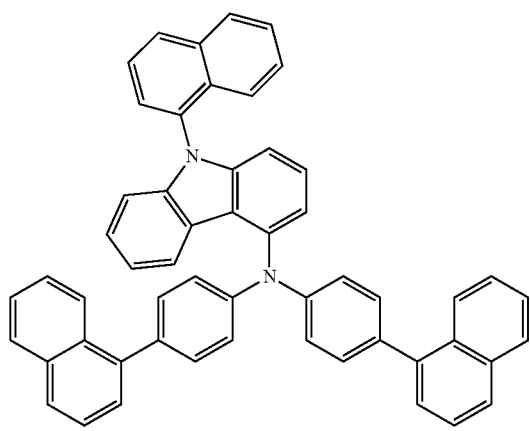
41
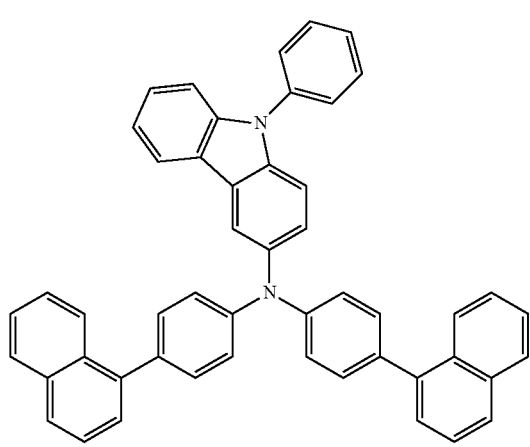
42
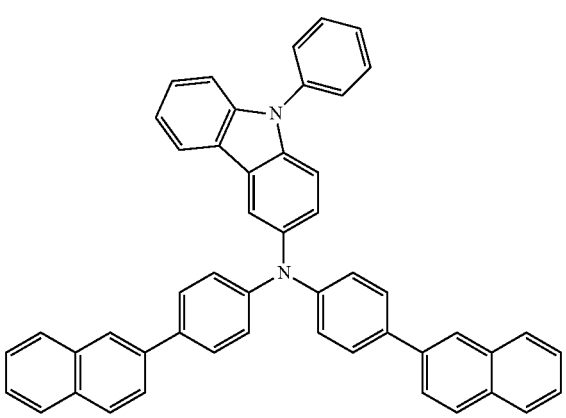
43
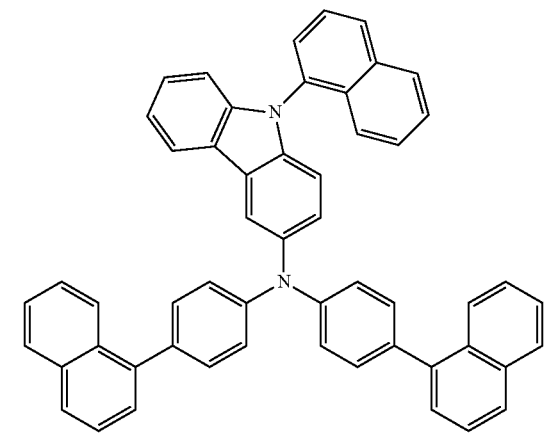
44
45
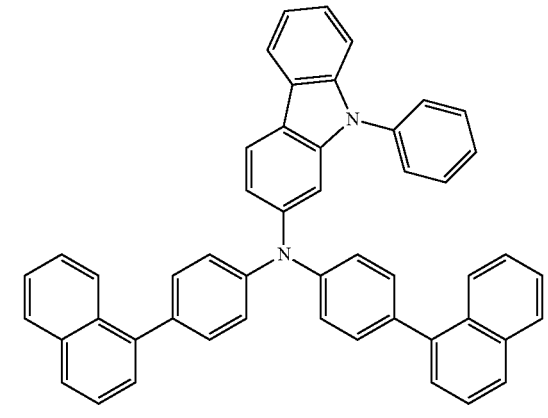

46
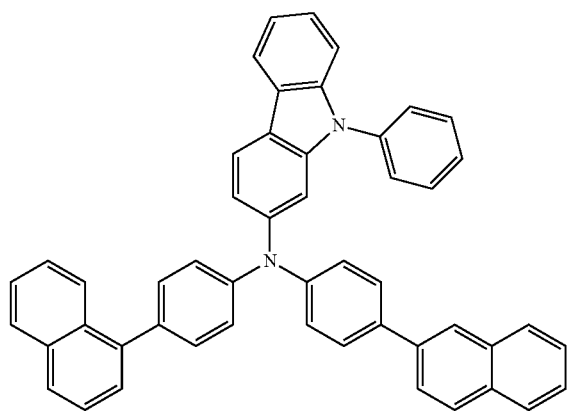
47
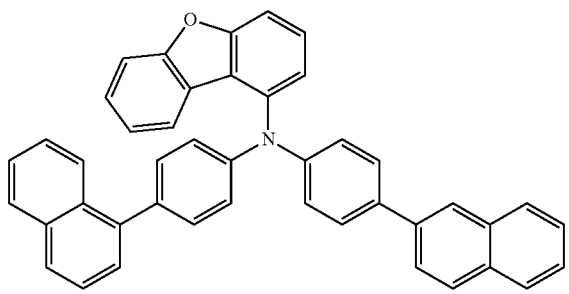
48
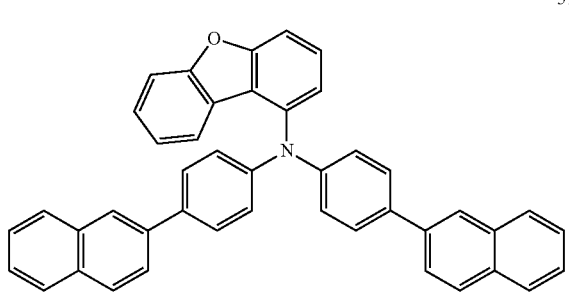
49
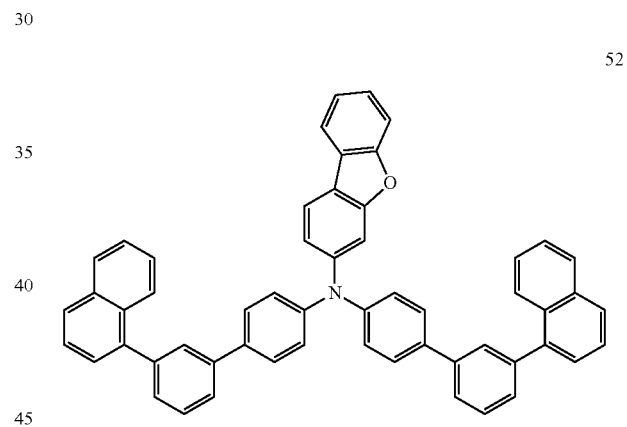
50
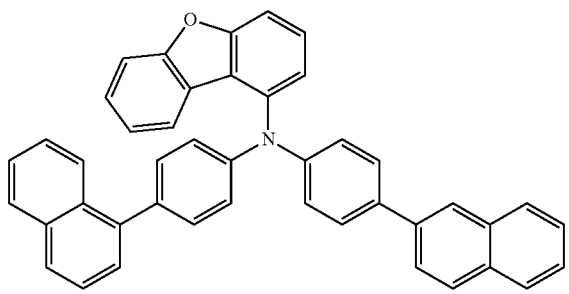
51
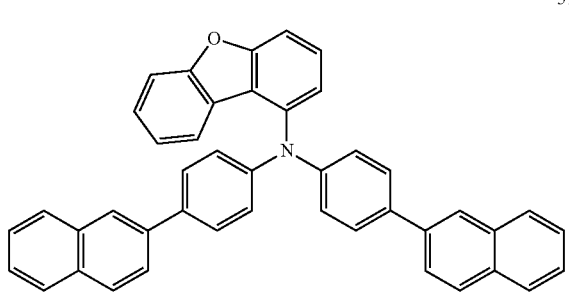
52
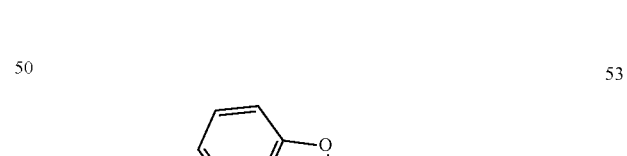
53
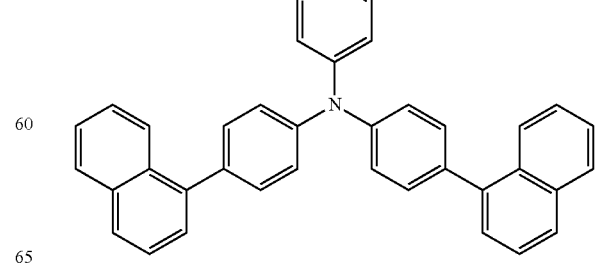

54
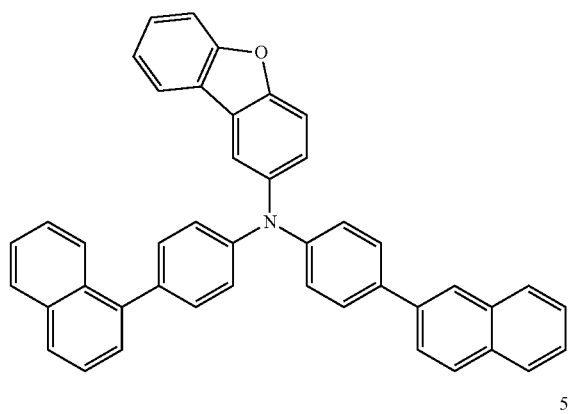
55
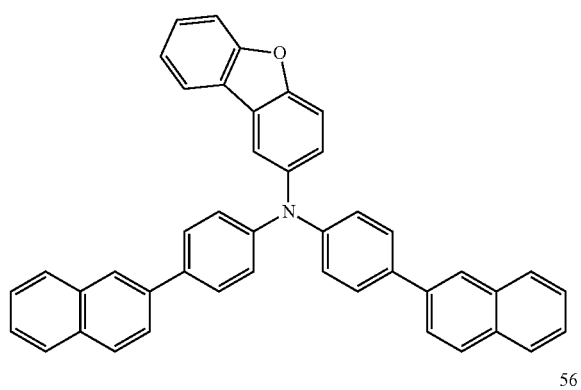
56
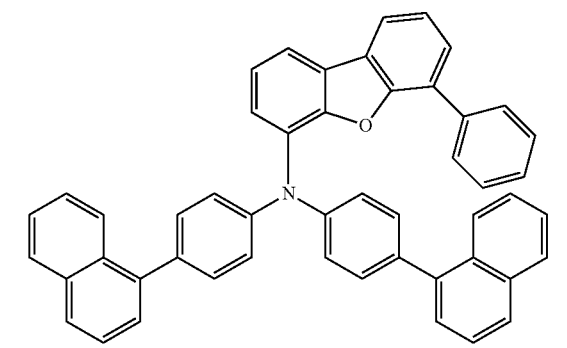
57
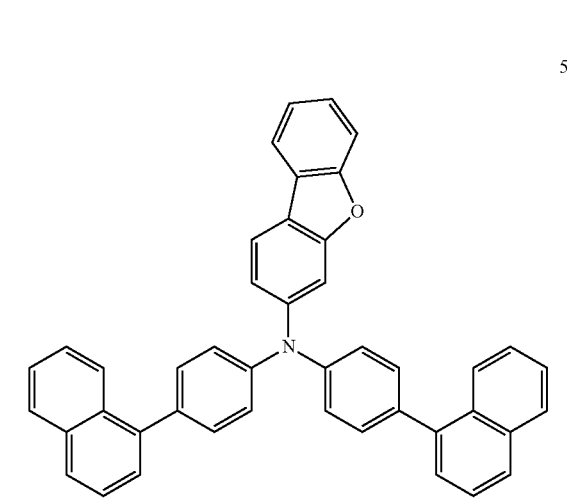
58
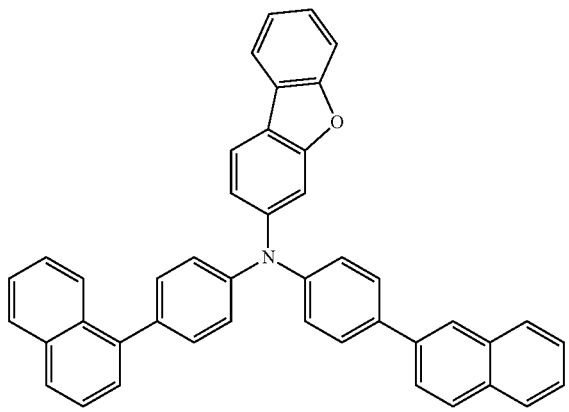
59
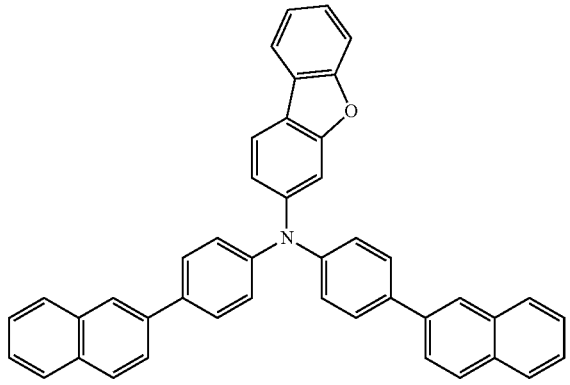
60
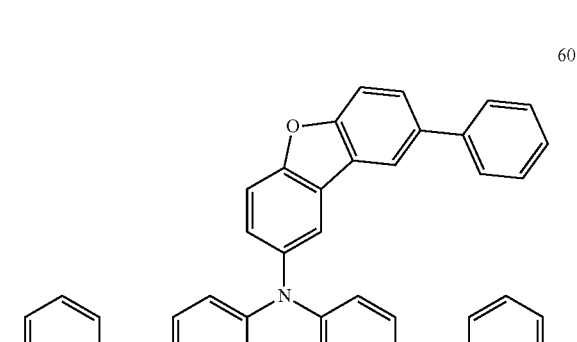
61
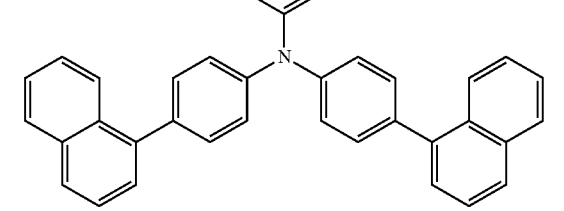

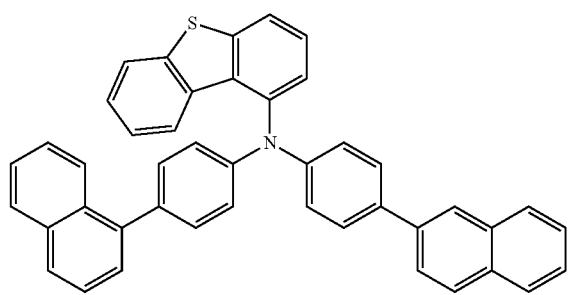
62
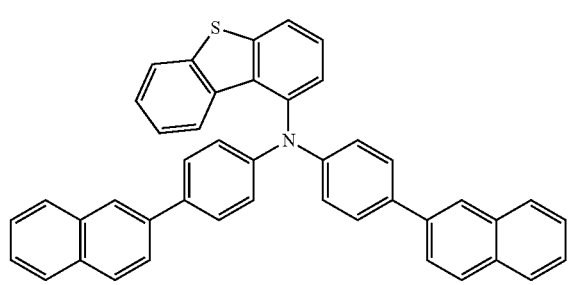
63
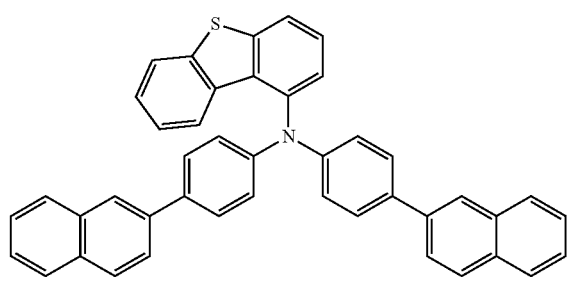
64
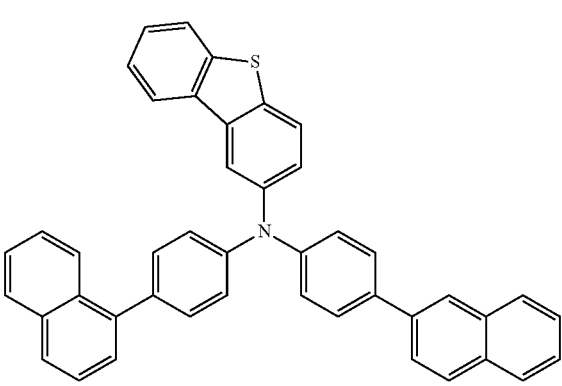
65
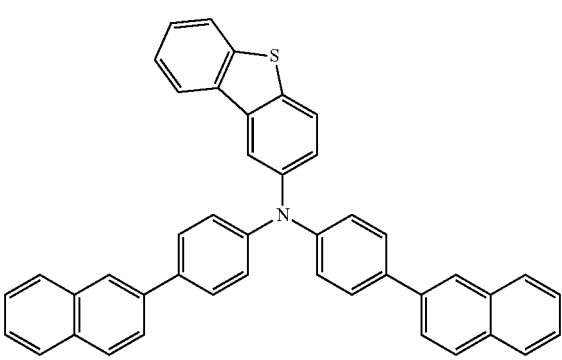
66
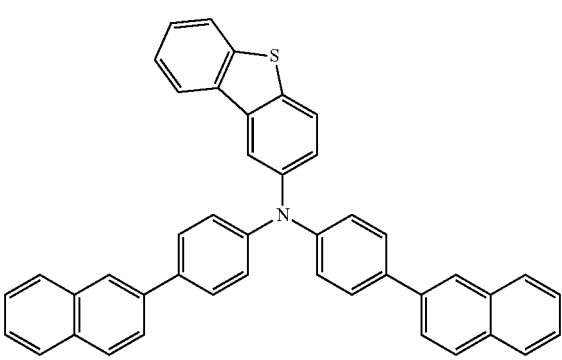
67
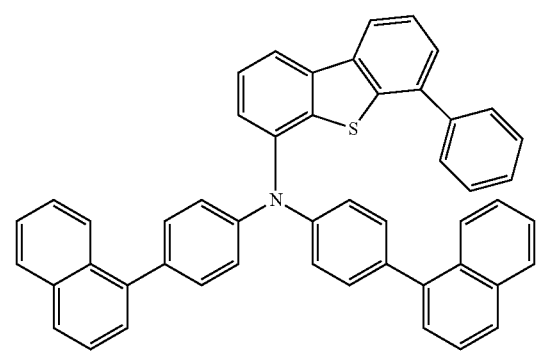
68
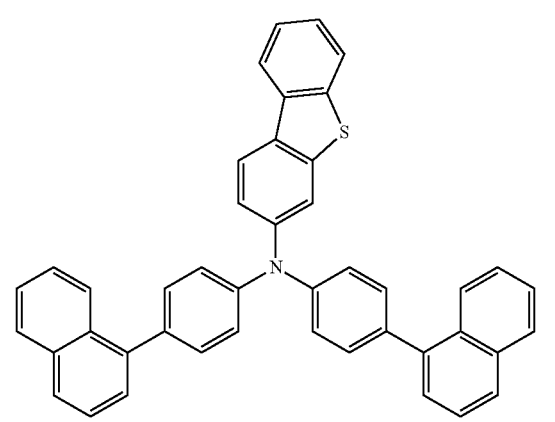
69

70
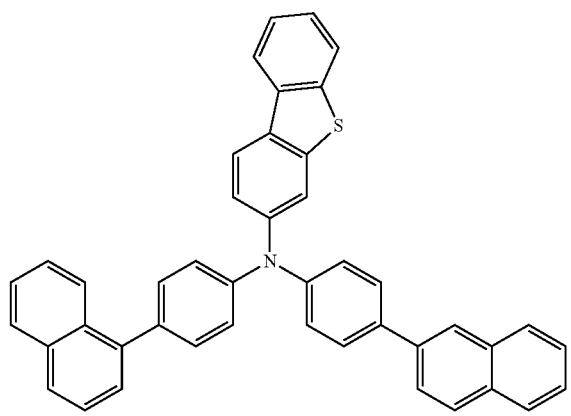
71
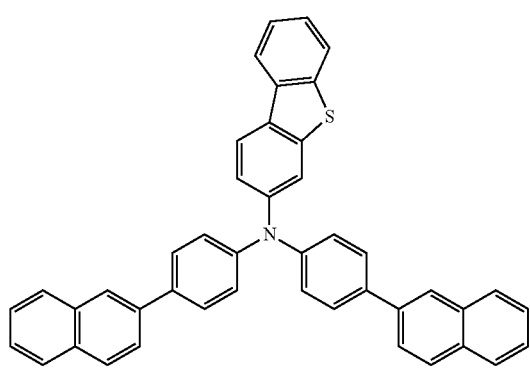
72
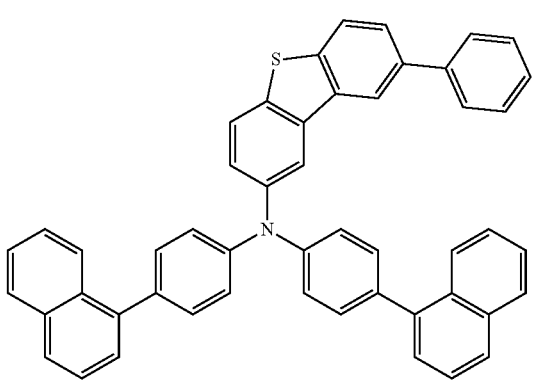
73
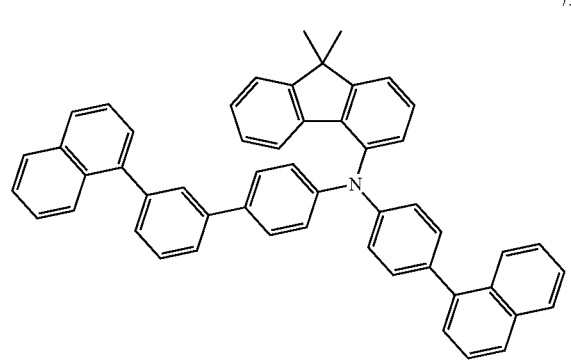
74
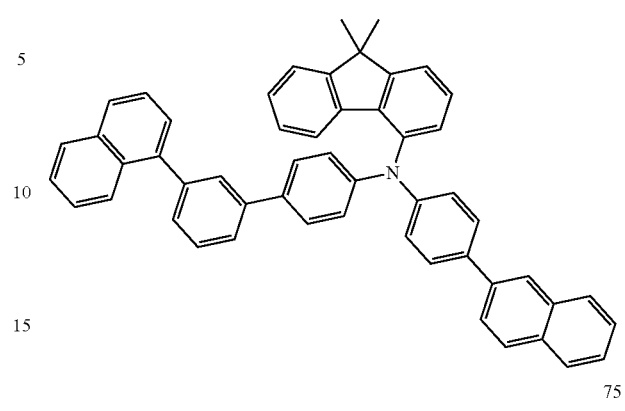
75
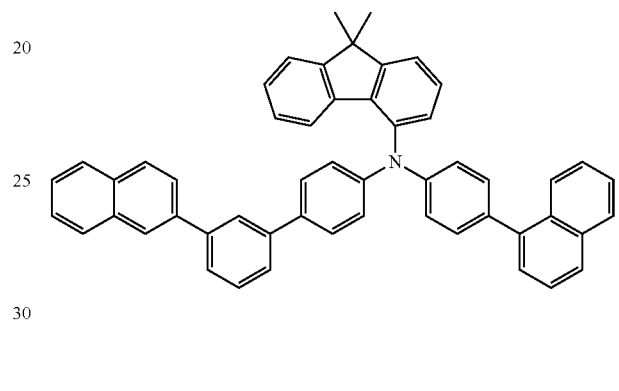
76
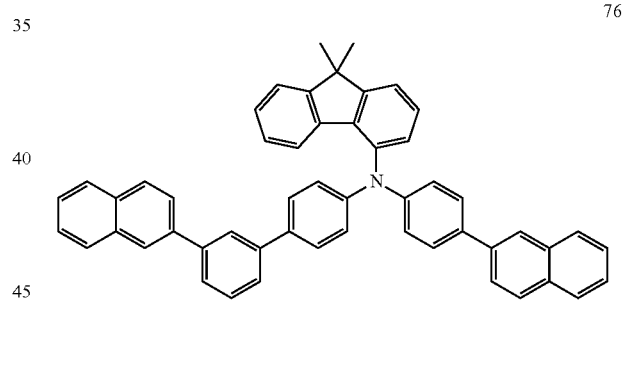
77
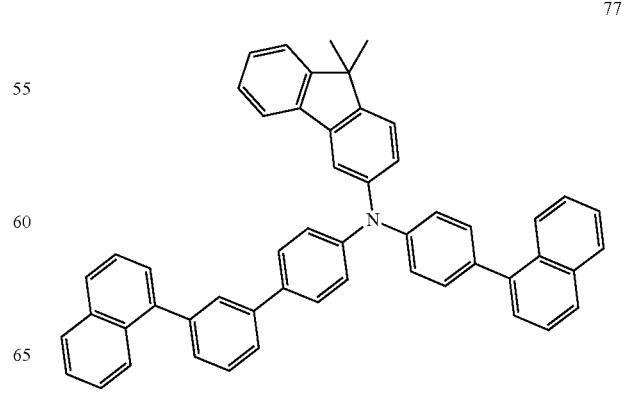

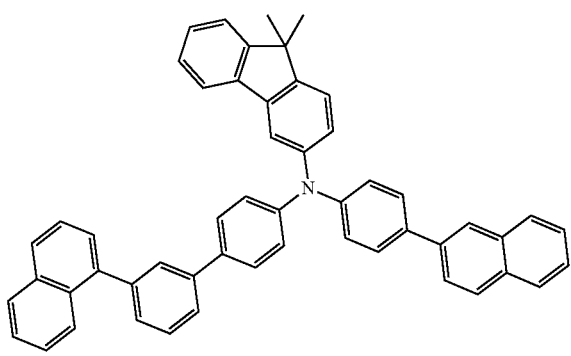
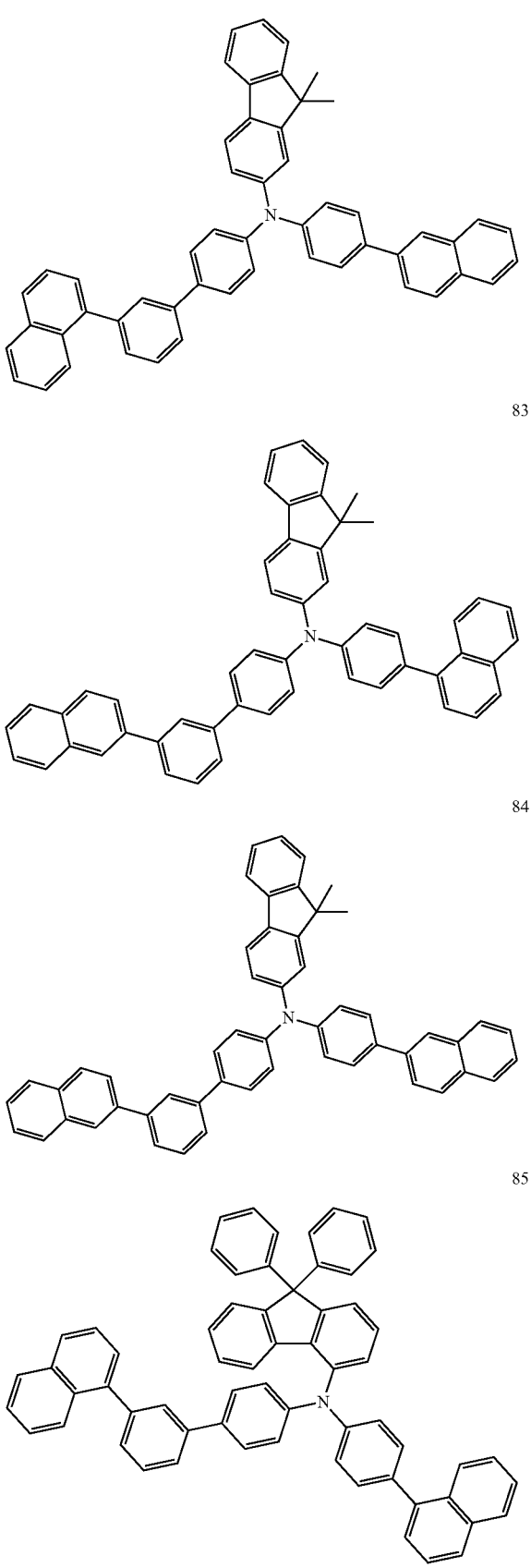

86
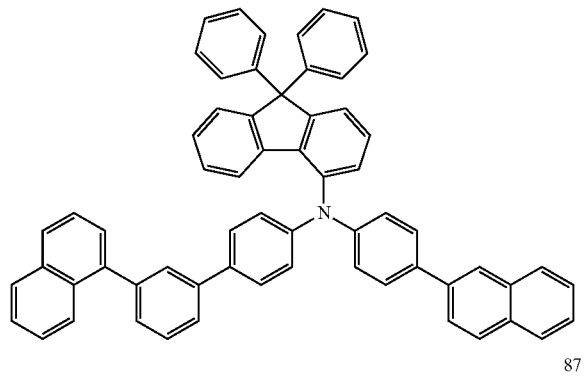
87
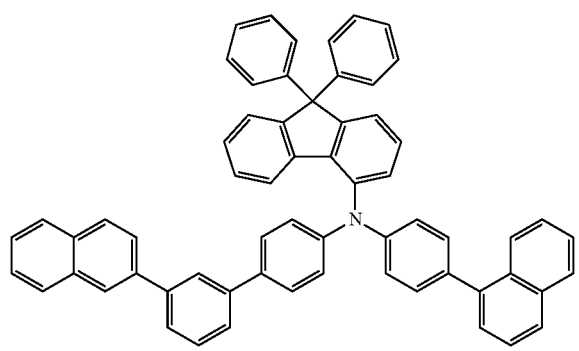
88
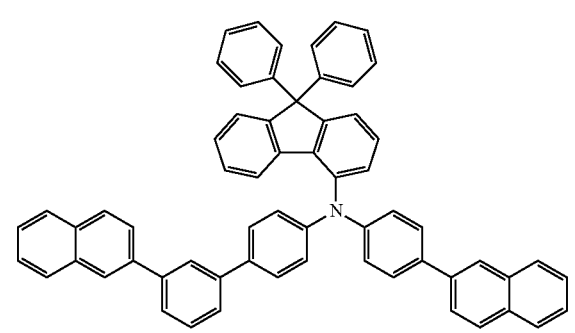
89
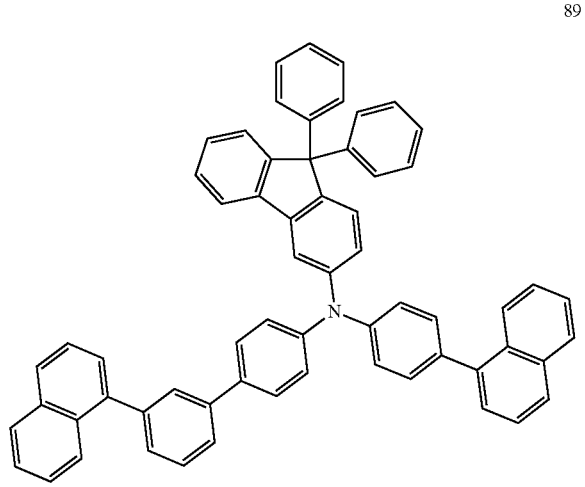
90
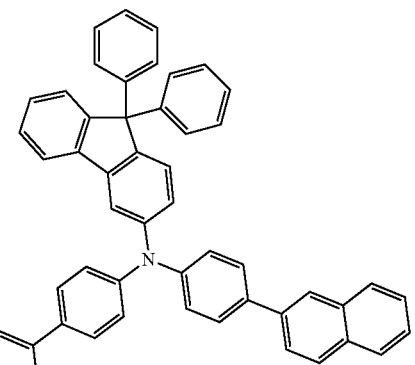
91
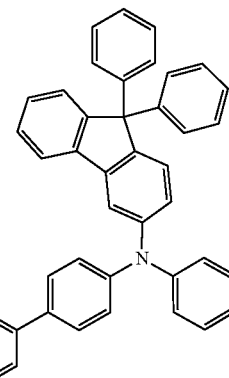
92
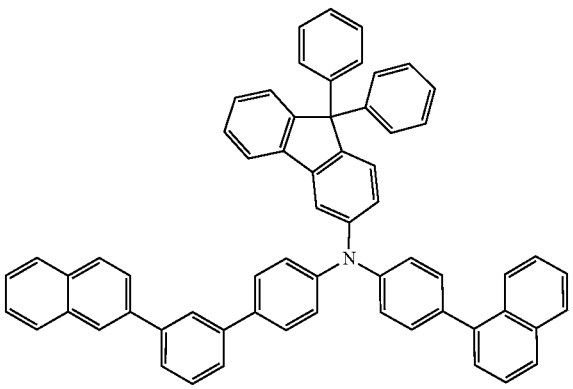
93
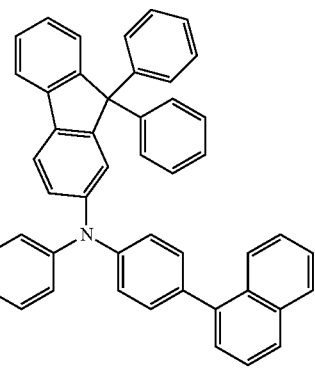

94
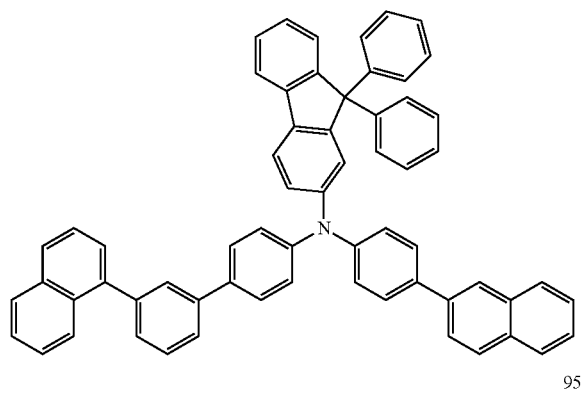
95
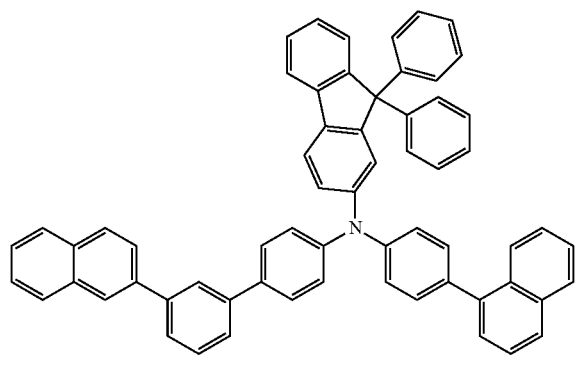
96
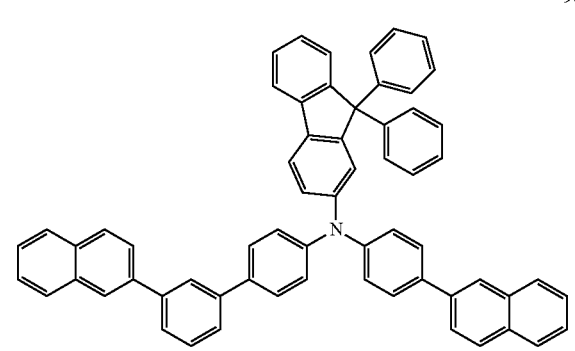
97
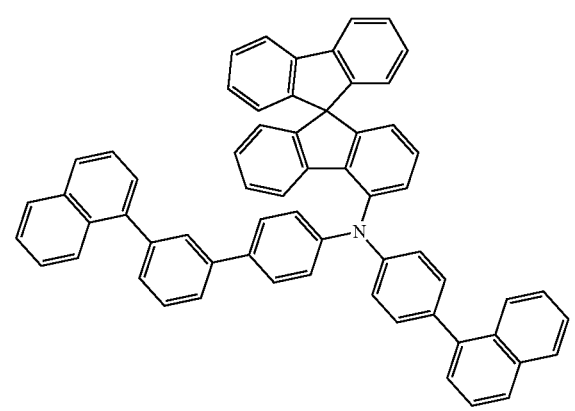
98
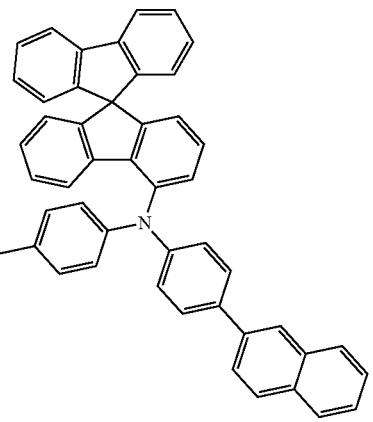
99
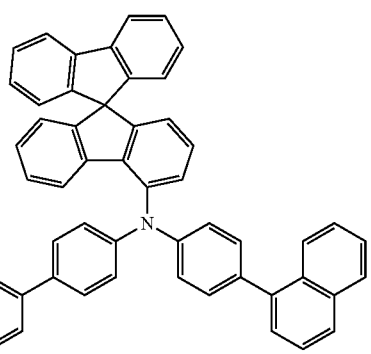
100
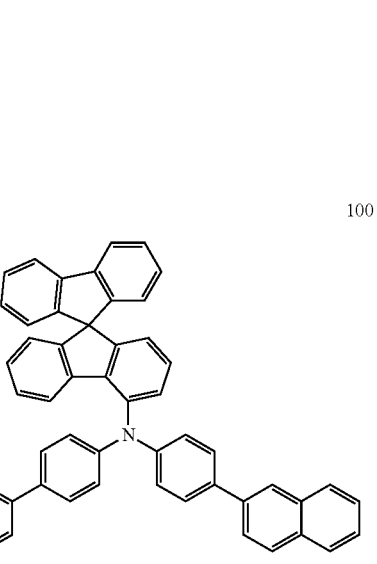

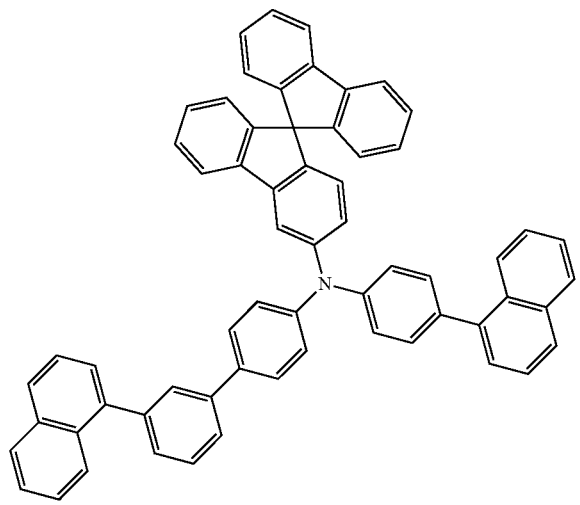
101
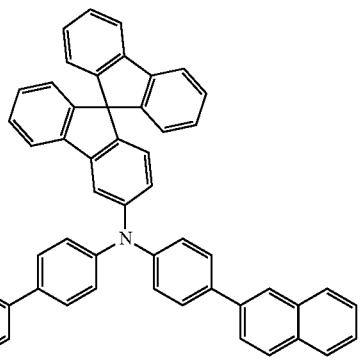
104
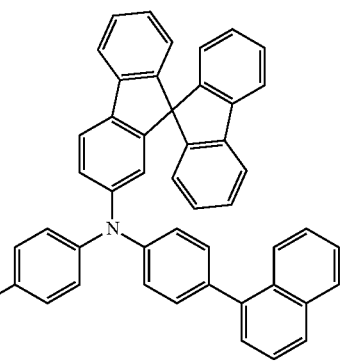
105
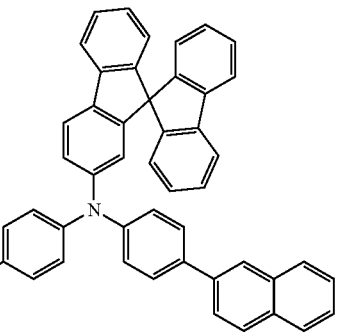
106
102
103
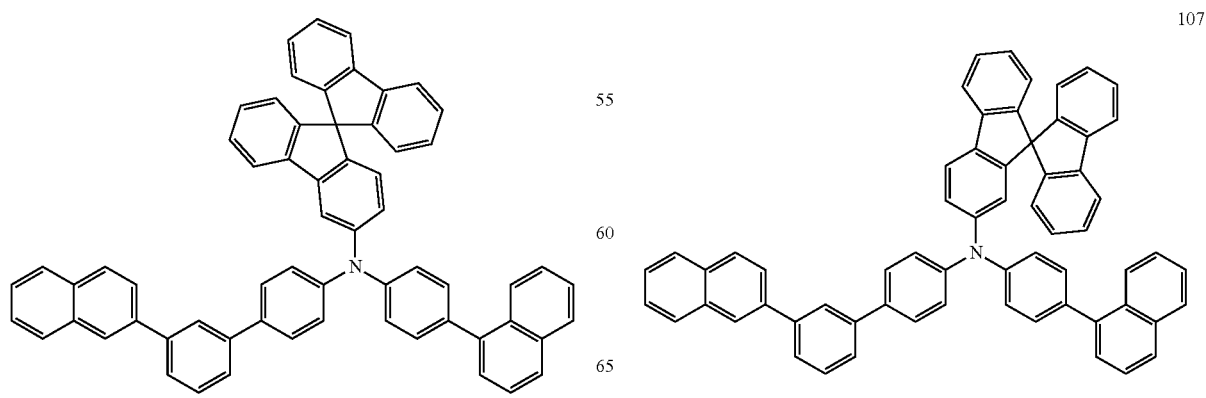
107

108
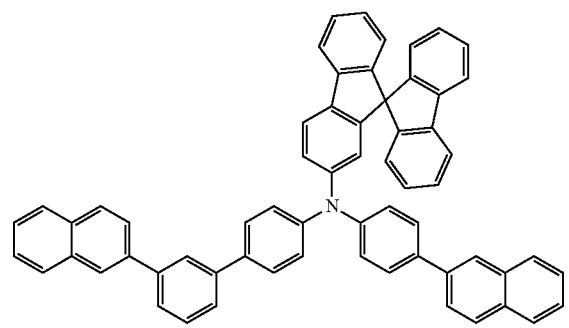
109
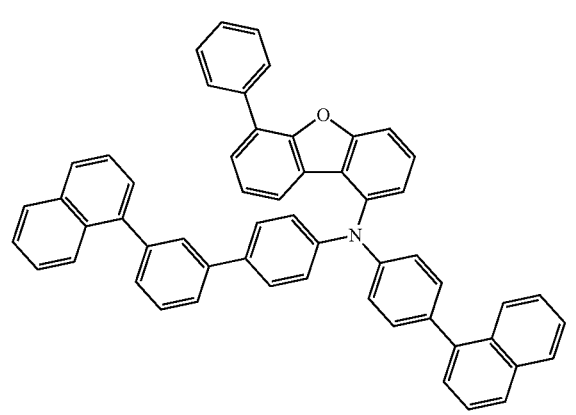
110
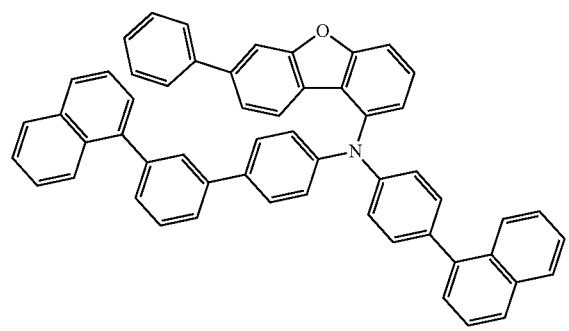
111
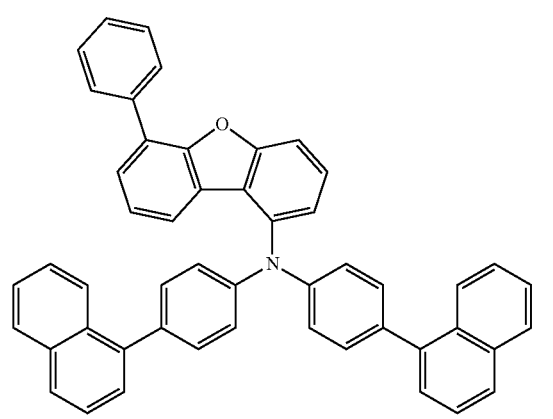
112
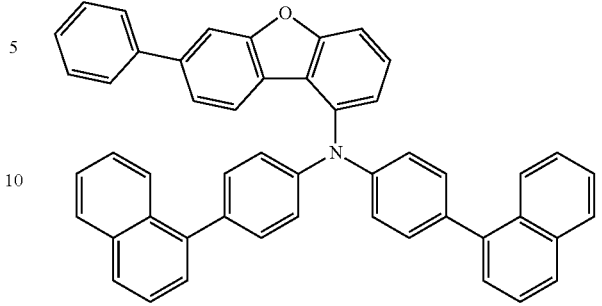
113
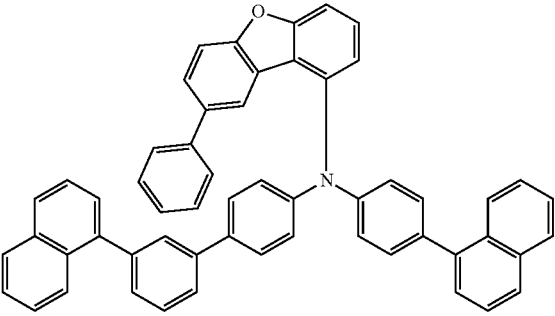
114
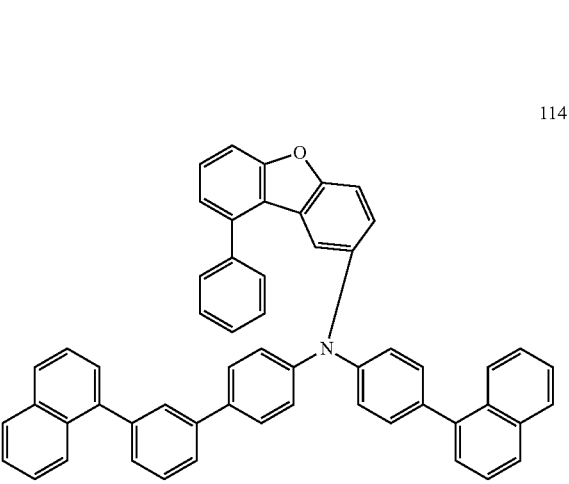
115
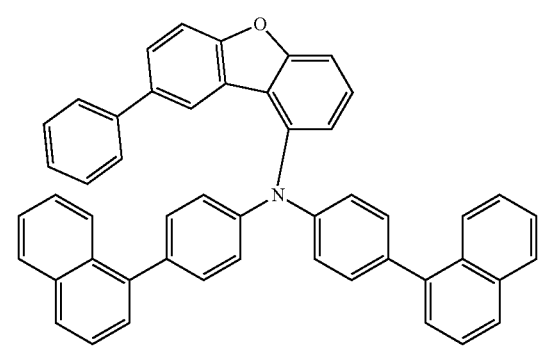

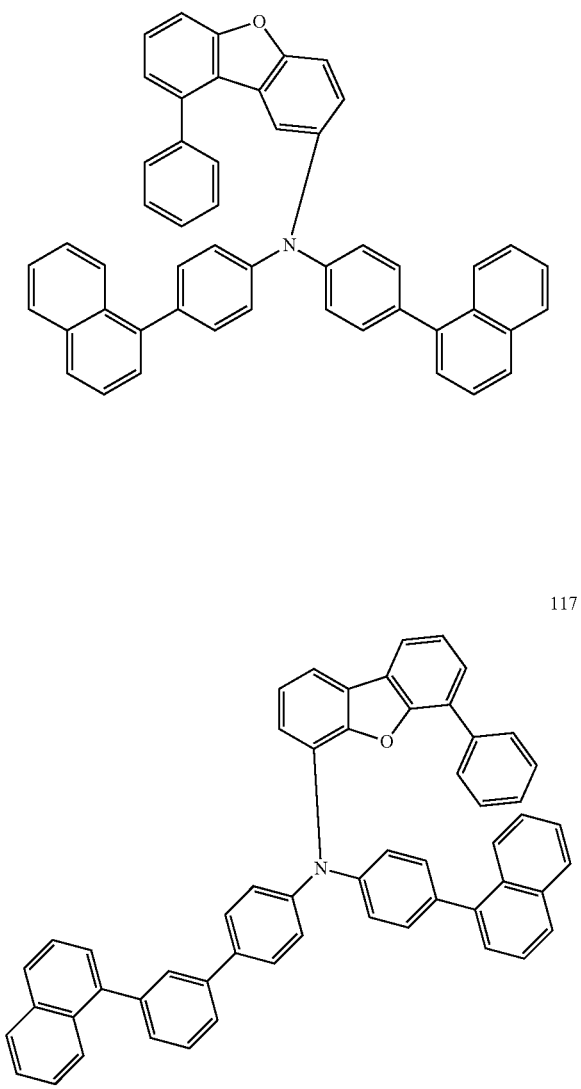

116

117

118

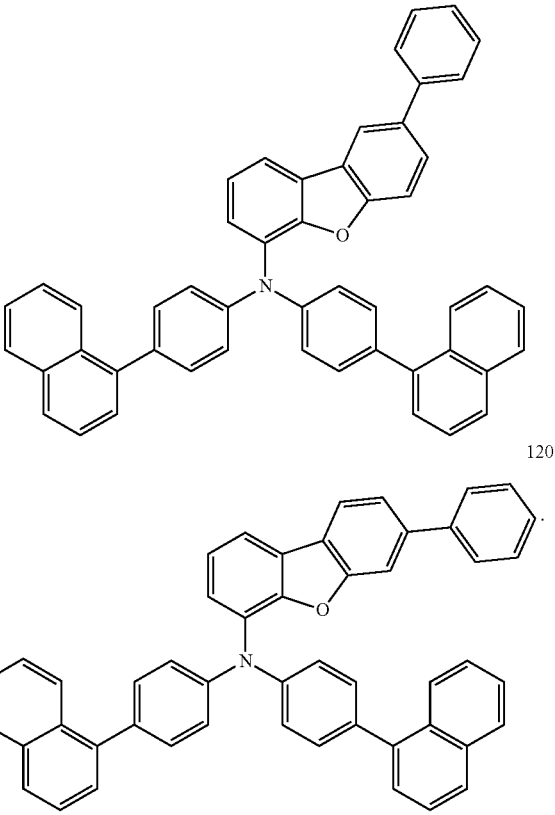

119

120

The material for an organic EL device according to an embodiment of the inventive concept may be included in at least one layer selected from a plurality of organic layers included in an organic EL device. For example, the material may be included in at least one layer selected from laminated layers disposed (e.g., positioned) between an emission layer and an anode of an organic EL device.

As described above, when the material for an organic EL device according to an embodiment of the inventive concept has a heteroaryl group, conjugation around the amine moiety may be secured and stability to radical may be enhanced. Accordingly, it may be possible to achieve a relatively high (or suitable) carrier resistance and long life expectancy. In addition, due to relatively high (or suitable) hole transportability of the heteroaryl group, high efficiency may be achieved. Additionally, since the heteroaryl group may be a molecule having high planarity such as, for example, a heteroaryl group that includes two benzene rings (e.g., a dibenzothiophene group, a carbazole group, and/or a dibenzofuran group), planarity of the entire compound represented by Formula 1 may be high, and thus packing may be easy, so that it may be possible to achieve low driving voltage.

Organic Electroluminescent Device

An organic electroluminescent (EL) device including a material according to an embodiment of the inventive concept will now be described with reference to FIG. 1. FIG. 1 is a schematic diagram showing an organic EL device 100 according to an embodiment of the inventive concept. The organic EL device 100 may include, for example, a substrate 102, an anode 104, a hole injection layer (HIL) 106, a hole transport layer (HTL) 108, an emission layer (EL) 110, an

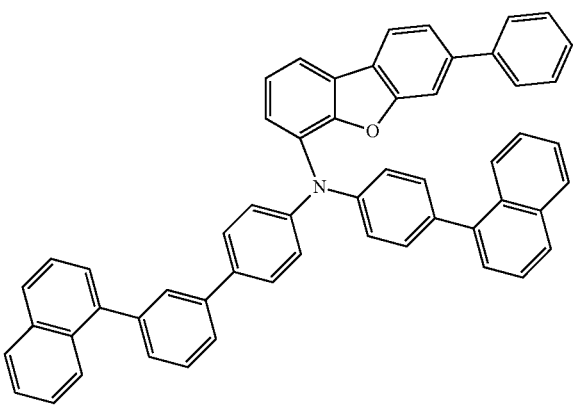

electron transport layer (ETL) 112, an electron injection layer (EIL) 114, and a cathode 116. In one embodiment, the material for an organic EL device according to an embodiment of the inventive concept may be used in at least one layer selected from the laminated layers disposed between the emission layer and the anode of the organic EL device.

Hereinafter, an example organic EL device, in which the material for an organic EL device according to an embodiment of the inventive concept is used in the hole transport layer 108, will be described.

The substrate 102 may be, for example, a transparent glass substrate or a flexible substrate (such as a semiconductor substrate resin including silicone).

The anode 104, which may be disposed on the substrate 102, may be formed by using indium tin oxide ($In_2O_3$—$SnO_2$, ITO), indium zinc oxide ($In_2O_3$—ZnO), etc.

The hole injection layer (HIL) 106 may be formed on the anode 104 by using any suitable material, such that the thickness of the HIL is about 10 nm or more to about 150 nm or less. For example, the HIL may include triphenyl amine-containing polyetherketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenyl benzidine (NPB), 4,4',4"-tris{N,N diphenylamino}triphenylamine (TDATA), 4,4',4"-tris(N,N-2-naphthylphenylamino)triphenylamine (2-TNATA), polyaniline/dodecylbenzene sulfonic acid (PANI/DBSA), poly(3,4-ethylene dioxythiophene)/poly(4-styrenesulfonate) (PEDOT/PSS), polyaniline/camper sulfonic acid (PANI/CSA), polyaniline/poly(4-styrenesulfonate) (PANI/PSS), etc.

The hole transport layer (HTL) 108 may be formed on the HIL 106 by using the material for an organic EL device according to an embodiment of the inventive concept, such that the thickness of the HTL is about 3 nm or more to about 100 nm or less. The HTL 108 (including the material for an organic EL device according to an embodiment of the inventive concept) may be, for example, formed by vacuum deposition.

The emission layer (EL) 110 may be formed on the HTL 108 by using any suitable host material, such that the thickness of the emission layer is about 10 nm or more to about 60 or less. In some embodiments, the emission layer 110 contains, for example, a condensed polycyclic aromatic derivative as a host material, and the derivative may be selected from anthracene derivatives, pyrene derivatives, fluoranthene derivatives, chrysene derivatives, benzanthracene derivatives, and/or triphenylene derivatives. For example, the emission layer 110 may contain an anthracene derivative and/or a pyrene derivative. The anthracene derivative used in the emission layer 110 may be represented by the following Formula 4:

Formula 4

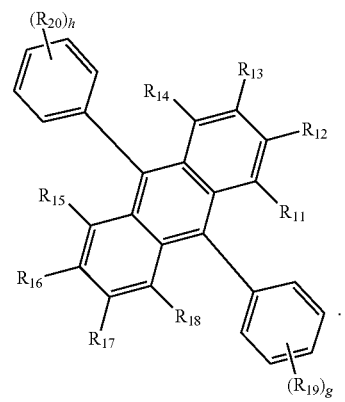

In Formula 4, $R_{11}$ to $R_{20}$ may each independently be selected from a substituted or unsubstituted aryl group having 6 to 30 ring-forming carbon atoms, a substituted or unsubstituted heteroaryl group having 1 to 30 ring-forming carbon atoms, an alkyl group having a carbon atom number of 1 to 15, a silyl group, a halogen atom, hydrogen, and deuterium. In addition, g and h may each independently be an integer from 0 to 5. In some embodiments, a plurality of adjacent $R_{11}$ to $R_{20}$ may bind to form a saturated or unsaturated ring.

Examples of the substituted or unsubstituted heteroaryl group having 1 to 30 ring-forming carbon atoms used in, for example, $R_{11}$ to $R_{20}$ may include, but are not limited to, a benzothiazolyl group, a thiophenyl group, a thienothiophenyl group, a thienothienothiophenyl group, a benzothiophenyl group, a benzofuryl group, a dibenzothiophenyl group, a dibenzofuryl group, an N-aryl carbazolyl group, an N-heteroaryl carbazolyl group, an N-alkyl carbazolyl group, a phenoxazyl group, a phenothiazyl group, a pyridyl group, a pyrimidyl group, a triazyl group, quinolinyl group, a quinoxalyl group, etc.

In addition, the alkyl group having a carbon atom number of 1 to 15 used in, for example, $R_{11}$ to $R_{20}$ may each independently include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxyl methyl group, a 1-hydroxyl ethyl group, a 2-hydroxyl ethyl group, a 2-hydroxyl isobutyl group, a 1,2-dihydroxyl ethyl group, a 1,3-dihydroxyl isopropyl group, a 2,3-dihydroxyl-t-butyl group, a 1,2,3-trihydroxyl propyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, etc. For example, $R_{11}$ to $R_{20}$ may each independently include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and/or a 2-norbornyl group, but are not specifically limited thereto.

For example, the anthracene derivatives used in the emission layer 110 of the organic EL device according to an embodiment of the inventive concept may be represented by Compounds a-1 to a-12 (collectively denoted as Formula 5).

Formula 5 a-1

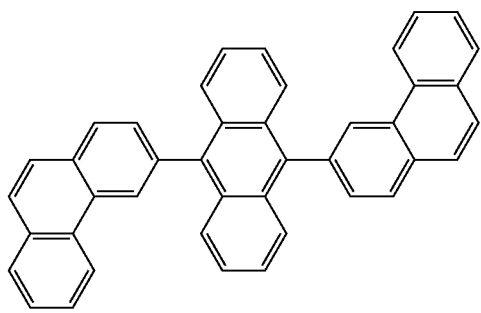

a-2

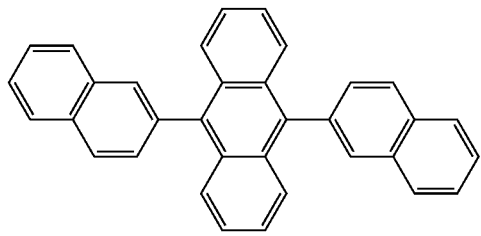

a-3

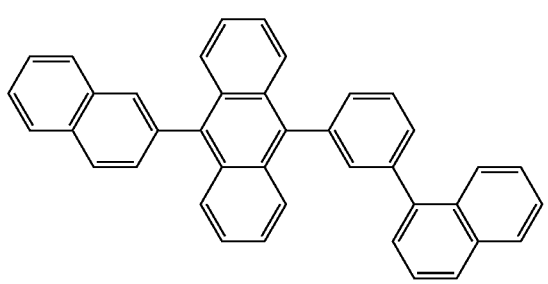

a-4

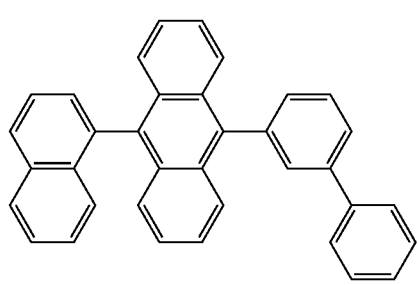

-continued a-5

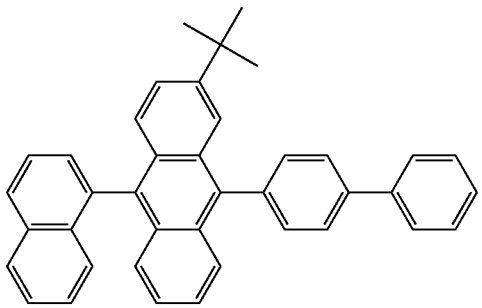

a-6

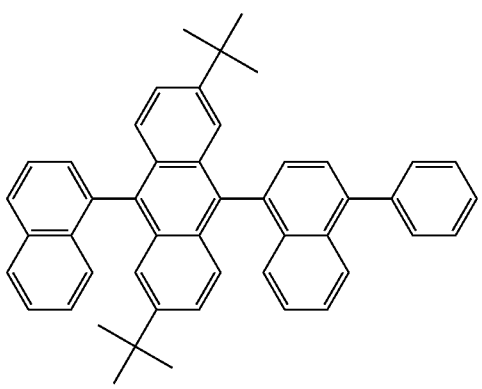

a-7

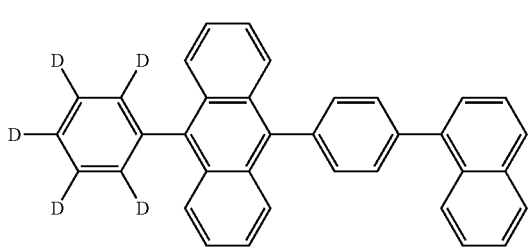

a-8

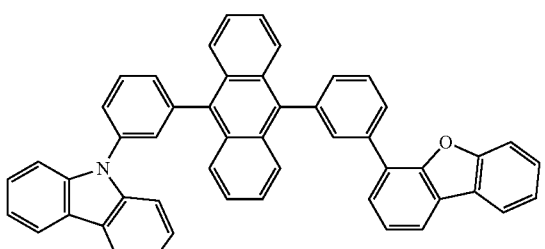

a-9

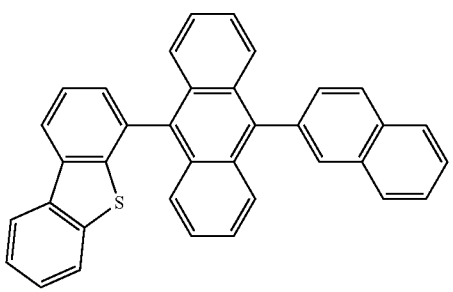

a-10

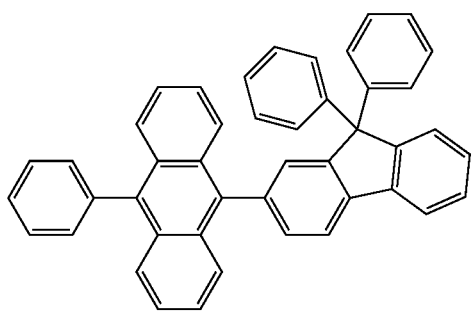

a-11

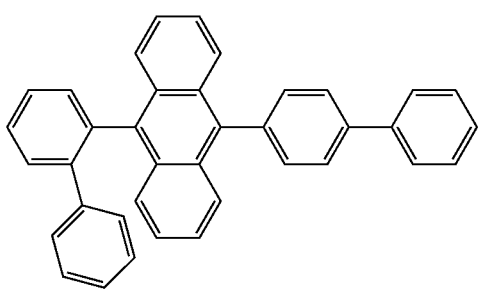

a-12

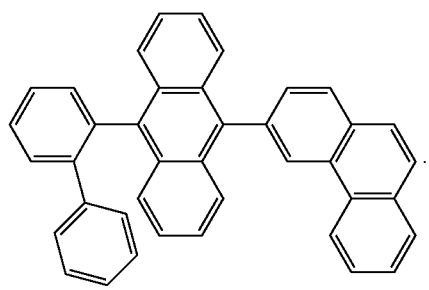

As dopant materials, the emission layer 110 may include, but is not limited to, a styryl derivative (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl) naphthalene-2-yl)vinyl)phenyl-N-phenylbenzenamine (N-BDAVBi)), perylene and/or a derivative thereof (e.g., 2,5,8,11-tetra-t-butylperylene (TBPe)), and/or pyrene and/or a derivative thereof (e.g., 1,1-dipyrene, 1,4-di pyrenylbenzene, and/or 1,4-Bis(N,N-diphenylamino)pyrene).

The electron transport layer (ETL) 112 may be formed on the emission layer 110 by using any suitable material including, for example, tris(8-hydroxyquinolinato)aluminum($Alq_3$) and/or a material having a nitrogen-containing aromatic ring (e.g., a material including a pyridine ring (e.g., 1,3,5-tri[(3-pyridyl)-phen-3-yl]benzene), a material including a triazine ring (e.g., 2,4,6-tris(3'-(pyridine-3-yl)biphenyl-3-yl)-1,3,5-triazine), and/or a material including an imidazole derivative (e.g., 2-(4-N-phenylbenzoimidazolyl-1-ylphenyl)-9,10-dinaphthylanthracene)), such that the ETL has a thickness of about 15 nm or more to about 50 nm or less.

The electron injection layer (EIL) 114 may be formed on the ETL 112 by using any suitable material including, for example, lithium fluoride (LiF), and/or lithium-8-quinolinato (Liq), such that the EIL has a thickness of about 0.3 nm or more to about 9 nm or less.

The cathode 116, which may be disposed (e.g., positioned) on the EIL 114, may be formed by using a metal (such as aluminum (Al), argentum (silver) (Ag), lithium (Li), magnesium (Mg), and/or calcium (Ca)), a mixture thereof, and/or a transparent material (such as ITO and/or $In_2O_3$—ZnO).

Each of the above-described electrodes and layers, which constitute the organic EL device according to an embodiment of the inventive concept, may be formed by selecting one or more appropriate (or suitable) membrane-forming methods such as vacuum deposition, sputtering, and/or various coatings, depending on materials.

By using the material for an organic EL device according to an embodiment of the inventive concept as described above, a hole transport layer capable of achieving high efficiency and long life expectancy of an organic EL device may be realized.

In some embodiments, in the organic EL device 100 according to an embodiment of the inventive concept, the material for an organic EL device according to an embodiment of the inventive concept as described above may be used as a material for the hole injection layer. As described above, the material for an organic EL device according to an embodiment of the inventive concept may be included in at least one layer selected from the plurality of organic layers which constitute the organic EL device, and may achieve high efficiency and long life expectancy of the organic EL device.

In addition, the material for an organic EL device according to an embodiment of the inventive concept may also be applied to an organic EL emitter of an active matrix using a thin film transistor (TFT).

Preparation Method

The material for an organic electroluminescent (EL) device according to an embodiment of the inventive concept may be synthesized, for example, as follows.

Synthesis Method of Compound 21

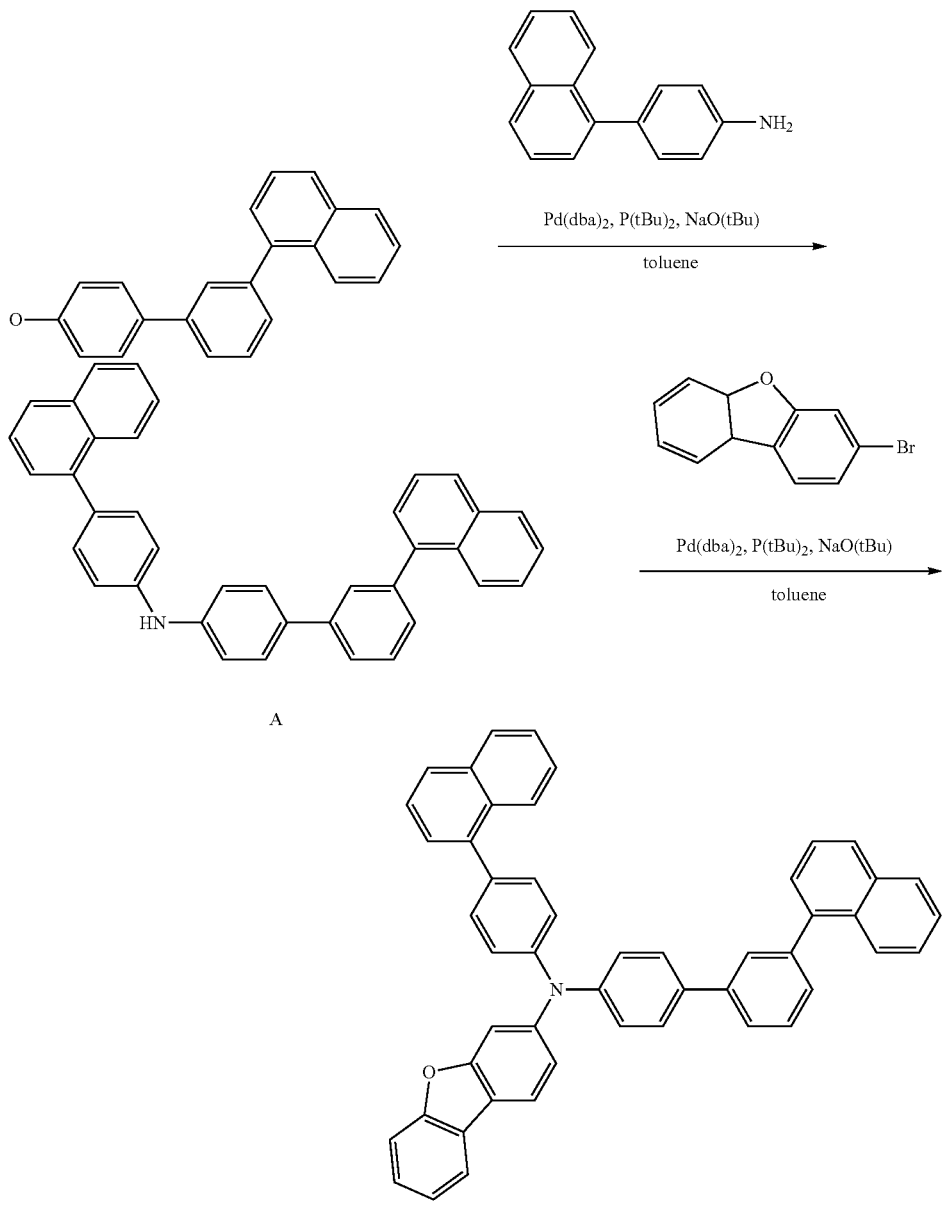

Formula 6

Synthesis of Compound A

Under Ar atmosphere, about 10.05 g (31.92 mmol) of 1-(4'-chloro-[1,1'-biphenyl]-3-yl)naphthalene, about 7.0 g (31.92 mmol) of 4-(naphthalene-1-yl)aniline, about 2.313 g (2.235 mmol) of $Pd_2(dba)_3 \cdot CHCl_3$, about 3.352 ml (6.704 mmol) of $(tBu)_3P$ (1.50 M), and about 9.203 g (95.768 mmol) of NaO$^t$Bu were added to a 3-neck flask of 500 mL, and then the resultant was heated and refluxed in the mixed solvent of about 200 mL of toluene for about 4 hours, with stirring. After air cooling, water was added to separate the organic layer, and then solvent was distilled. The resulting crude product was purified with silica gel column chromatography (using a mixed solvent of $CH_2Cl_2$ and hexane), and then recrystallization was performed with the mixed solvent of toluene/hexane to yield about 12. 4 g of compound A (yield 78%) as a white solid. The molecular weight of compound A measured by fast atom bombardment mass spectrometry (FAB-MS) was about 497.

Synthesis of Compound 21

Under Ar atmosphere, about 3.00 g (6.03 mmol) of compound A, about 1.788 g (7.23 mmol) of 3-bromodibenzo[b, d]furan, about 0.243 g (0.422 mmol) of $Pd_2(dba)_3$, about 0.633 ml (1.266 mmol) of $(tBu)_3P$ (1.50 M), and about 1.738 g (18.086 mmol) of NaOtBu were added to a 3-neck flask of 200 mL, and the resultant was heated and refluxed in the mixed solvent of about 70 mL of toluene for about 3 hours, with stirring. After air cooling, water was added to separate the organic layer, and then solvent was distilled. The resulting crude product was purified with silica gel column chromatography (using the mixed solvent of $CH_2Cl_2$ and hexane), and then recrystallization was performed with the mixed solvent of toluene/ethanol to yield about 3.68 g of compound 21 (yield 92%) as a white solid.

Synthesis Method of Compound 37

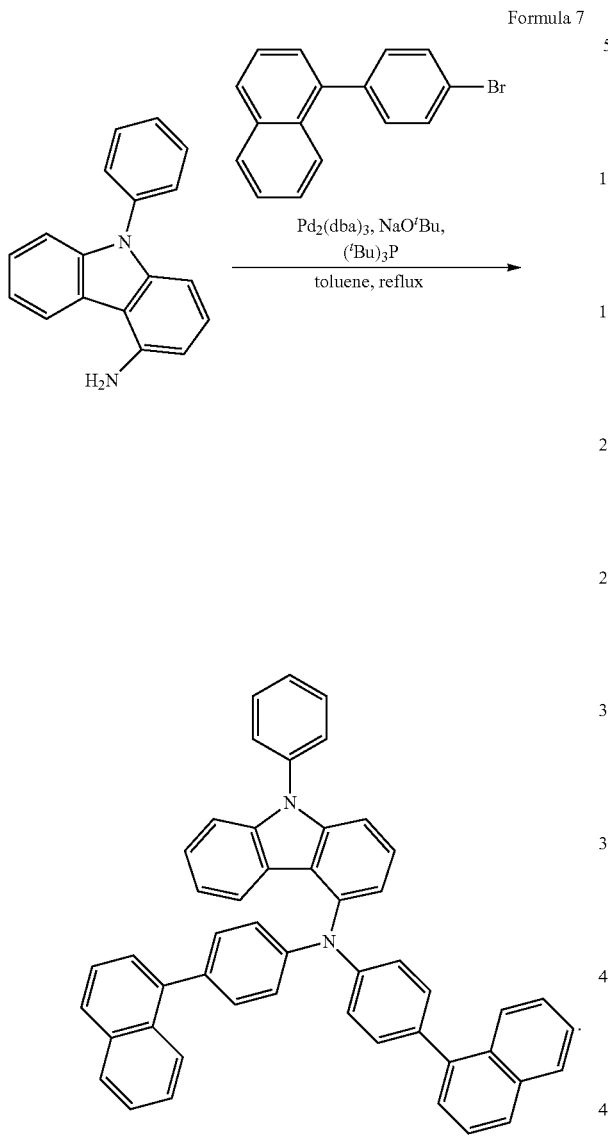

Under Ar atmosphere, about 1.37 g (5.30 mmol) of 9-phenyl-9H-carbazol-4-amine, about 3.00 g (10.59 mmol) of 1-(4-bromophenyl)naphthalene, about 0.30 g (2.12 mmol) of Pd$_2$(dba)$_3$, about 1.41 ml (2.12 mmol) of (tBu)$_3$P (1.50 M), and about 8.89 g (6.03 mmol) of NaO$^t$Bu were added to a 3-neck flask of 300 mL, and the resultant was heated and refluxed in the mixed solvent of about 106 mL of toluene for about 1.5 hours, with stirring. After air cooling, water was added to separate the organic layer, and then solvent was distilled. The resulting crude product was purified with silica gel column chromatography (using a mixed solvent of CH$_2$Cl$_2$ and hexane), and then recrystallization was performed with the mixed solvent of toluene/ethanol to yield about 3.34 g of compound 37 (yield 95%).

The molecular weight of compound 37 measured by FAB-MS was about 662. In addition, the chemical shift value (δ) of 37 measured by $^1$H-NMR (CDCl$_3$) was as follows: 8.01-7.96 (m, 3H), 7.90 (d, 2H, J=8.10 Hz), 7.83 (d, 2H, J=8.10 Hz), 7.53-7.33 (m, 20H), 7.23 (d, 1H, J=7.50 Hz), 7.16-7.12 (m, 1H).

Synthesis Method of Compound 41

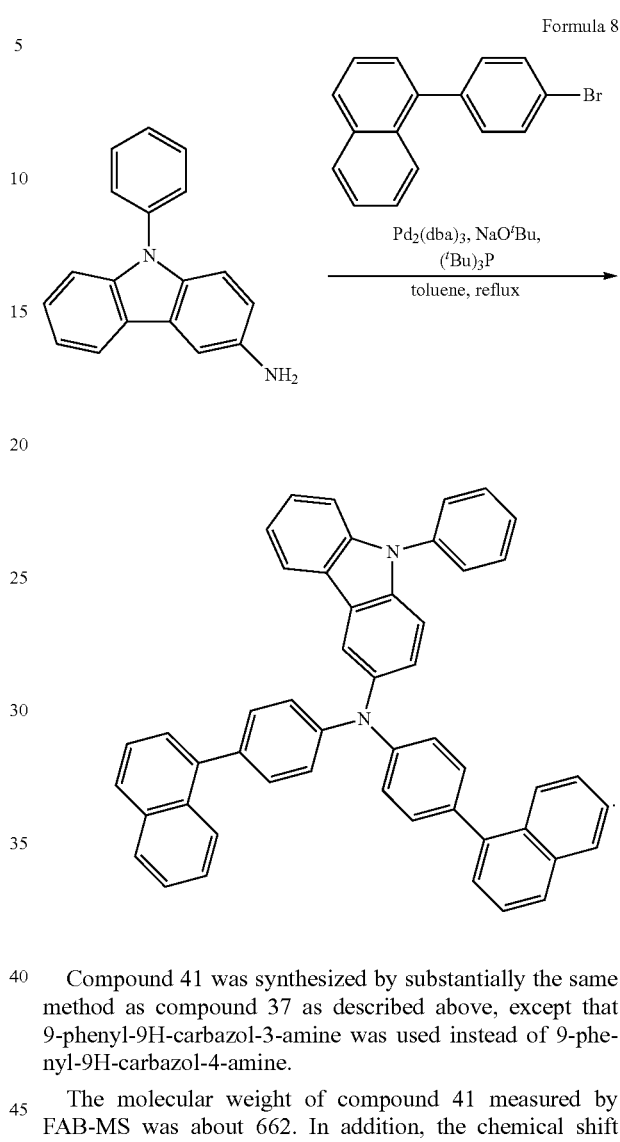

Compound 41 was synthesized by substantially the same method as compound 37 as described above, except that 9-phenyl-9H-carbazol-3-amine was used instead of 9-phenyl-9H-carbazol-4-amine.

The molecular weight of compound 41 measured by FAB-MS was about 662. In addition, the chemical shift value (δ) of 41 measured by $^1$H-NMR (CDCl$_3$) was as follows: 8.13-8.07 (m, 4H), 7.91-7.88 (m, 2H), 7.84 (d, 2H, J=7.80 Hz), 7.63-7.59 (m, 4H), 7.55-7.40 (m, 17H), 7.34-7.29 (m, 5H).

Synthesis Method of Compound 52

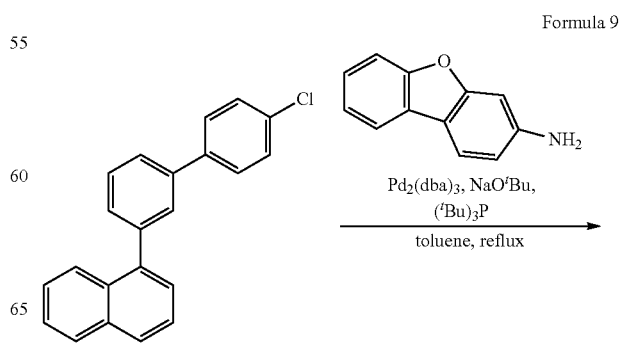

49
-continued

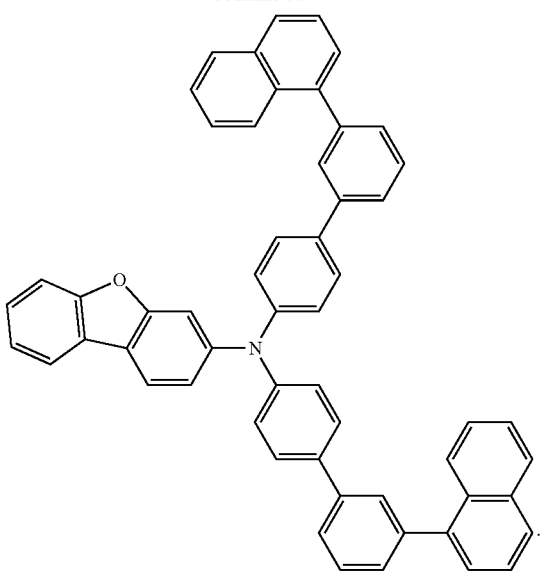

Compound 52 was synthesized by substantially the same method as compound 37 as described above, except that dibenzo[b, d]furan-3-amine and 1-(4'-chloro-[1,1'-biphenyl]-3-yl)naphthalene, respectively, were used instead of 9-phenyl-9H-carbazol-4-amine and (4-bromophenyl)naphthalene.

The molecular weight of compound 52 measured by FAB-MS was about 739. In addition, the chemical shift value (δ) of 52 measured by $^1$H-NMR (CDCl$_3$) were as follows: 7.98-7.86 (m, 7H), 7.82 (d, 1H, J=8.40 Hz), 7.73-7.72 (m, 2H), 7.67-7.64 (m, 2H), 7.59-7.43 (m, 16H), 7.42-7.28 (m, 4H), 7.25-7.23 (m, 4H), 7.19 (dd, 1H, J=1.8, J=8.4 Hz).

Synthesis Method of Compound 57

Formula 10

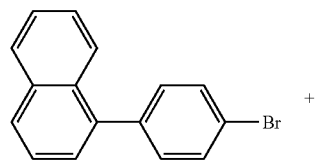
+
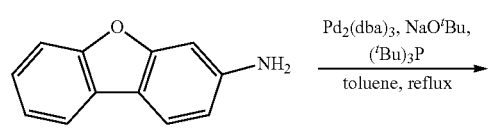

50
-continued

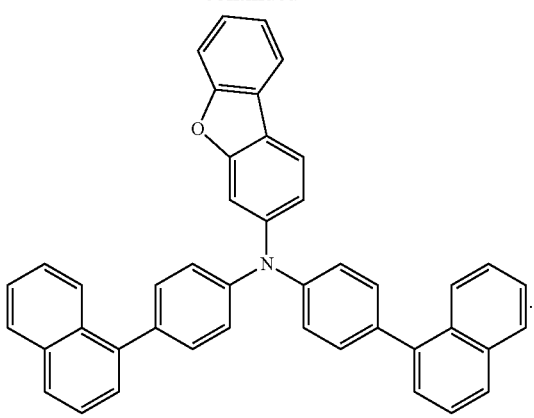

Compound 57 was synthesized by substantially the same method as compound 37 as described above, except that dibenzo[b, d]furan-3-amine was used instead of 9-phenyl-9H-carbazol-4-amine.

The molecular weight of compound 57 measured by FAB-MS was about 739. In addition, the chemical shift value (δ) of compound 57 measured by $^1$H-NMR (CDCl$_3$) was as follows: 8.10-8.02 (m, 2H), 7.95-7.82 (m, 6H), 7.60-7.42 (m, 14H), 7.42-7.27 (m, 7H).

Synthesis Method of Compound 59

Compound 59 was synthesized by substantially the same method as compound 37 as described above, except that 9-phenyl-9H-carbazol-3-amine and 2-(4-bromophenyl)naphthalene, respectively, were used instead of 9-phenyl-9H-carbazol-4-amine and 1-(4-bromophenyl)naphthalene.

The molecular weight of compound 59 measured by FAB-MS was about 587. In addition, the chemical shift value (δ) of 59 measured by $^1$H-NMR (CDCl$_3$) was as follows: 8.05 (m, 2H), 7.95-7.80 (m, 8H), 7.76 (d, 2H, J=7.5 Hz), 7.68 (d, 4H, J=8.7 Hz), 7.56-7.35 (m, 7H) 7.31 (d, 4H, J=8.7 Hz) 7.26-7.20 (m, 2H).

Organic EL devices of Examples 1 to 6 were manufactured by the preparation method as described above by using compounds 21, 37, 41, 52, 57, and 59 described above as hole transport materials.

Example compound 21

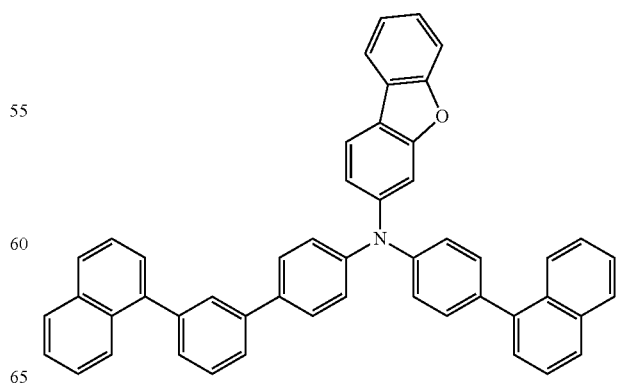

Example compound 37
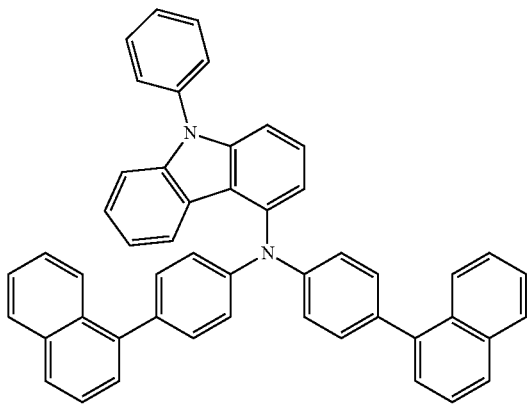
Example compound 41
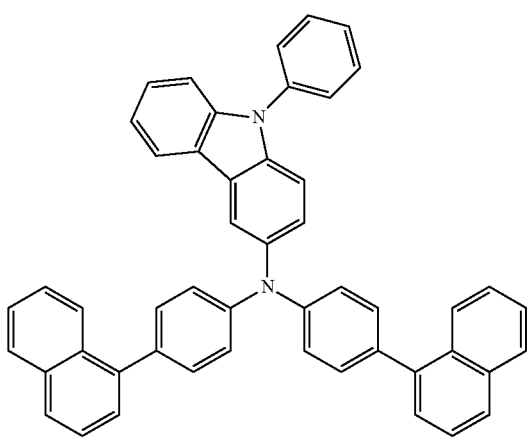
Example compound 52
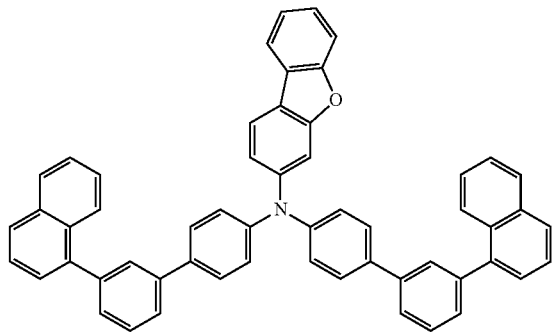
Example compound 57
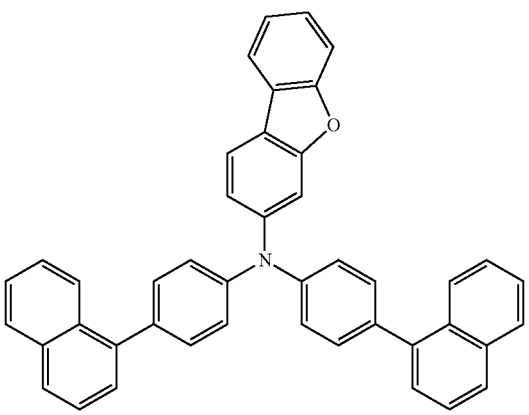
Example compound 59
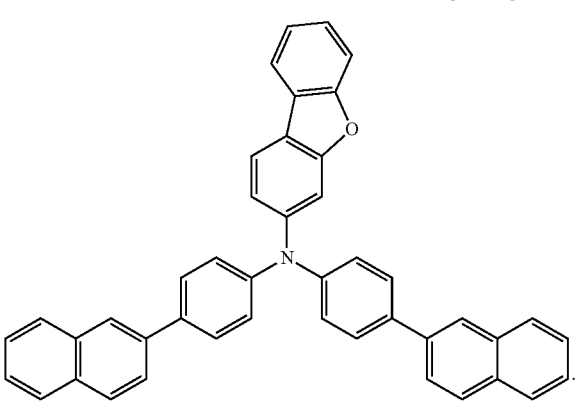
Additionally, organic EL devices of Comparative Examples 1 to 6 were manufactured by using Comparative Example compounds c-1 to c-6 as hole transport materials.
Comparative Example compound c-1
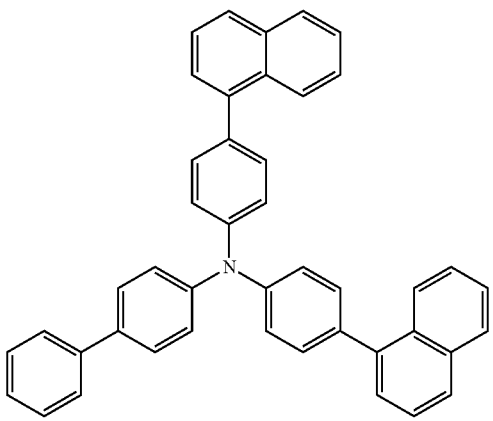

Comparative Example compound c-2

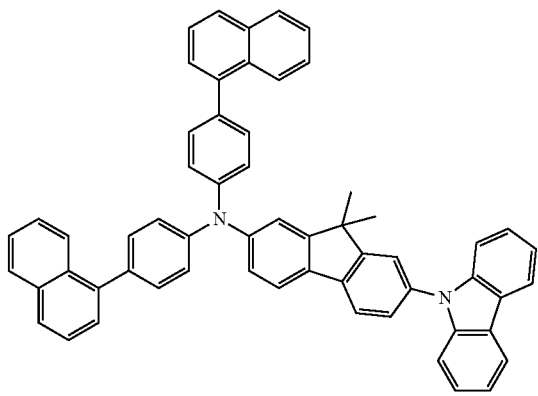

Comparative Example compound c-5

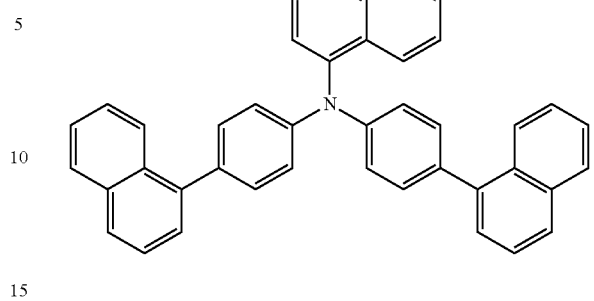

Comparative Example compound c-3

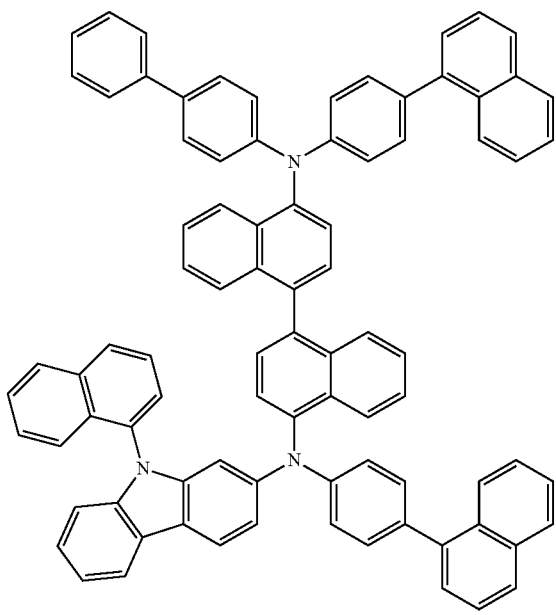

Comparative Example compound c-6

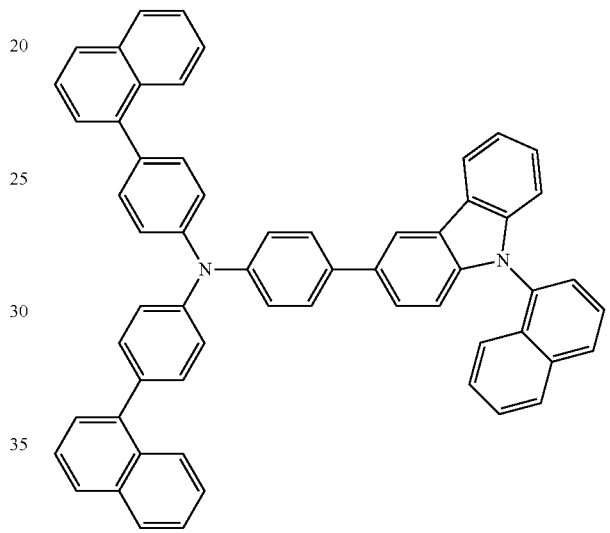

Comparative Example compound c-4

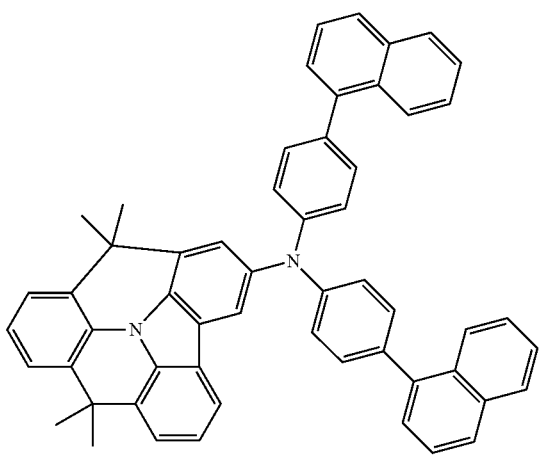

Figure 2:
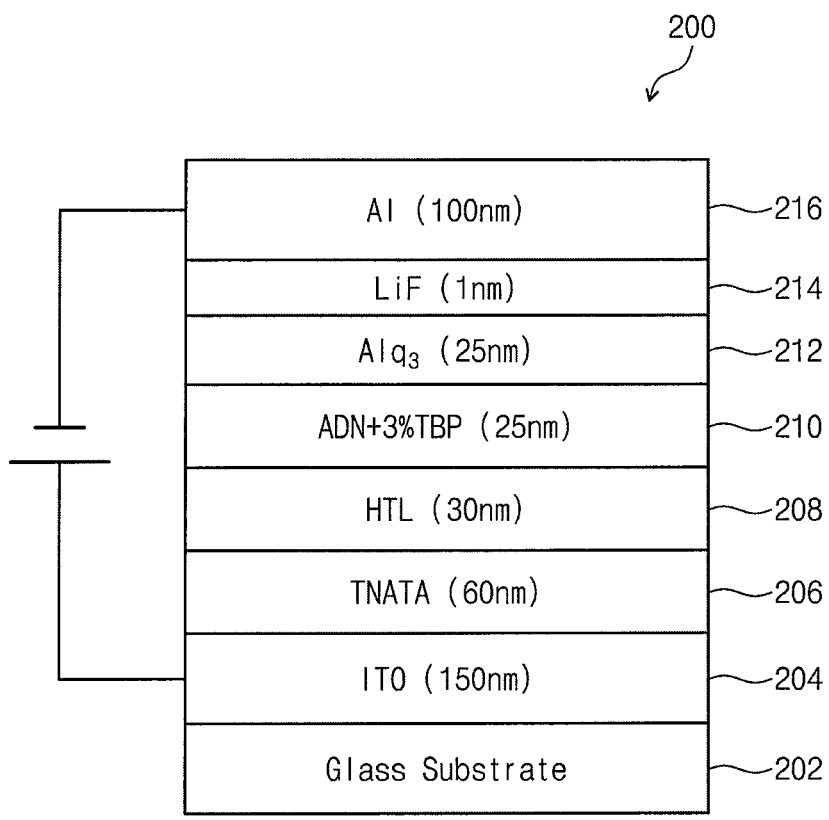
FIG. 2 is a schematic diagram showing an organic EL device 200 according to an embodiment of the inventive concept.

An organic EL device 200 according to the present example is shown in FIG. 2. In organic EL devices according to Examples 1 to 6 and Comparative Examples 1 to 6, a transparent glass substrate was used as the substrate 202; an anode 204 was formed of ITO with a membrane thickness of about 150 nm; a hole injection layer 206 was formed of 2-TNATA and to have a membrane thickness of about 60 nm; a hole transport layer 208 was formed to include the corresponding compound as shown in Table 1 and to have a membrane thickness of about 30 nm; an emission layer 210 was formed to have membrane thickness of about 25 nm by applying 3% of TBP to ADN (e.g., by doping ADN with 3% of TBP); an electron transport layer 212 was formed of $Alq_3$ and to have a membrane thickness of 25 nm; an electron injection layer 214 was formed of LiF and to have a membrane thickness of about 1 nm; and a cathode 216 was formed of Al and to have a membrane thickness of about 100 nm.

Emission efficiency and half-life of the organic EL devices 200 manufactured according to Examples and Comparative Examples were evaluated. Here, the voltage and emission efficiency were measured with a current density at 10 $mA/cm^2$, and half-life (LT50) indicates the time required for the brightness of the organic EL device to drop to half of the initial brightness of 1,000 $cd/m^2$. Evaluation results are shown in Table 1.

TABLE 1

| Example of manufacture of device | Hole transport layer | Current density (mA/cm$^2$) | Voltage (V) | Emission efficiency (cd/A) | Life expectancy LT50 (h) |
|---|---|---|---|---|---|
| Example 1 | Example compound 21 | 10 | 5.2 | 6.3 | 1,950 |
| Example 2 | Example compound 37 | 10 | 5.1 | 6.2 | 1,850 |
| Example 3 | Example compound 41 | 10 | 5.0 | 6.2 | 1,750 |
| Example 4 | Example compound 52 | 10 | 5.1 | 6.2 | 1,750 |
| Example 5 | Example compound 57 | 10 | 5.2 | 6.3 | 1,800 |
| Example 6 | Example compound 59 | 10 | 5.1 | 6.1 | 1,850 |
| Comparative Example 1 | Comparative Example compound c-1 | 10 | 6.3 | 5.2 | 1,350 |
| Comparative Example 2 | Comparative Example compound c-2 | 10 | 6.5 | 5.1 | 1,450 |
| Comparative Example 3 | Comparative Example compound c-3 | 10 | 6.6 | 5.2 | 1,500 |
| Comparative Example 4 | Comparative Example compound c-4 | 10 | 6.5 | 5.3 | 1,400 |
| Comparative Example 5 | Comparative Example compound c-5 | 10 | 6.6 | 5.2 | 1,350 |
| Comparative Example 6 | Comparative Example compound c-6 | 10 | 6.5 | 5.2 | 1,400 |

As can be seen from the results in Table 1, organic EL devices of Examples 1 to 6 show high efficiency and long life expectancy, as compared with those of Comparative Examples 1 to 6. Without being bound by any particular theory, it is believed that the compound according to an embodiment of the inventive concept contributes to high carrier resistance and long life expectancy by including a heteroaryl group to secure the conjugation around the amine moiety and enhance stability to radical. In addition, due to high hole transportability of the heteroaryl group, high efficiency may be achieved. For example, the compound according to an embodiment of the inventive concept may have low driving voltage. It is believed that such results are at least in part due to the fact that the compound of the present embodiments includes a heteroaryl group having a relatively high planarity (e.g., a group that is substantially planar) such as a heteroaryl group that includes two benzene rings (e.g., a dibenzothiophene group, a carbazole group, and/or a dibenzofuran group), which in turn increases the planarity of the entire molecule and promotes easy packing. Accordingly, Comparative Examples 1 to 6 that lack such heteroaryl group show shorter life expectancy and lower efficiency. It is also believed that, due to the presence of a quaternary carbon, Comparative Examples 2 and 4 exhibited weak thermal resistance, which lead to decline in life expectancy. In addition, Comparative Example 3, which included a diamine compound (e.g., a compound having two amine moieties), exhibited low carrier resistance and reduced life expectancy.

As can be seen from the results shown in Table 1, when the material for an organic EL device according to an embodiment of the inventive concept is used as a hole transport material, higher efficiency and extended life expectancy of the organic EL device may be realized, as compared to the organic EL devices of Comparative Examples. For example, it is believed that, by introducing fluorenyl and naphthyl groups having high resistance to charges into an amine moiety of the compound of an embodiment of the inventive concept, the material for an organic EL device including the compound may achieve high efficiency and long life expectancy.

In addition, since the material for an organic EL device according to an embodiment of the inventive concept has a broad energy gap, the material may be applied to red and green light-emitting regions of the organic EL device.

According to embodiments of the inventive concept, the material for an organic EL device may achieve low voltage driving, high emission efficiency, and long life expectancy. Since the material for an organic EL device of an embodiment of the inventive concept has a heteroaryl group, conjugation around an amine moiety may be secured and stability to radical may be enhanced, so that carrier resistance may be high, and life expectancy may be extended. In addition, due to high hole transportability of the heteroaryl group, high efficiency may be achieved. Additionally, since a molecule having high planarity, such as a heteroaryl group that includes two benzene rings (e.g., a dibenzothiophene group, a carbazole group, and/or a dibenzofuran group), is introduced, planarity of the entire molecule may be increased, and packing may be easy, thereby resulting in low driving voltage. The above-described effects are particularly significant in a blue light-emitting region.

As used herein, expressions such as "at least one of," "one of," "at least one selected from," and "one selected from," when preceding a list of elements, modify the entire list of elements and do not modify the individual elements of the list. Further, the use of "may" when describing embodiments of the present invention refers to "one or more embodiments of the present invention."

In addition, as used herein, the terms "use," "using," and "used" may be considered synonymous with the terms "utilize," "utilizing," and "utilized," respectively.

As used herein, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The above-disclosed subject matter is to be considered illustrative and not restrictive, and the appended claims and equivalents thereof are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.
What is claimed is:
1. A material for an organic electroluminescent device represented by one of Compounds 1 to 120 (collectively denoted as Formula 3):
Formula 3
1
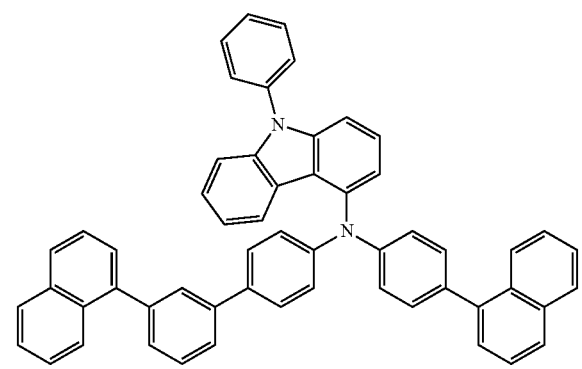
2
3
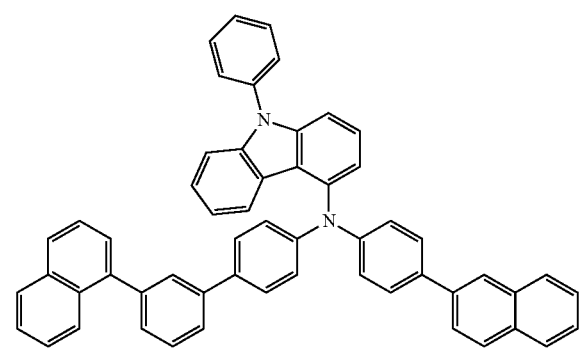
4
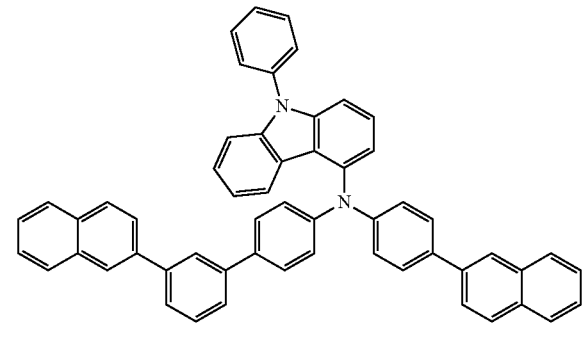
5
6
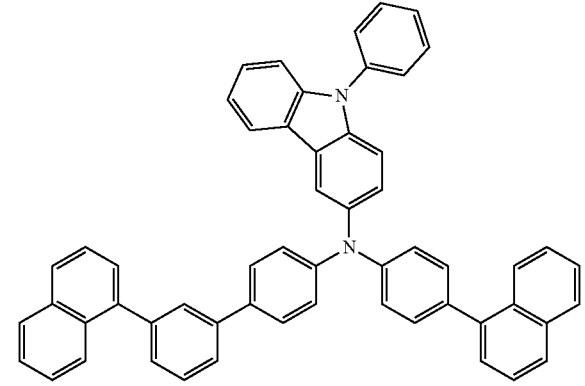
7
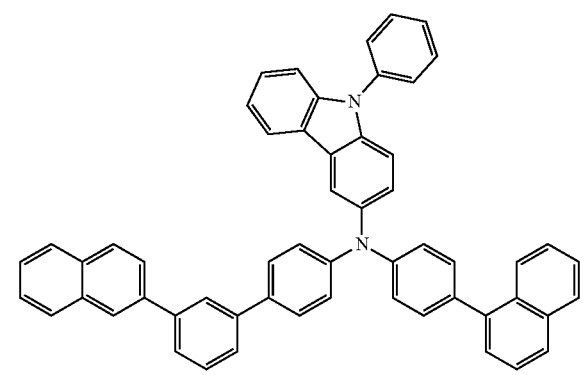

8
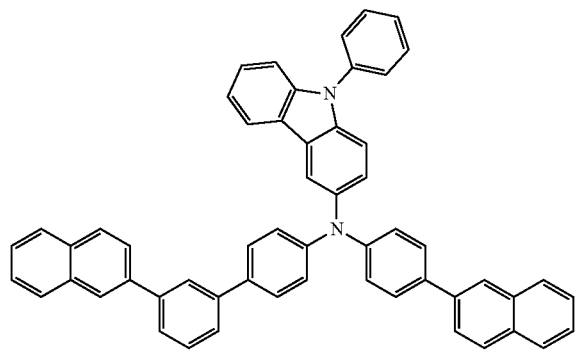
9
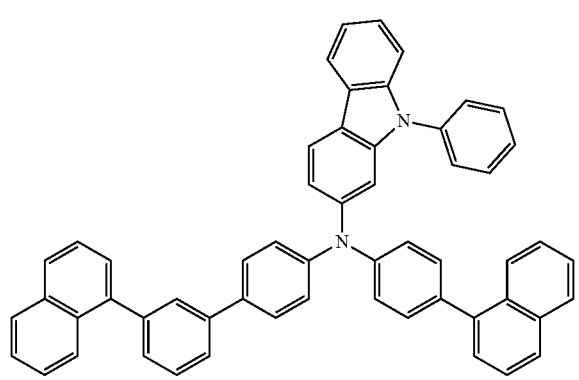
10
11
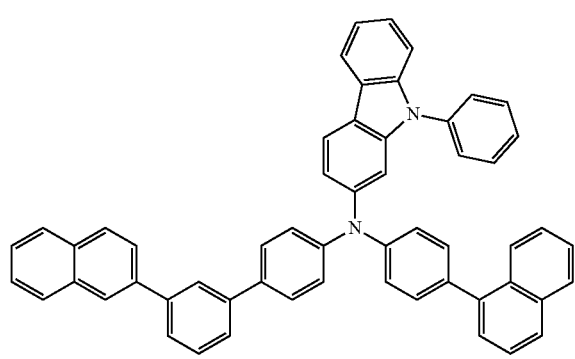
12
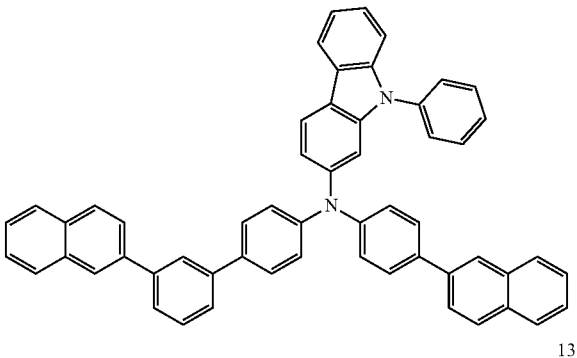
13
14
15
16

17
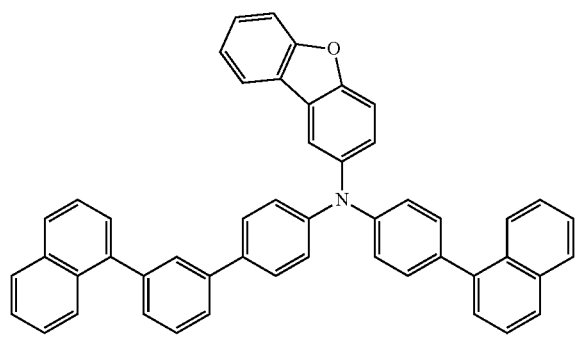
18
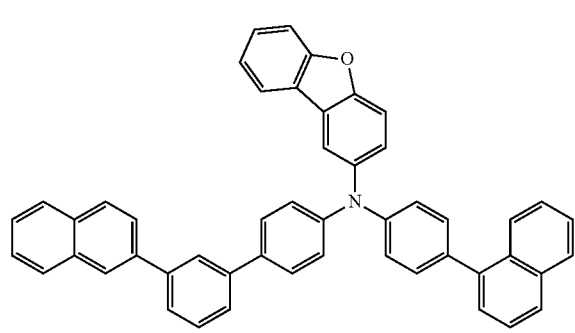
19
21
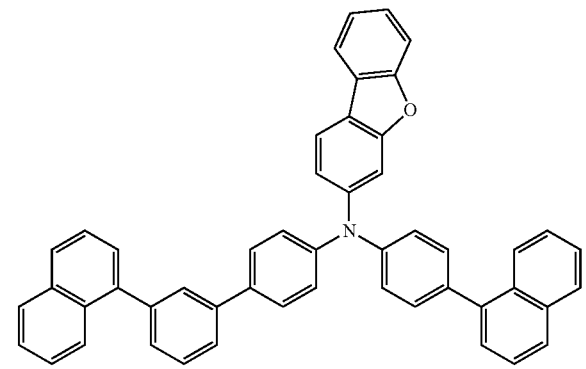
22
23
24
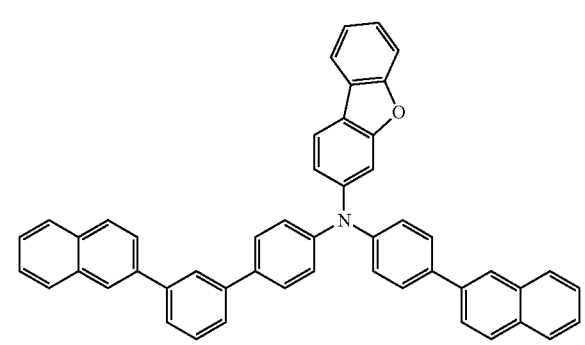
20

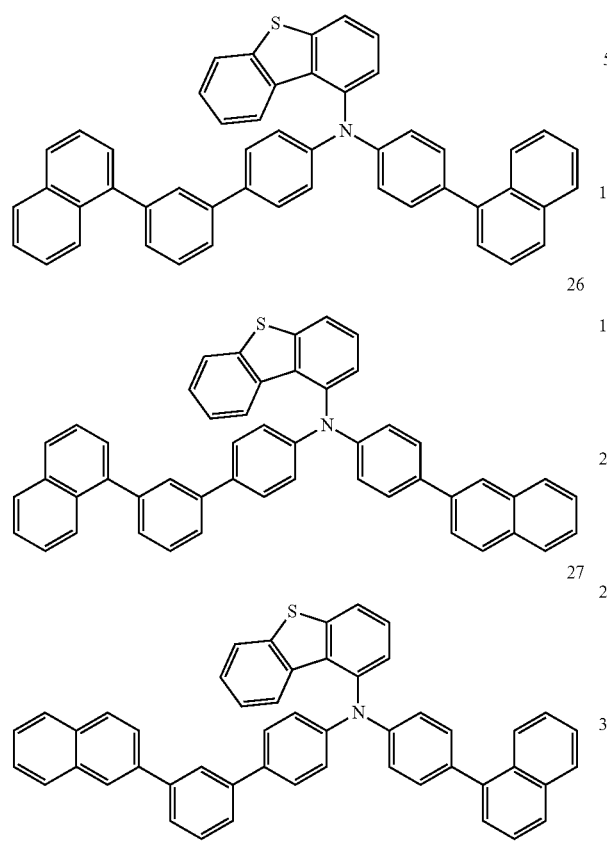
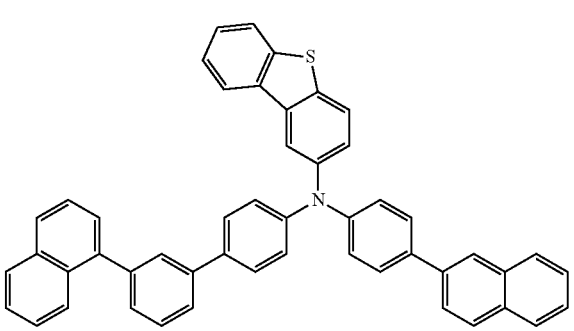
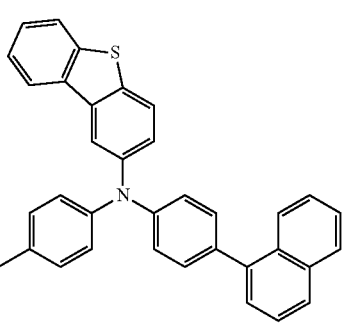
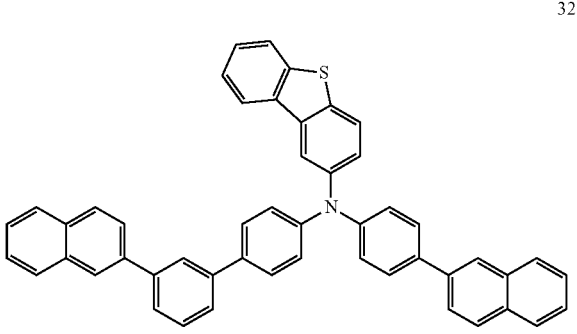
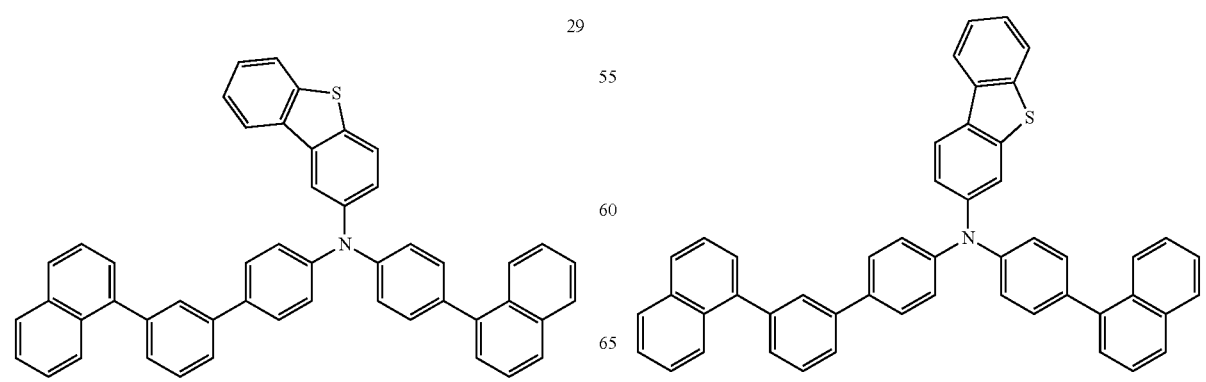

34
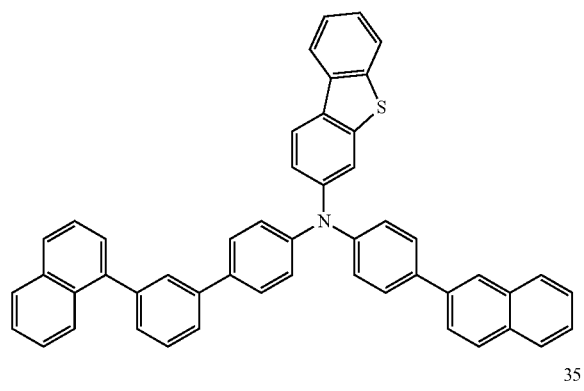
35
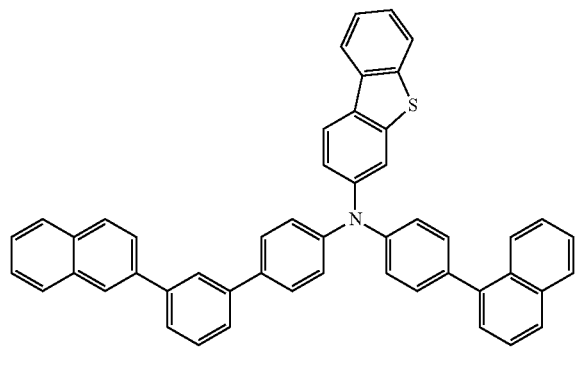
36
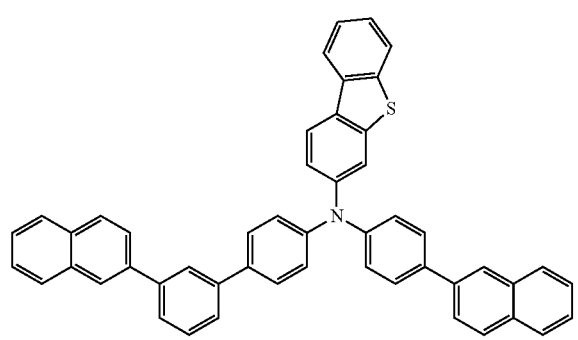
37
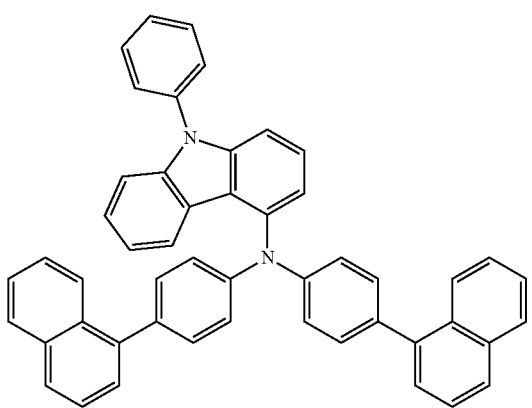
38
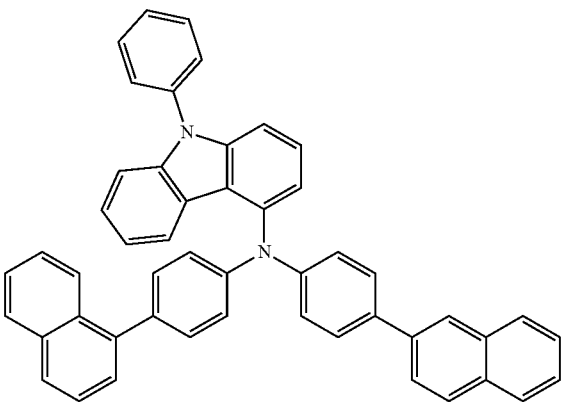
39
40
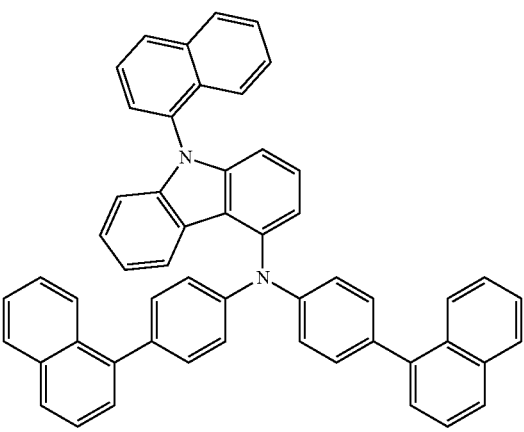

41
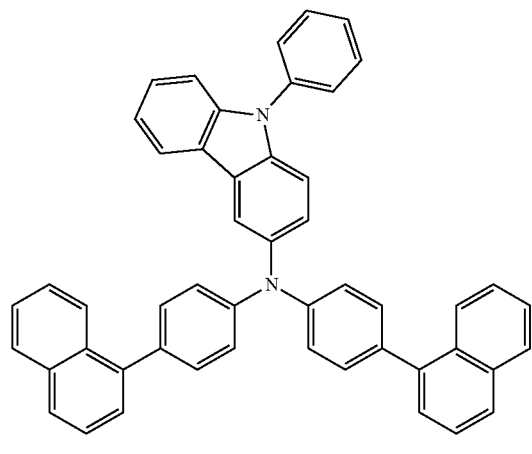
42
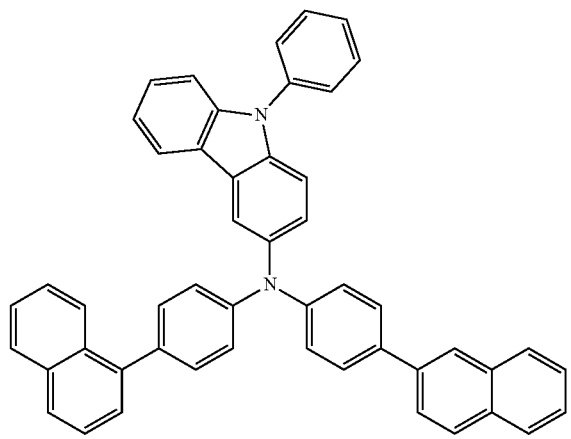
43
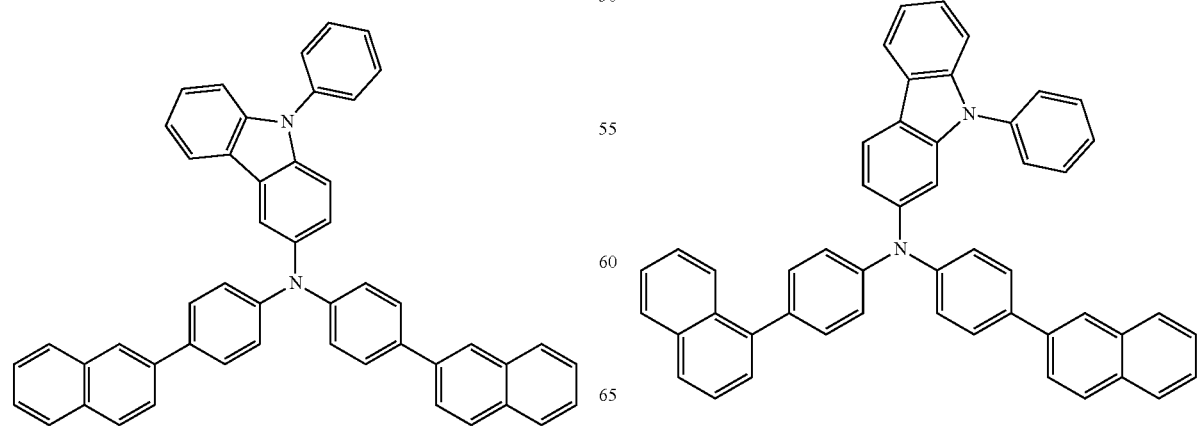
44
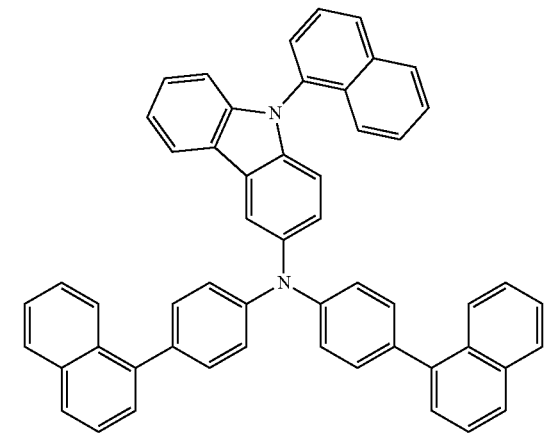
45
45
46

47
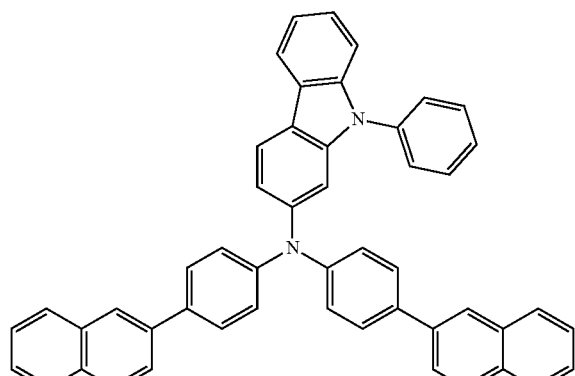
48
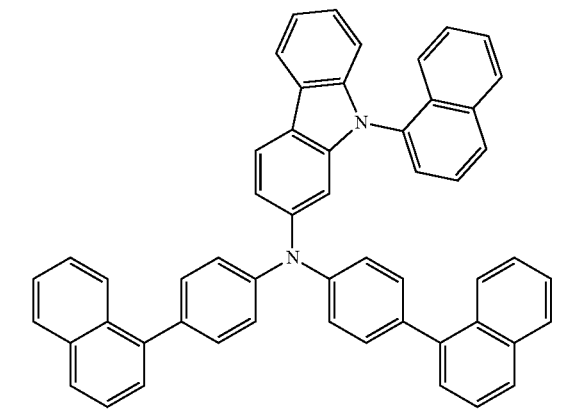
49
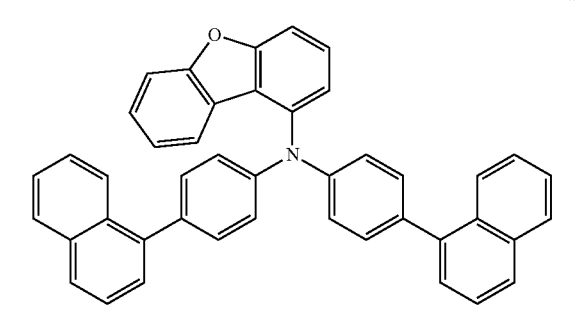
50
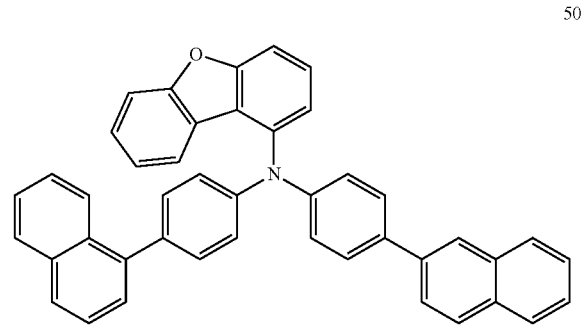
51
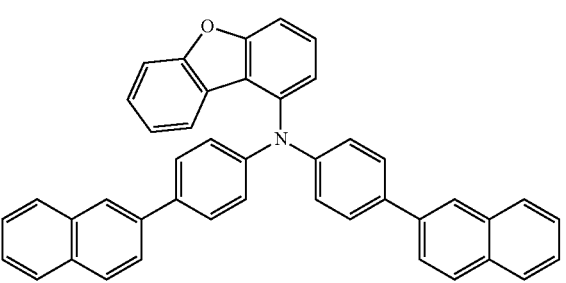
52
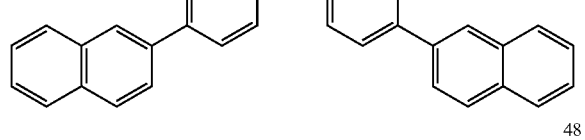
53
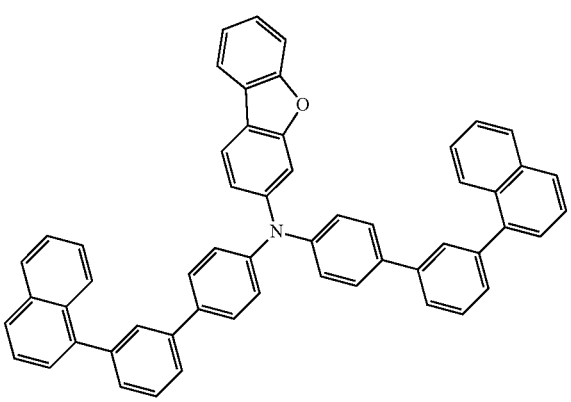
54
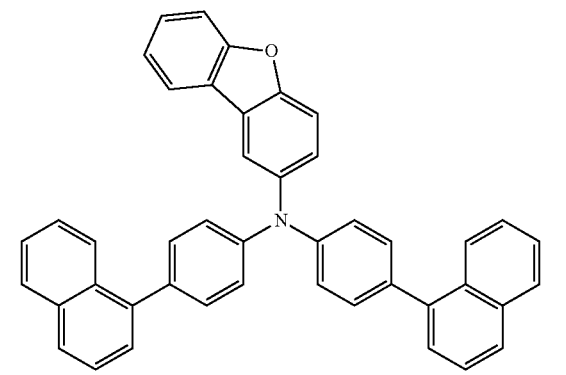

55
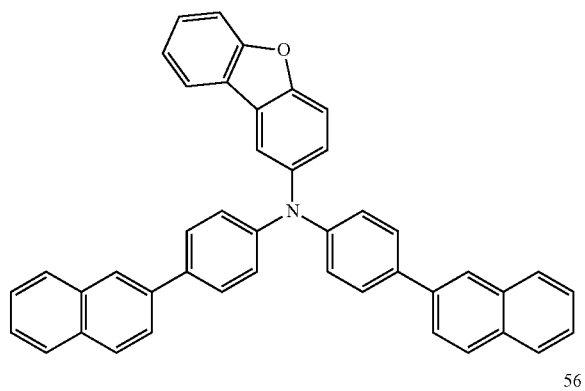
56
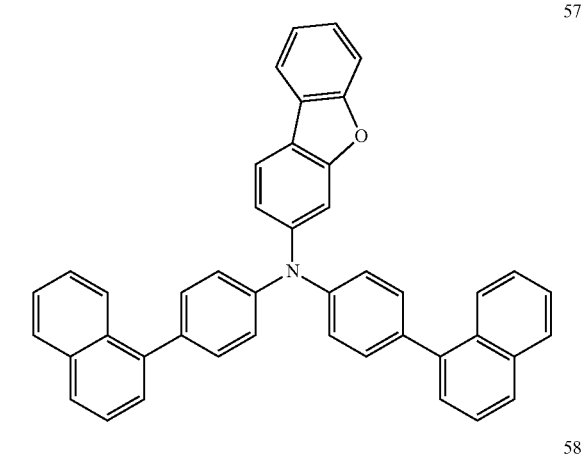
57
58
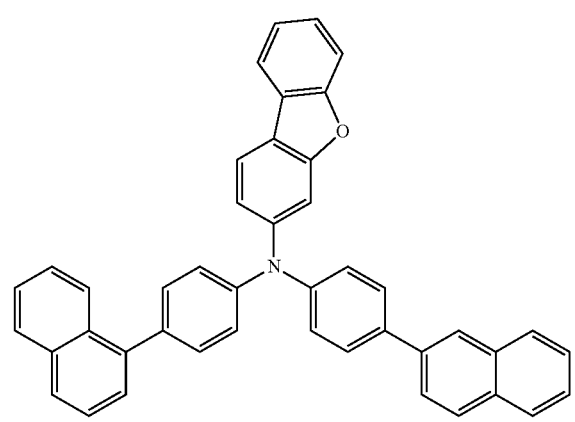
59
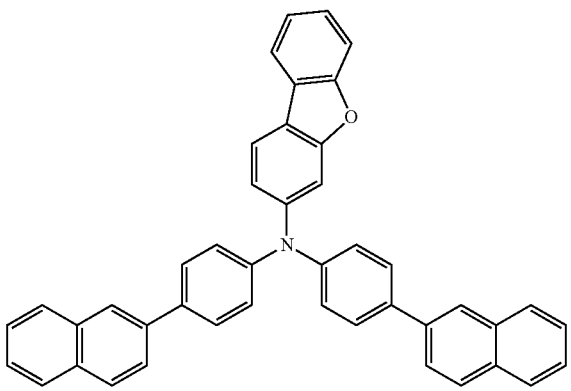
60
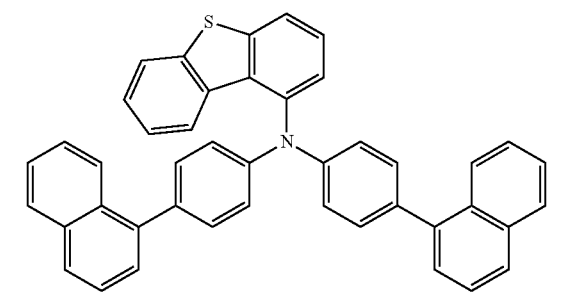
61
62
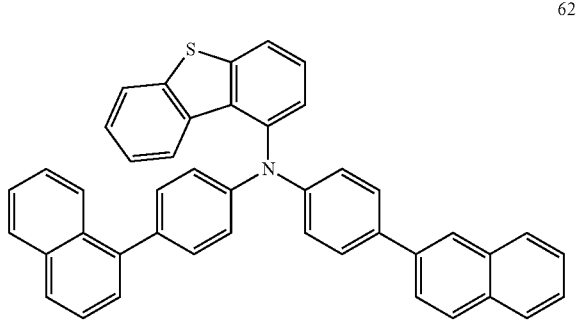

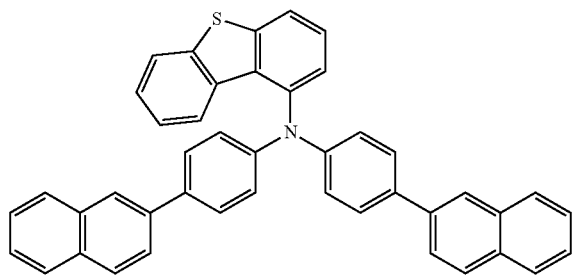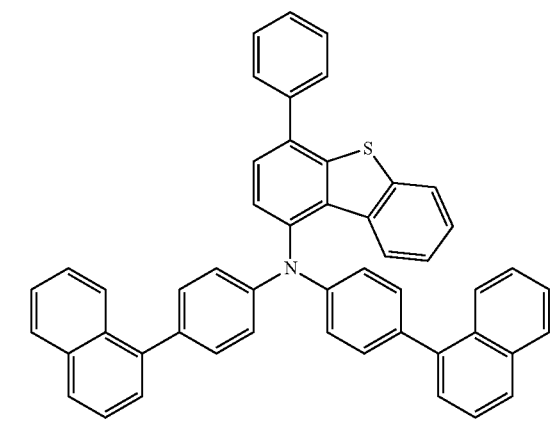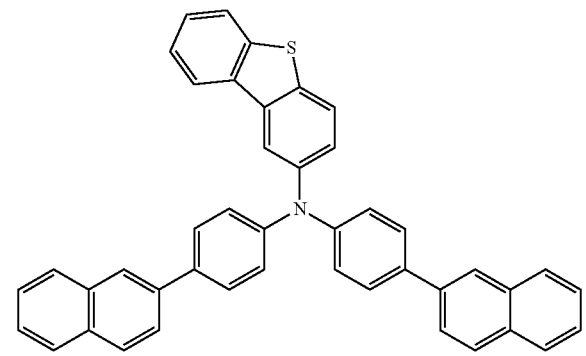

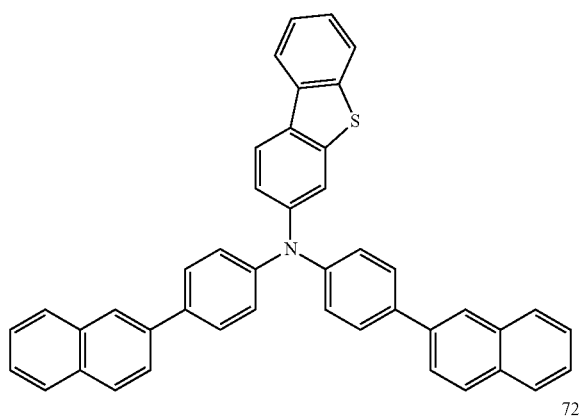
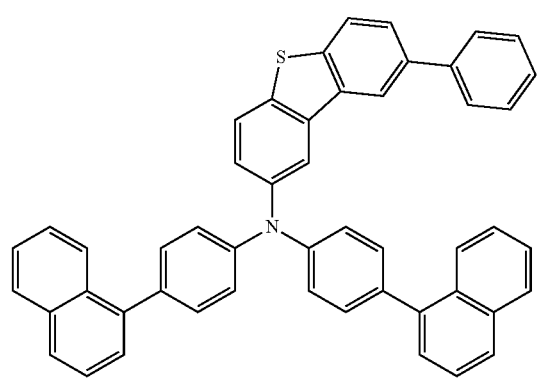
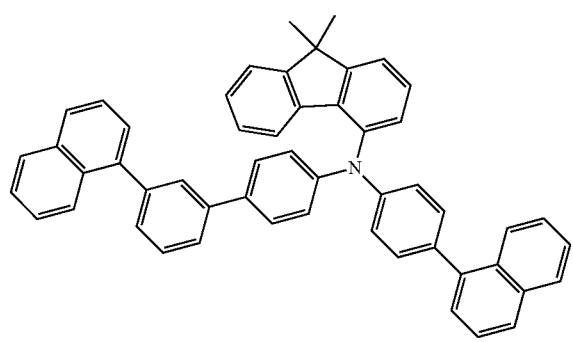
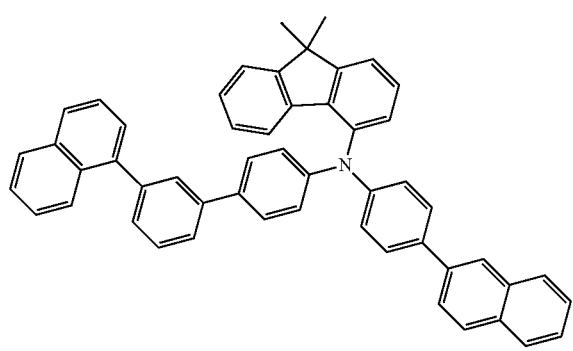
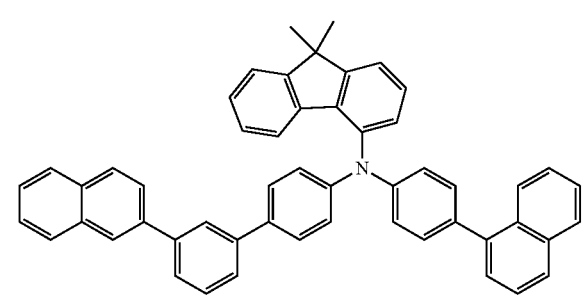
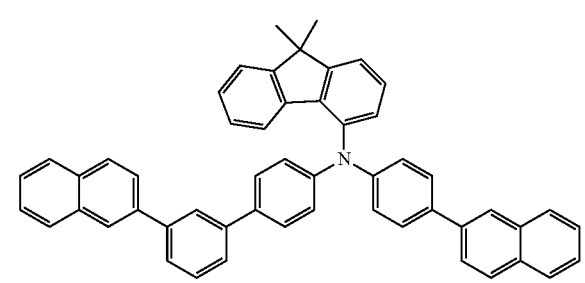
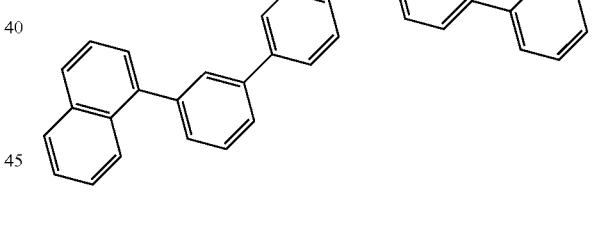
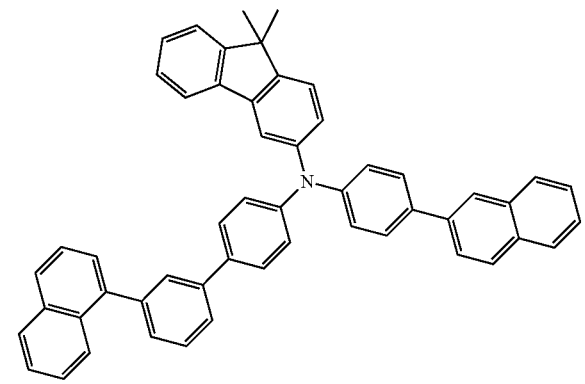

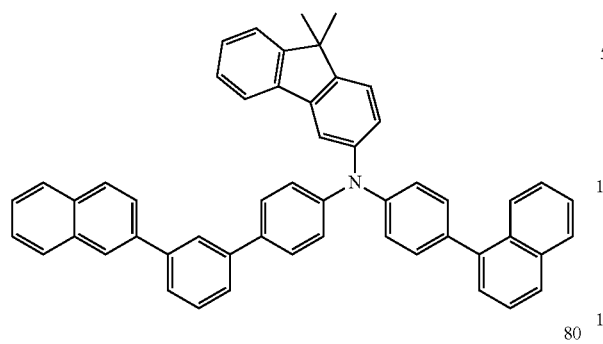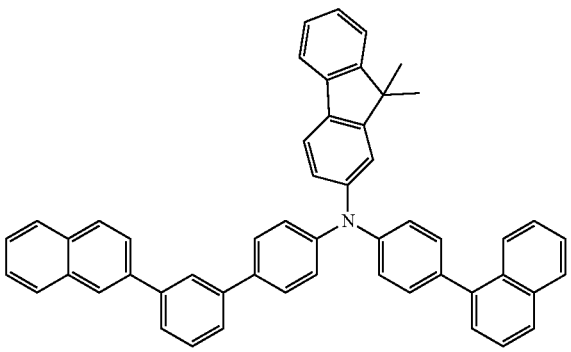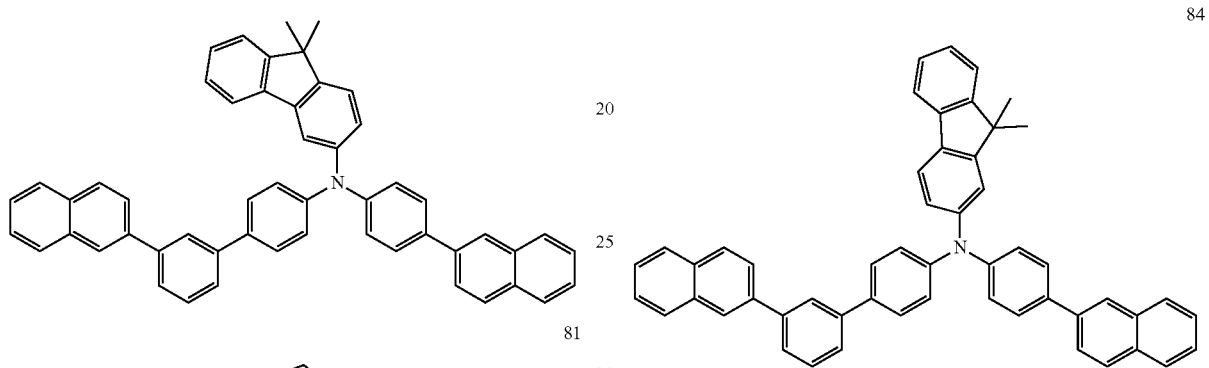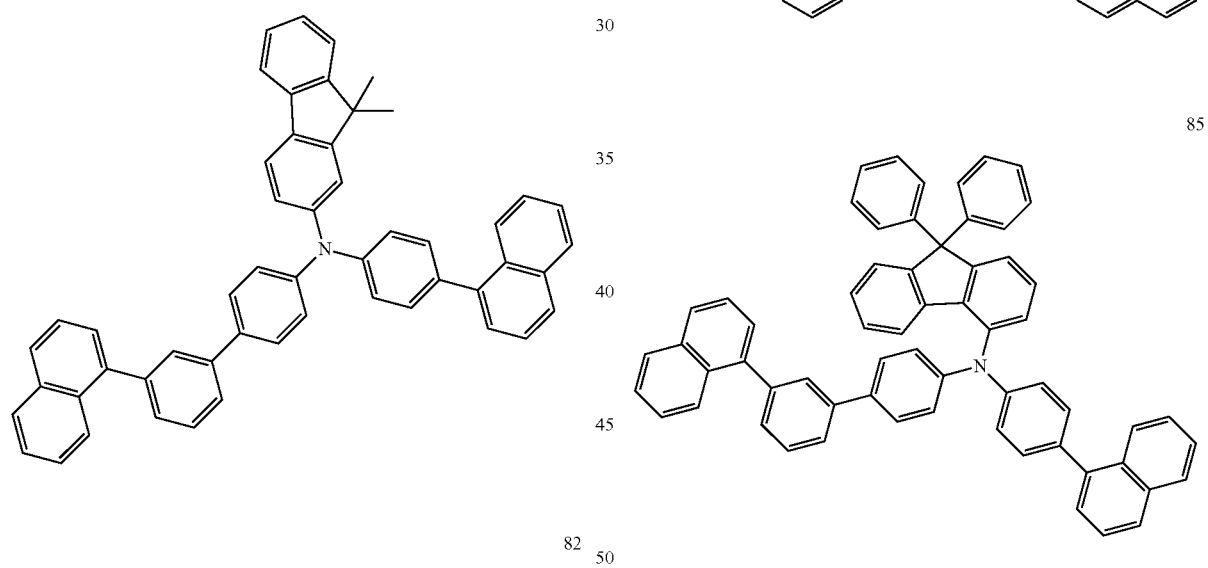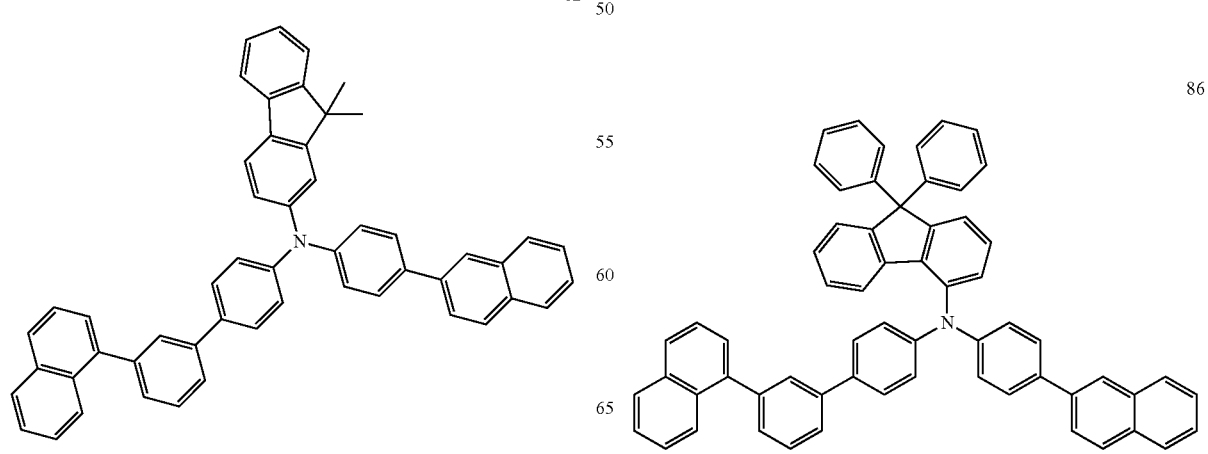

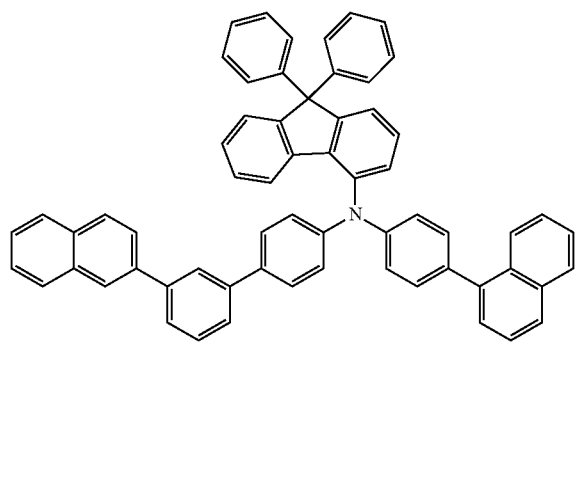
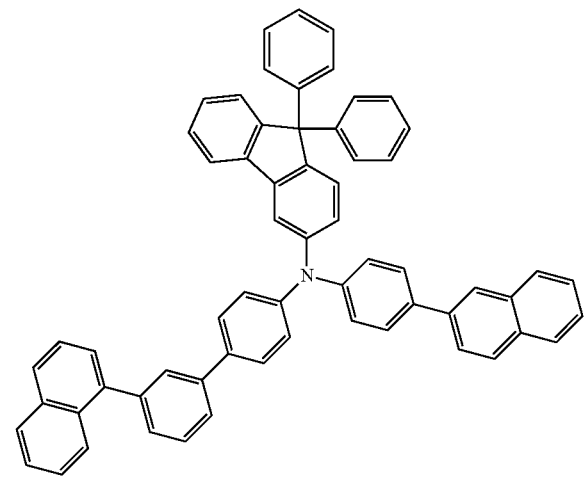
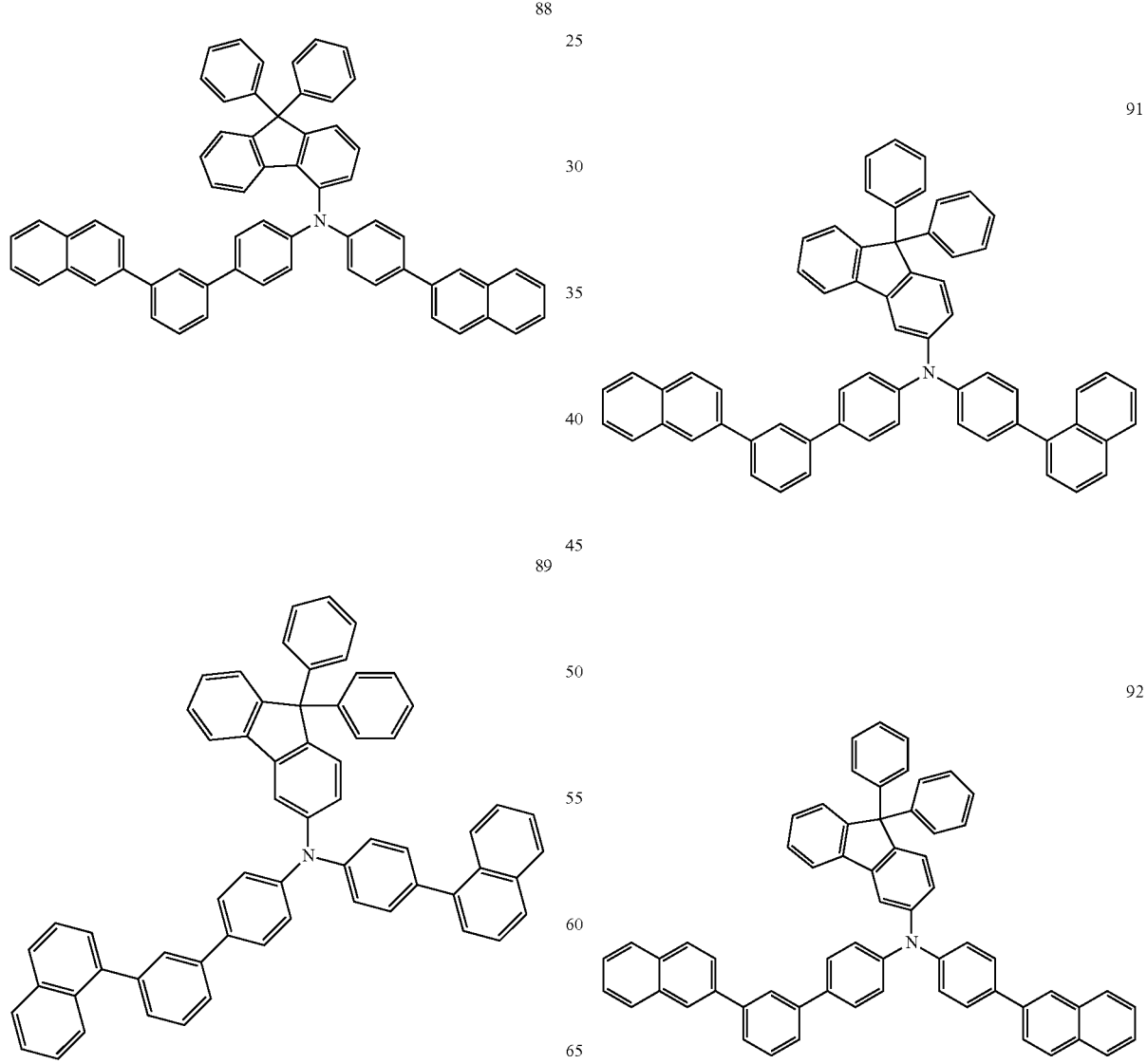

93
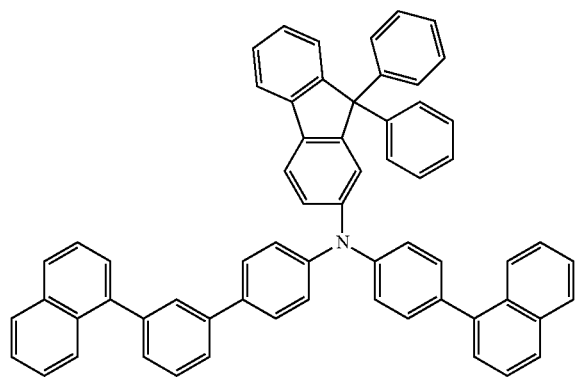
94
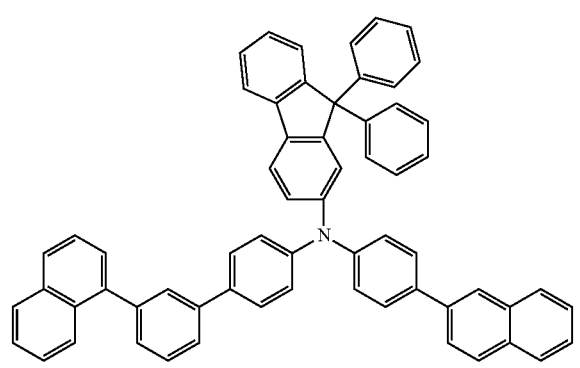
95
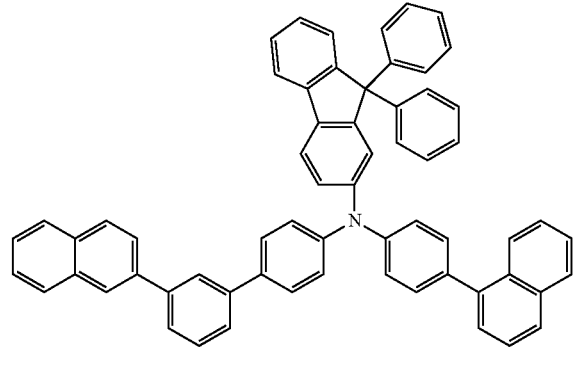
96
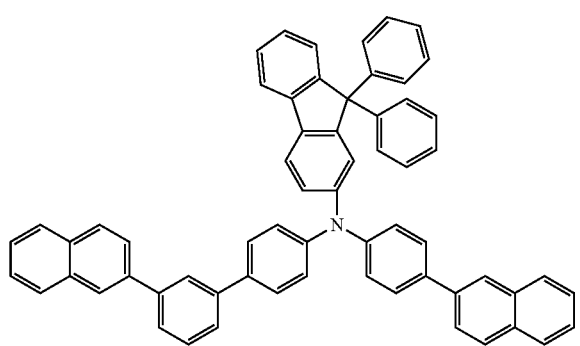
97
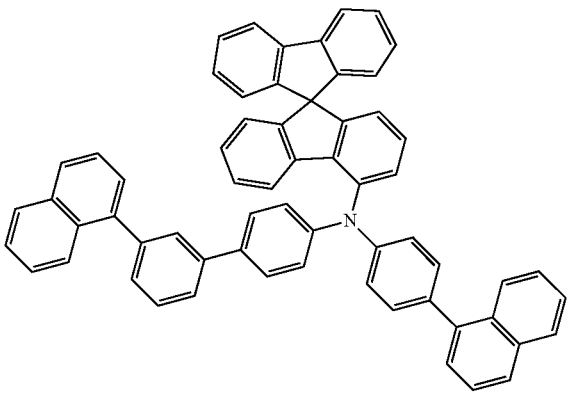
98
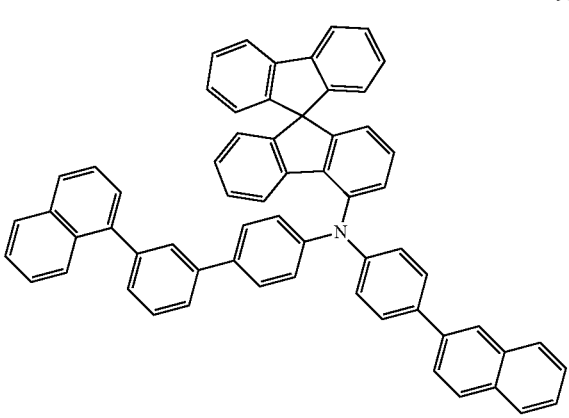
99
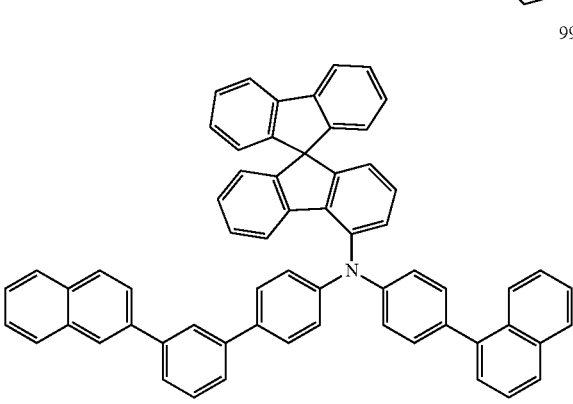
100
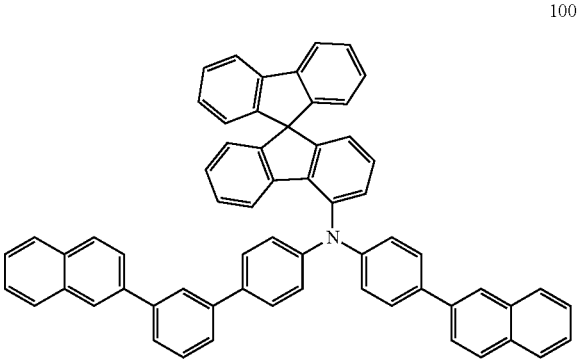

101
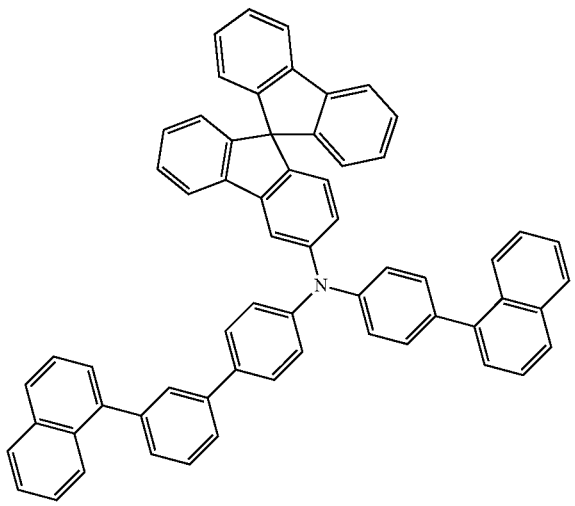
102
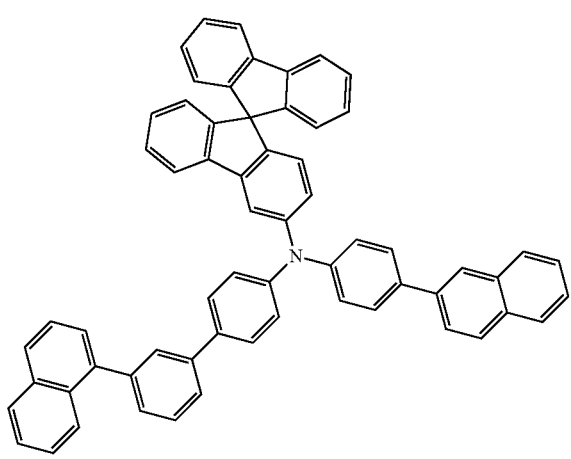
103
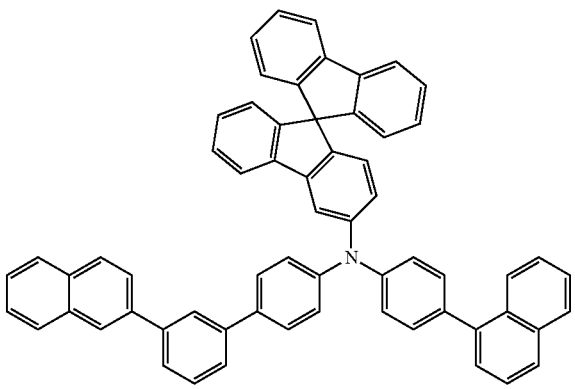
104
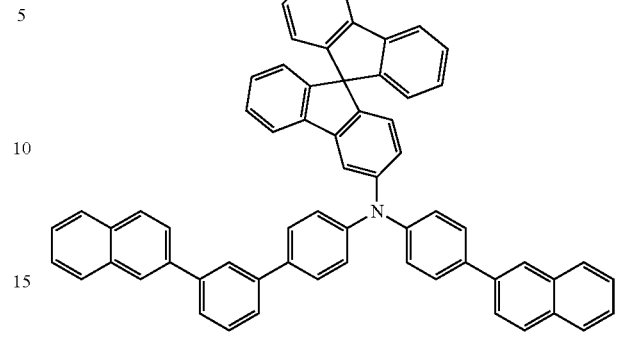
105
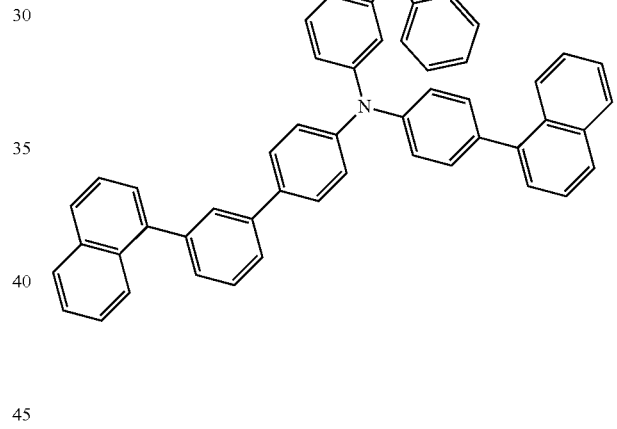
106
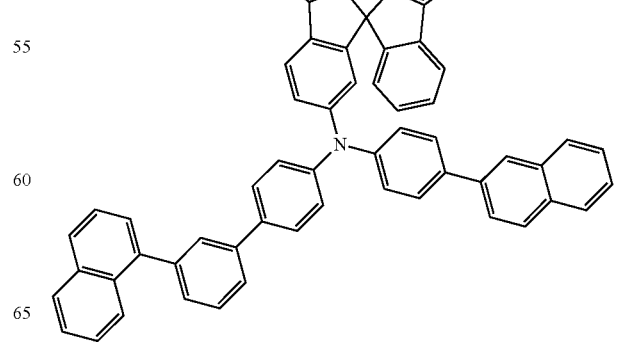

-continued
107
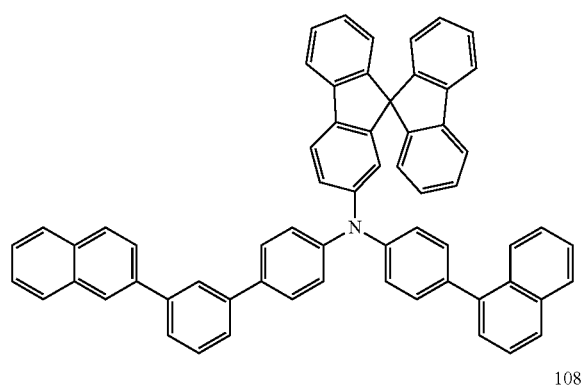
108
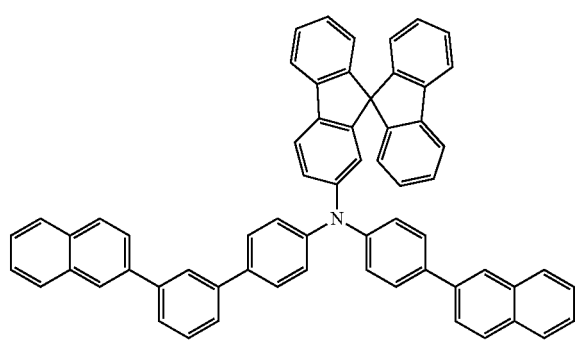
109
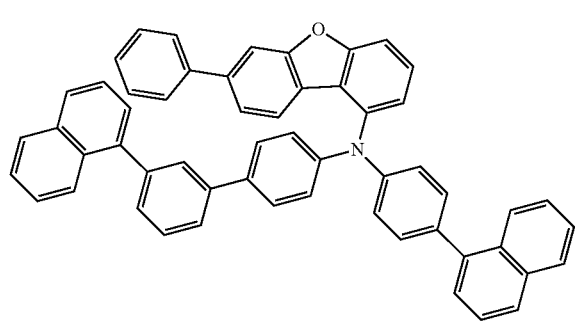
110
-continued
111
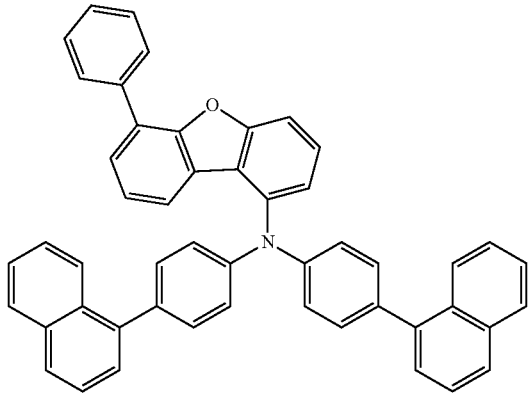
112
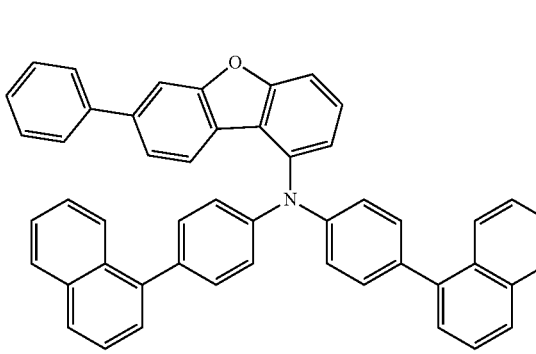
113
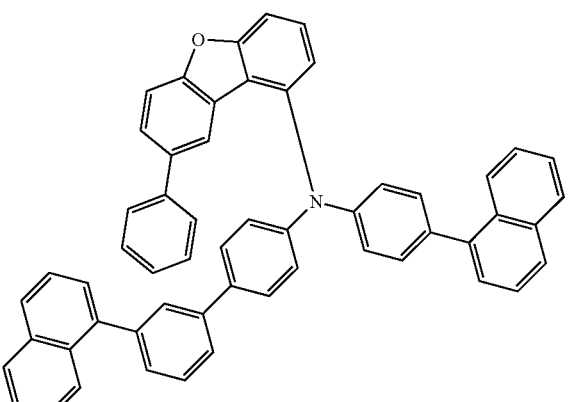
114
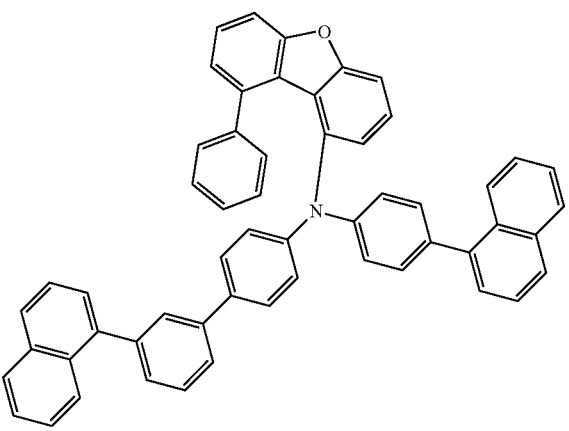

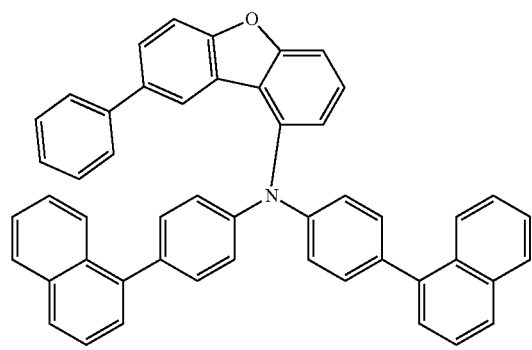
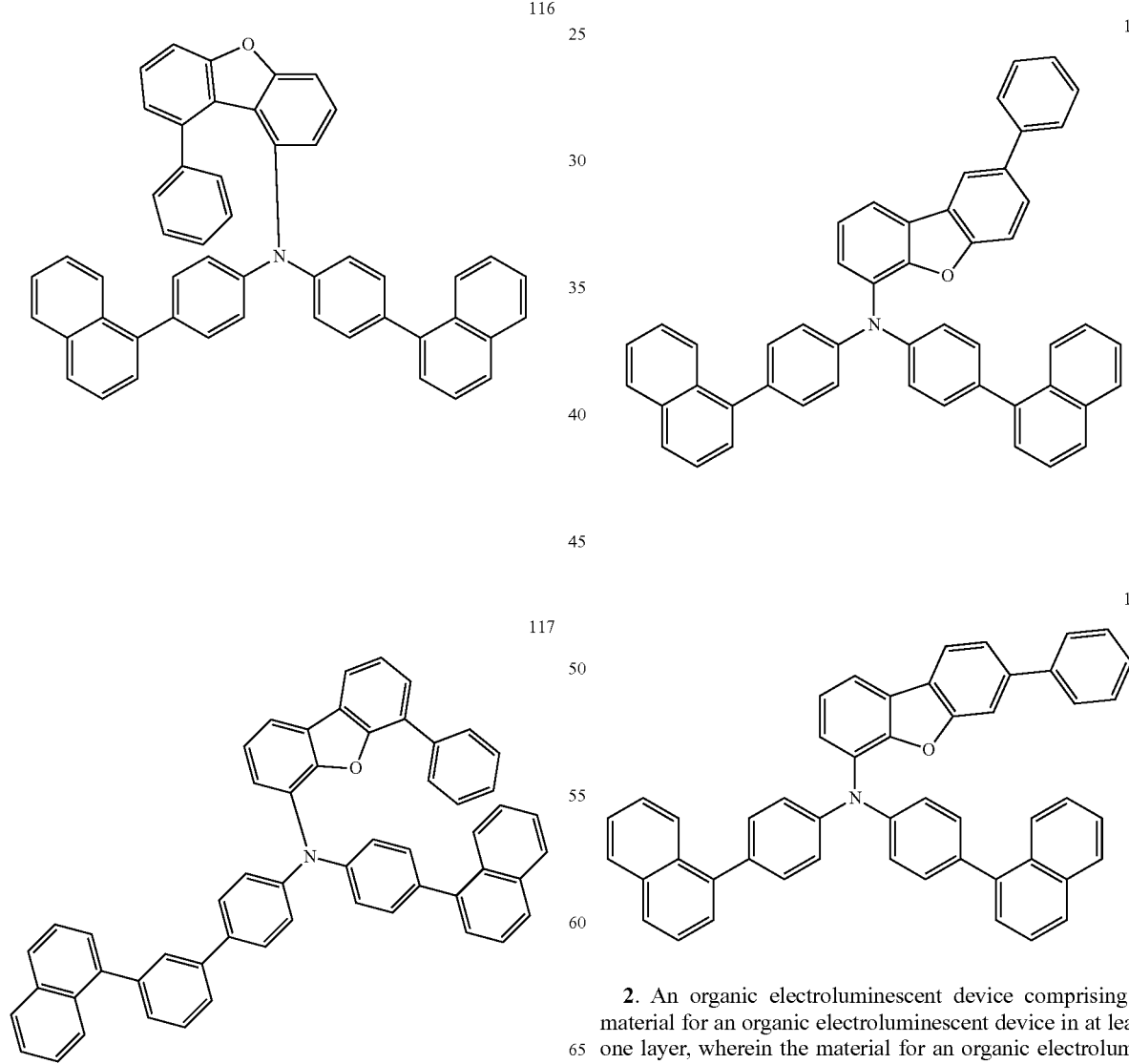
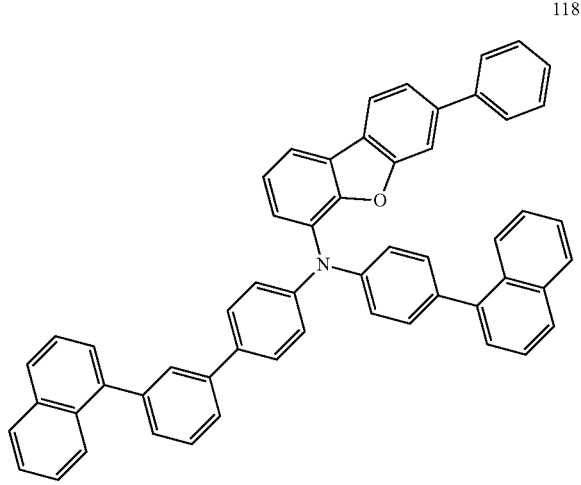
2. An organic electroluminescent device comprising a material for an organic electroluminescent device in at least one layer, wherein the material for an organic electroluminescent device is represented by one of Compounds 1 to 120 (collectively denoted as Formula 3):

1
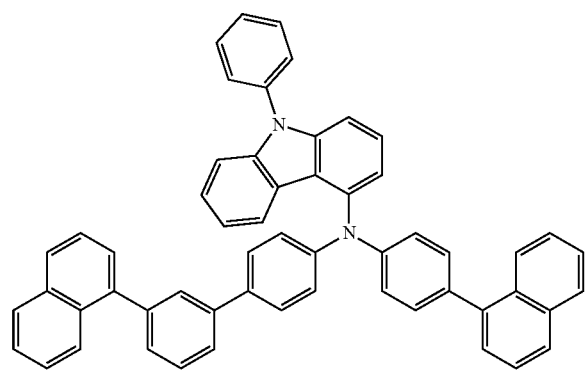
2
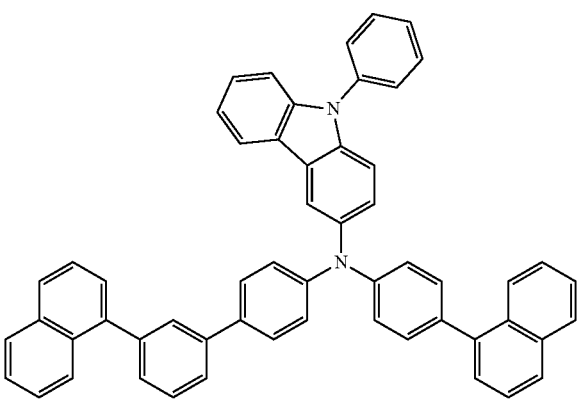
3
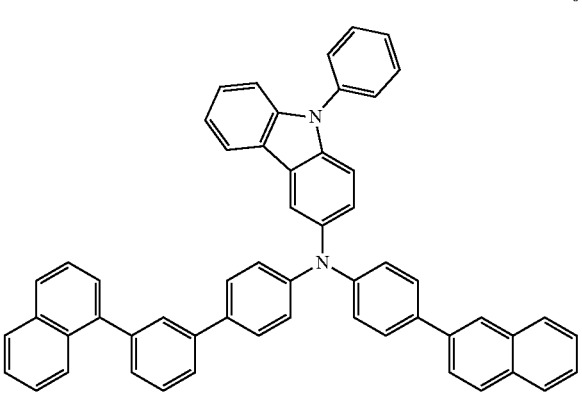
4
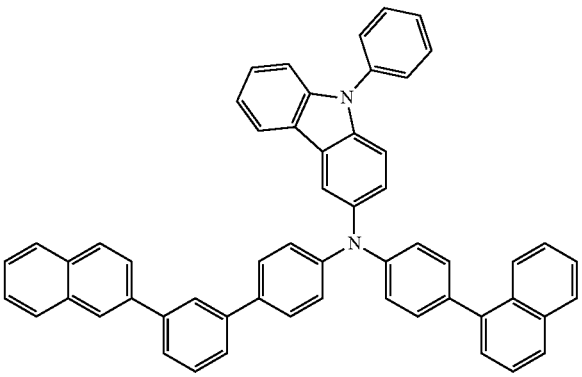
5
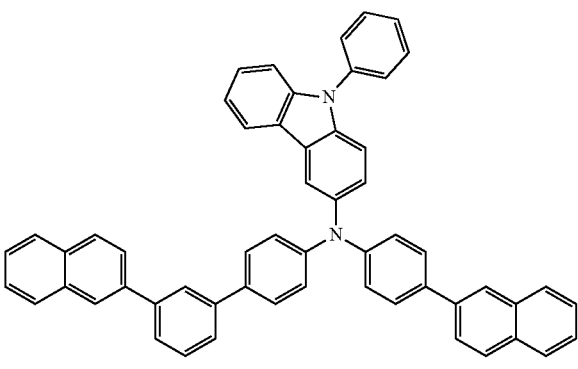

9
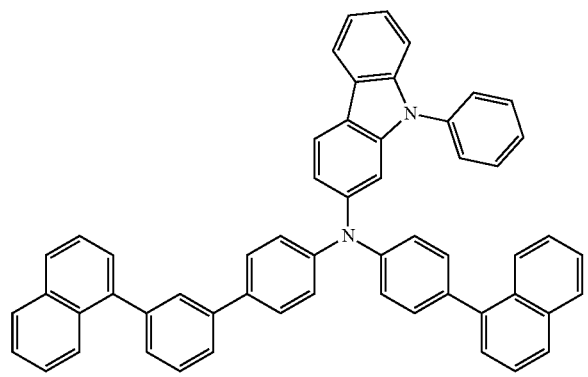
10
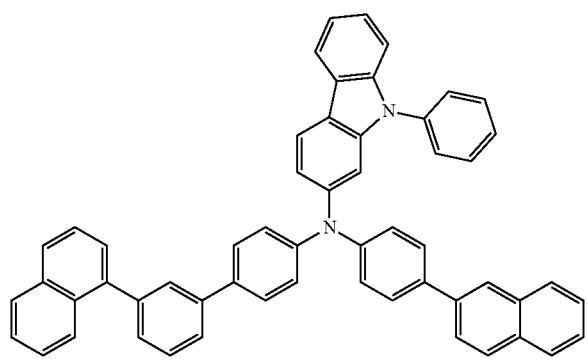
11
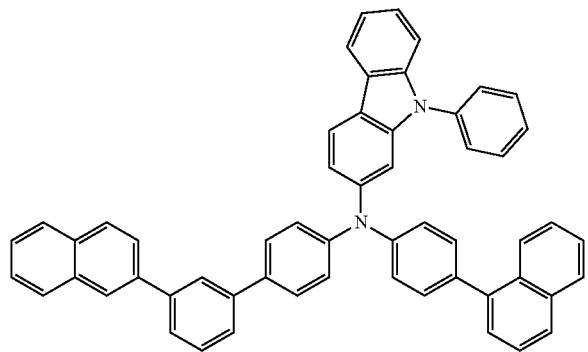
12
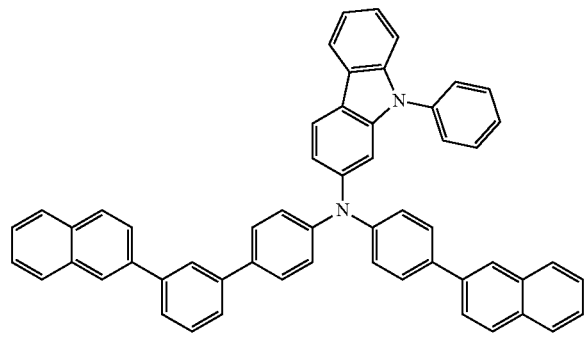
13
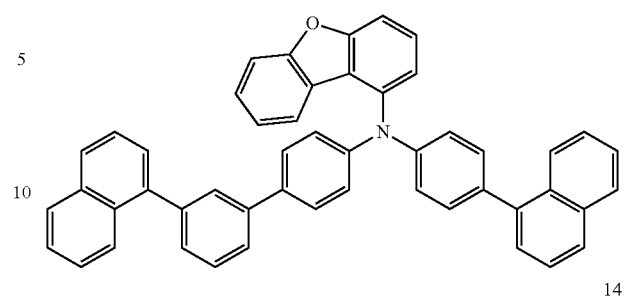
14
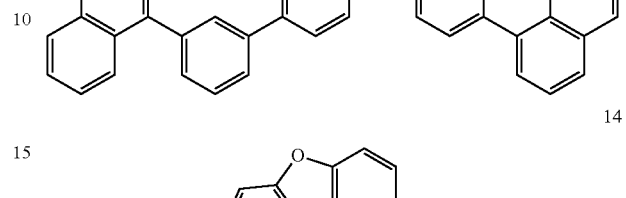
15
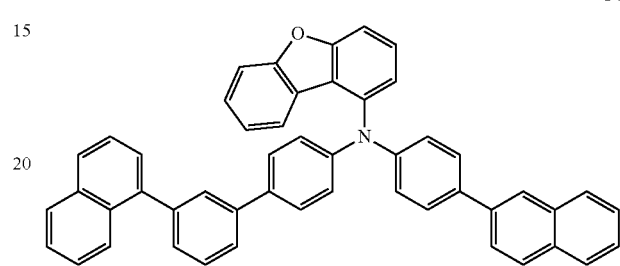
16
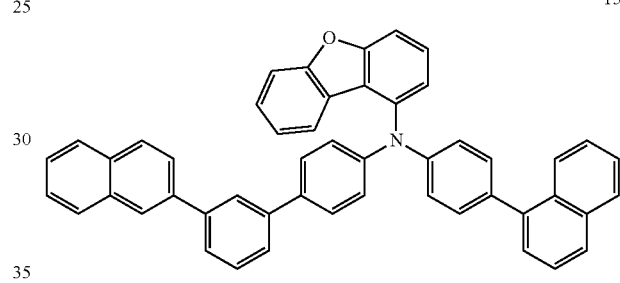
17
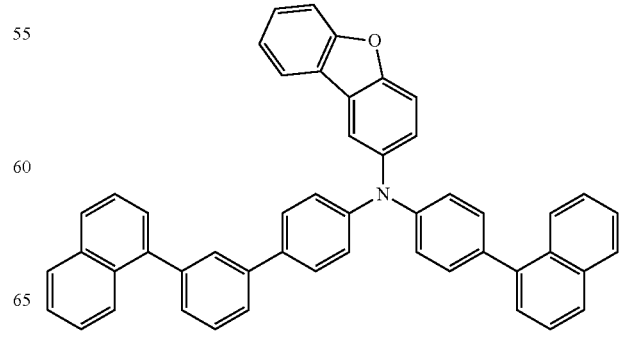

18
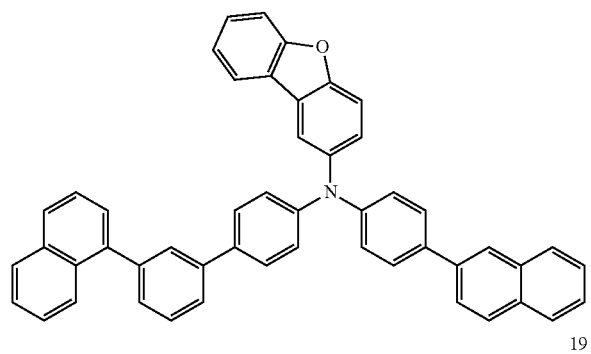
19
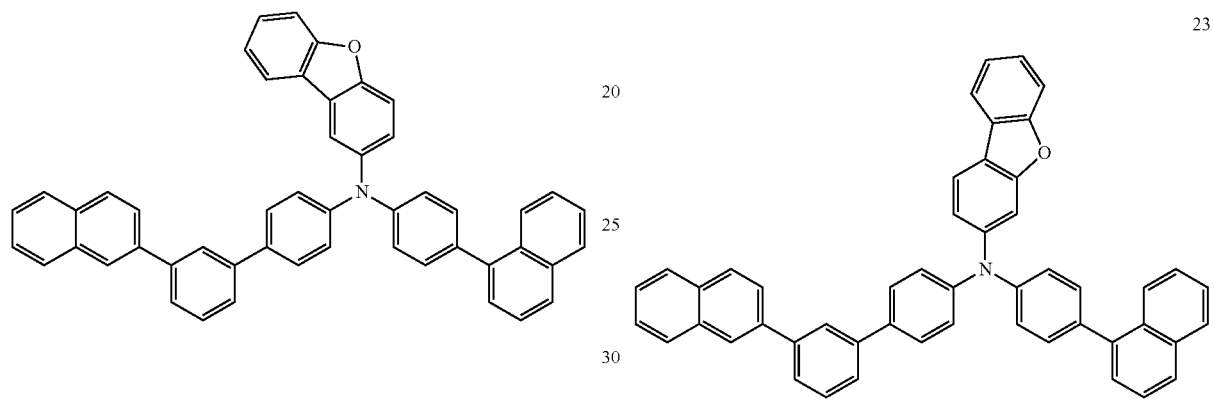
20
22
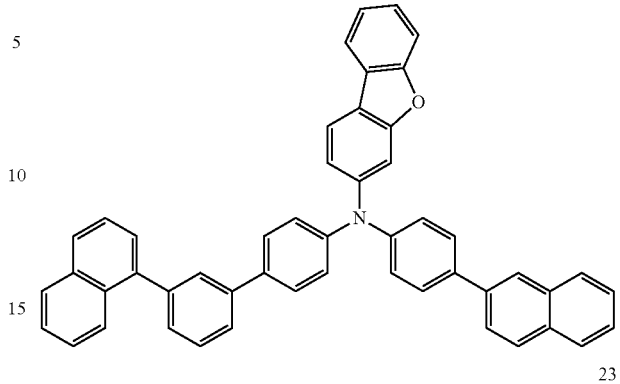
23
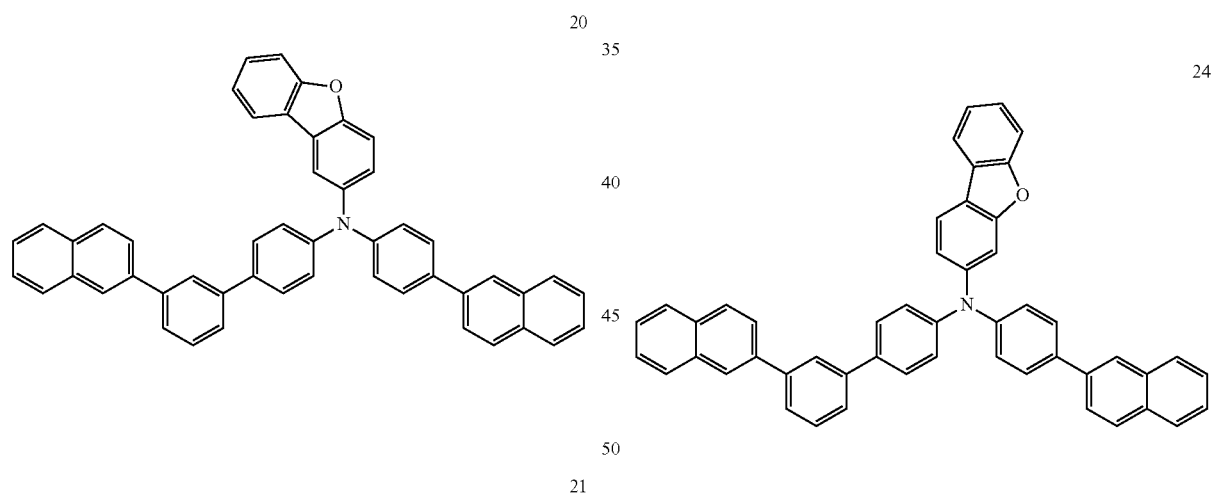
24
21
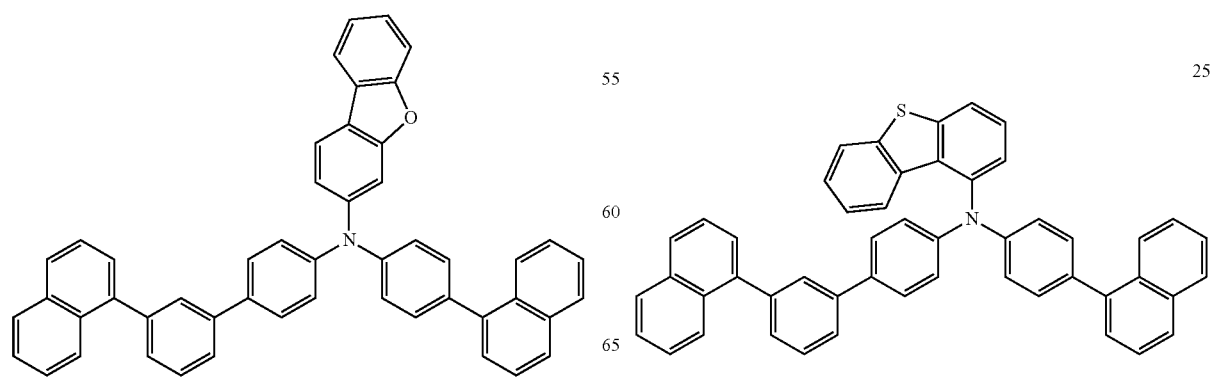
25

26
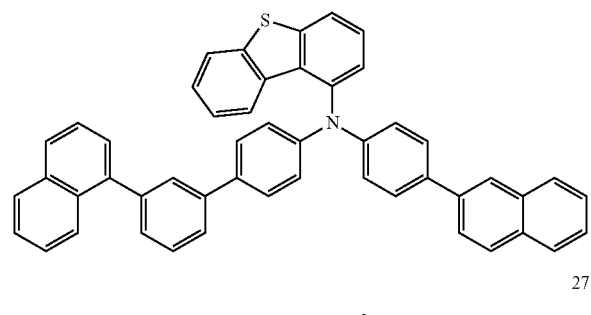
27
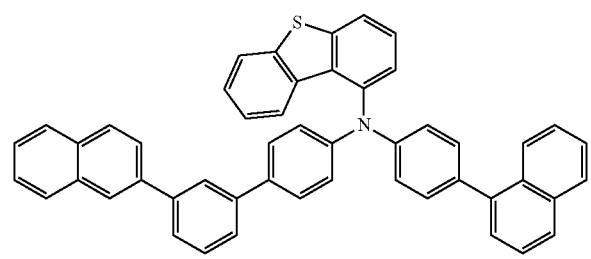
28
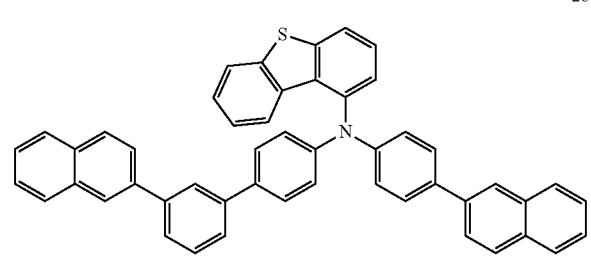
29
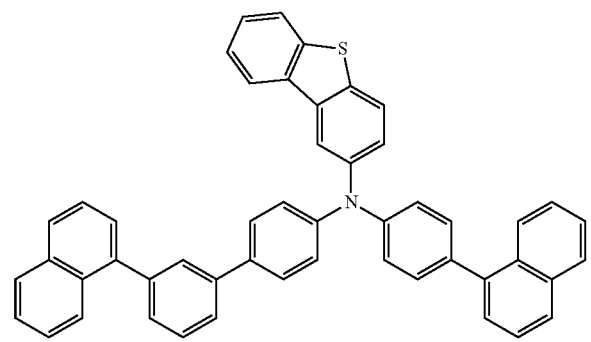
30
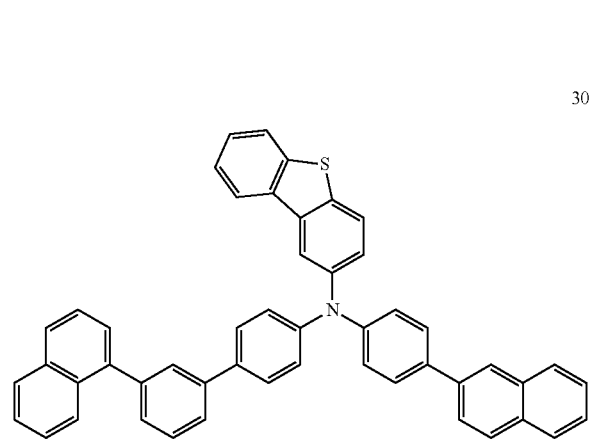
31
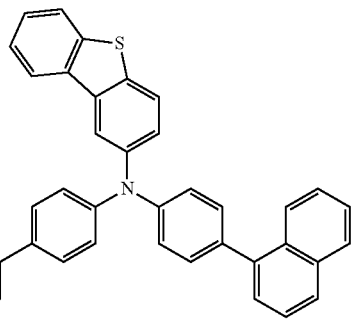
32
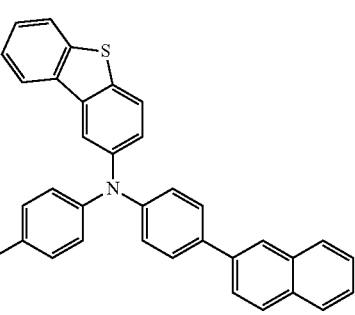
33
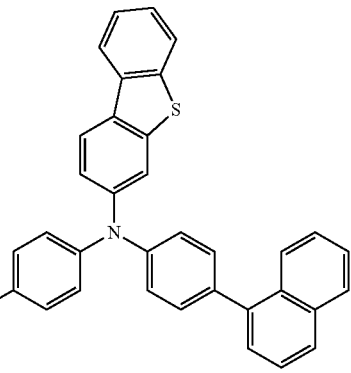
34
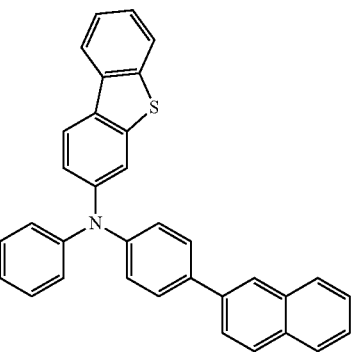

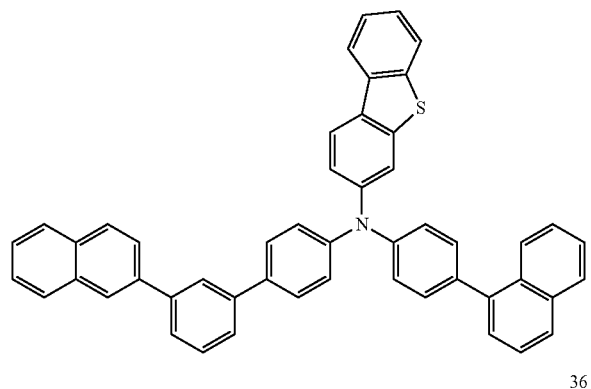
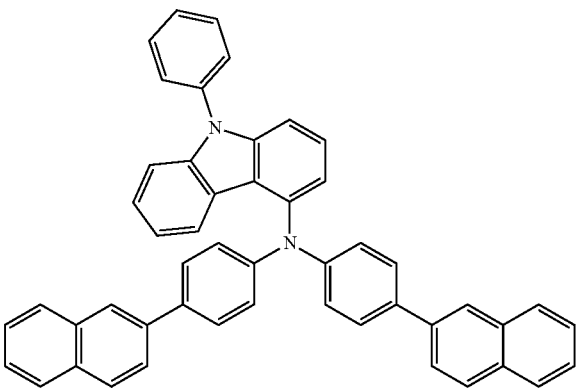
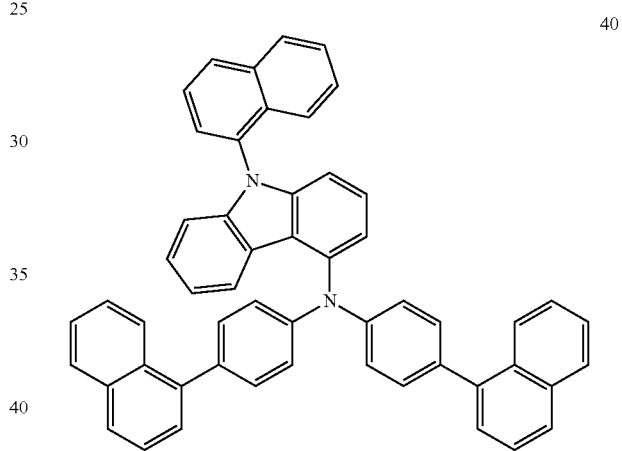
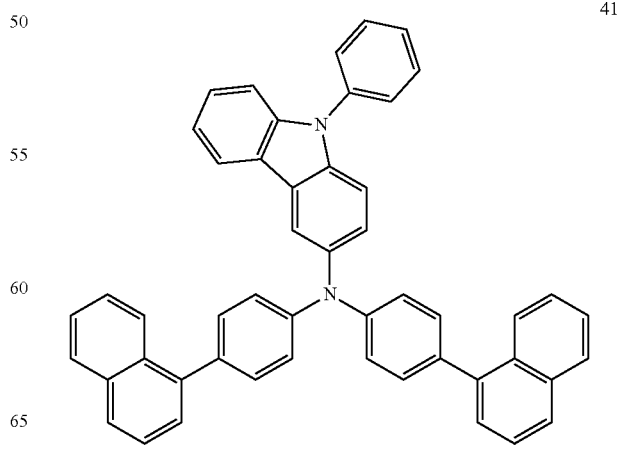

42
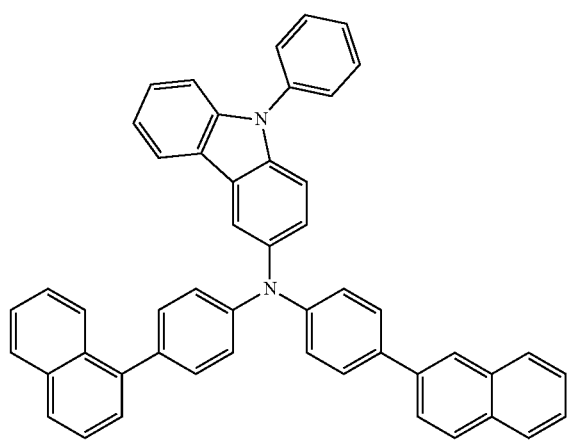
43
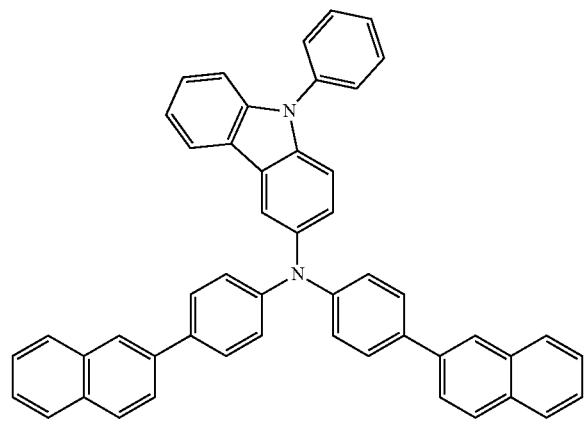
44
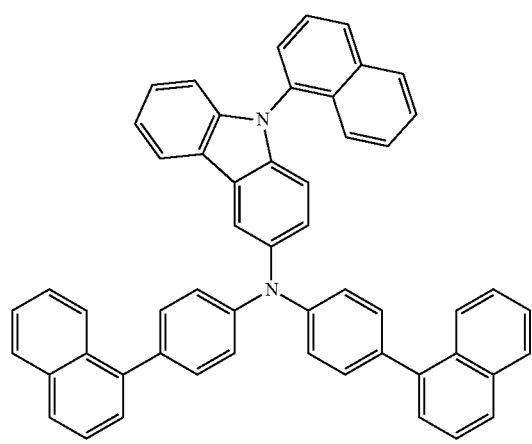
45
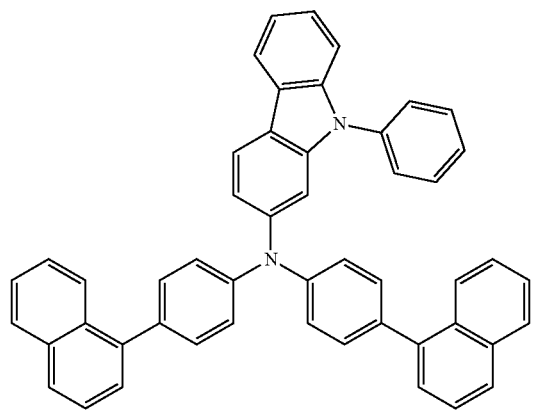
46
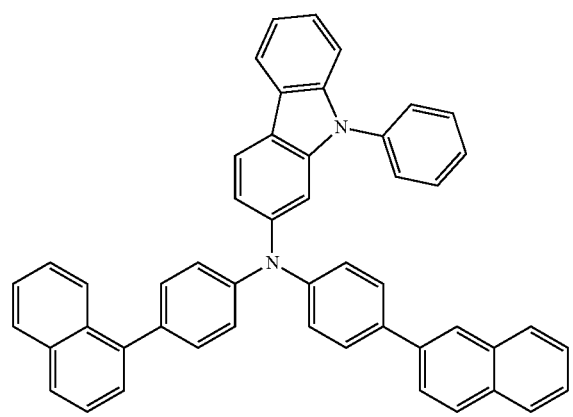
47
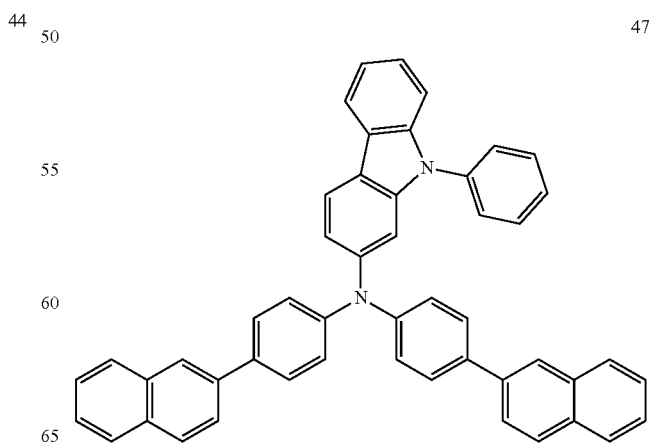

48
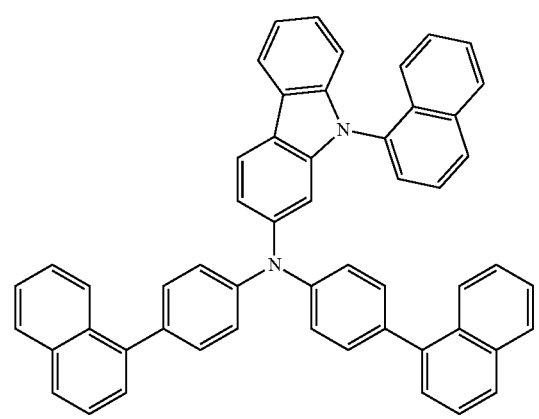
49
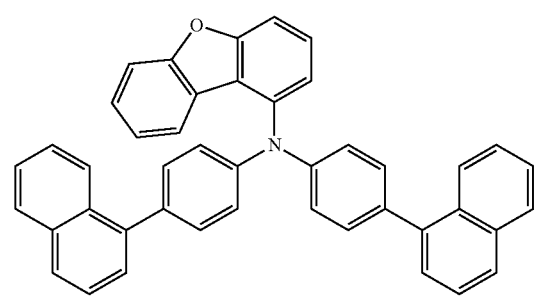
50
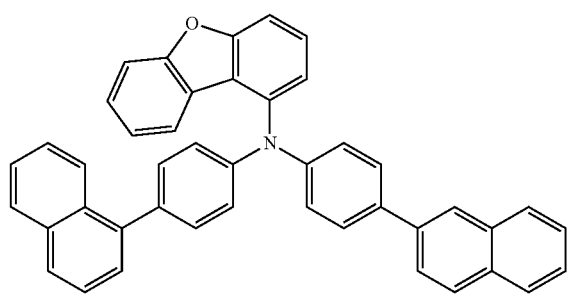
51
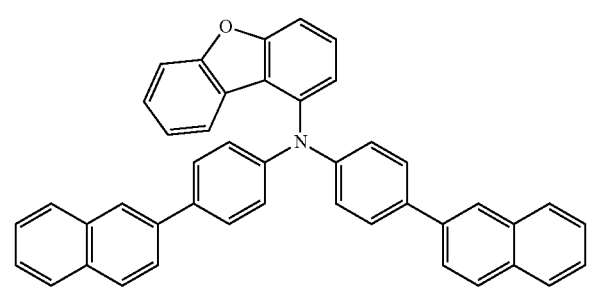
52
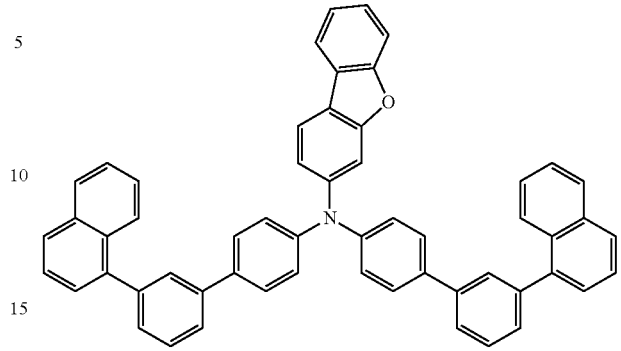
53
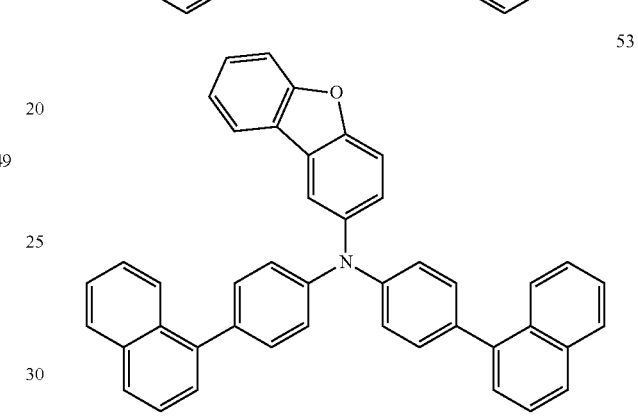
54
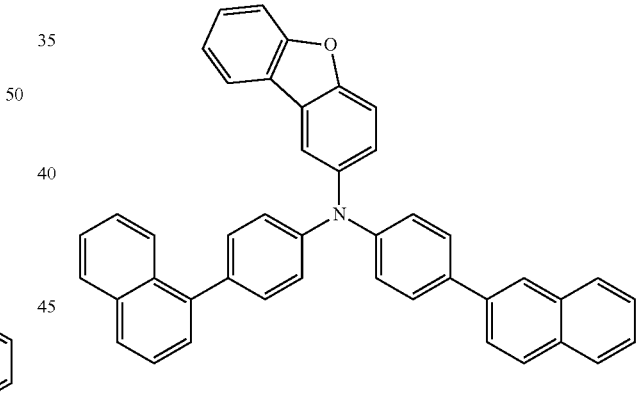
55
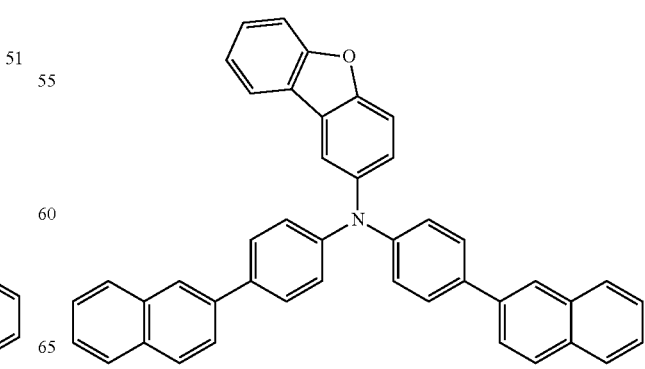

-continued

56

57

58

59

-continued

60

61

62

63

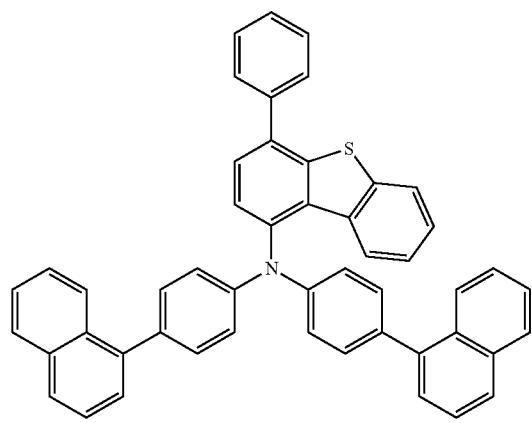
64
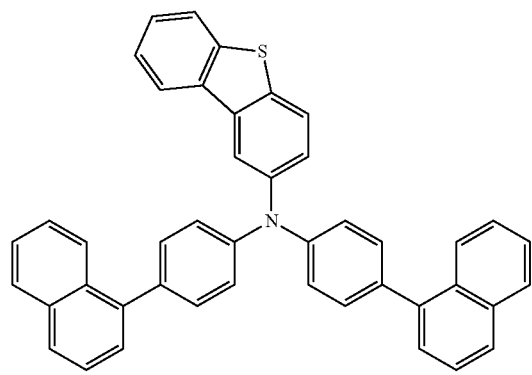
65
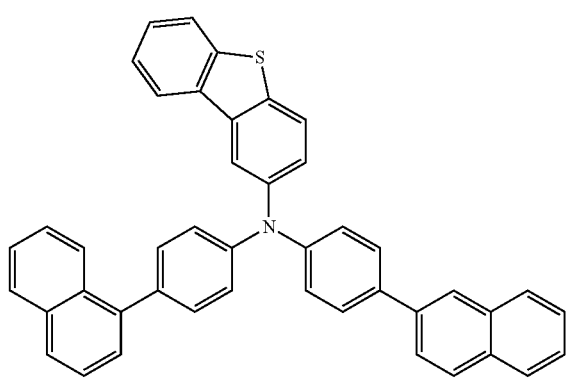
66
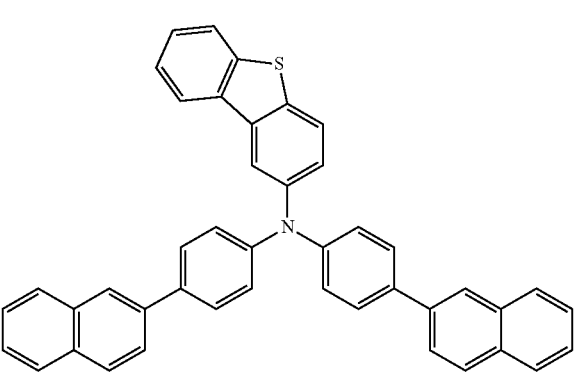
67
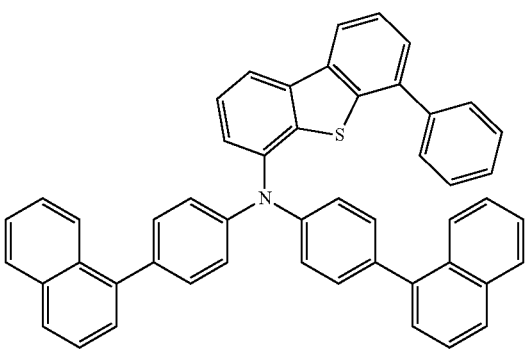
68
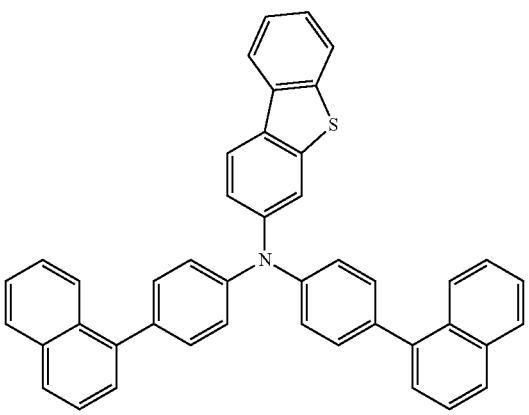
69
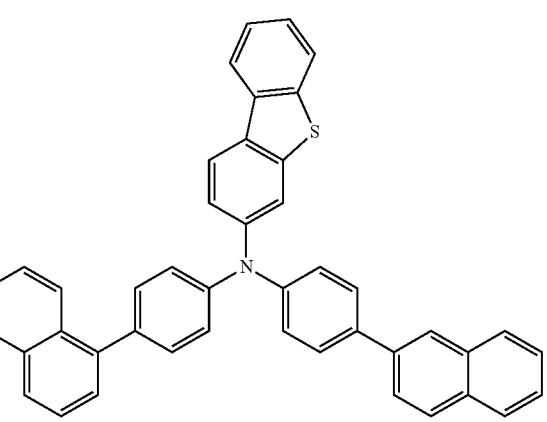
70
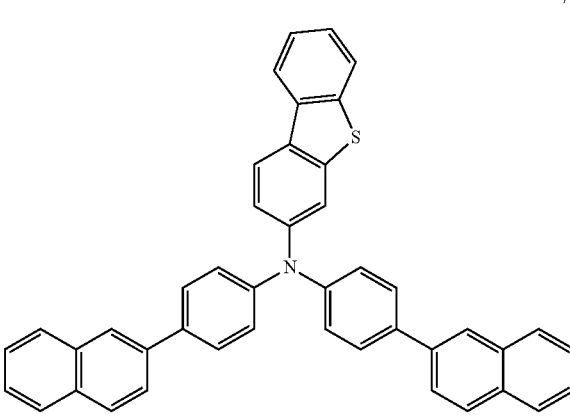
71

72
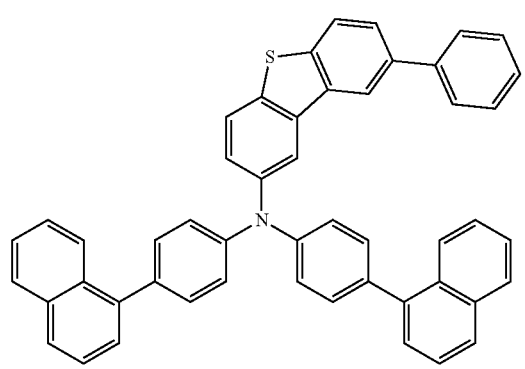
73
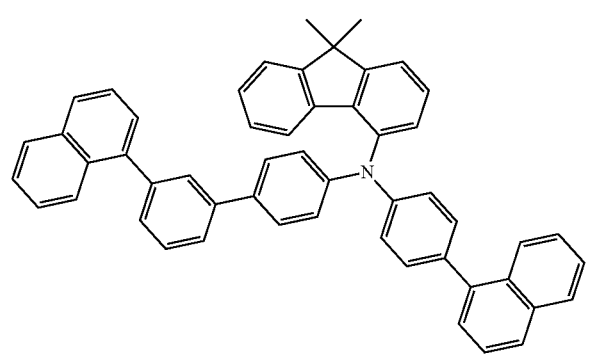
74
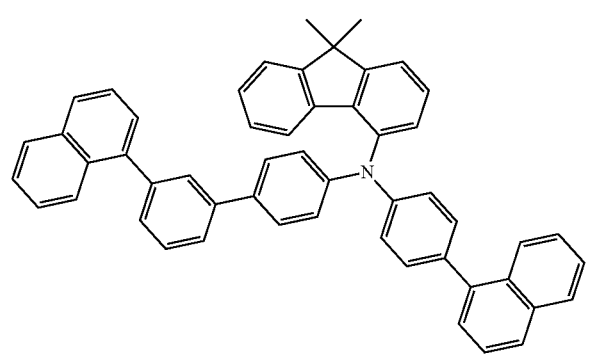
75
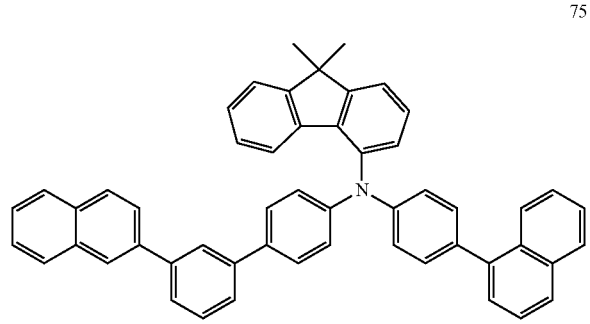
76
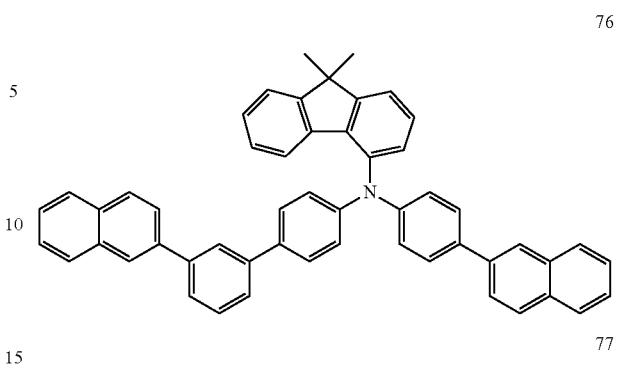
77
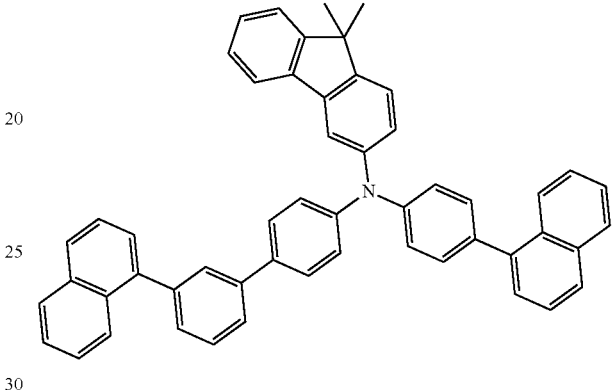
78
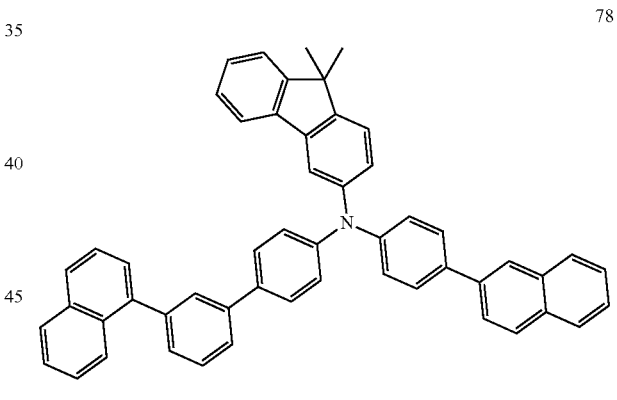
79
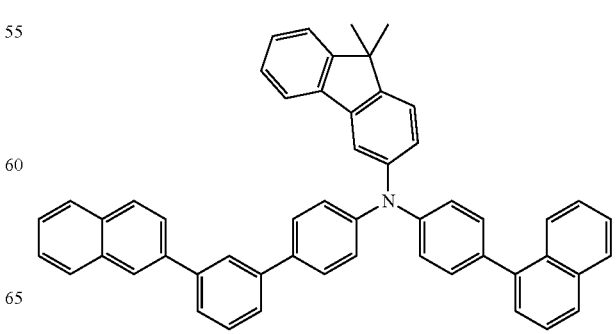

109
-continued
80
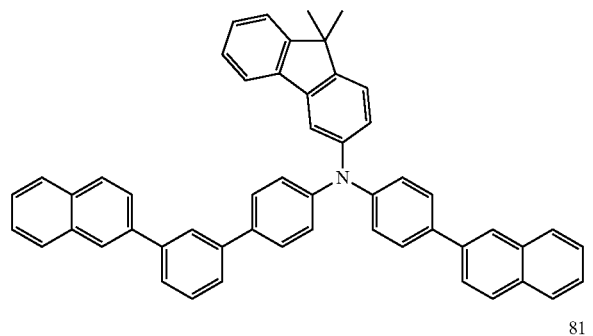
81
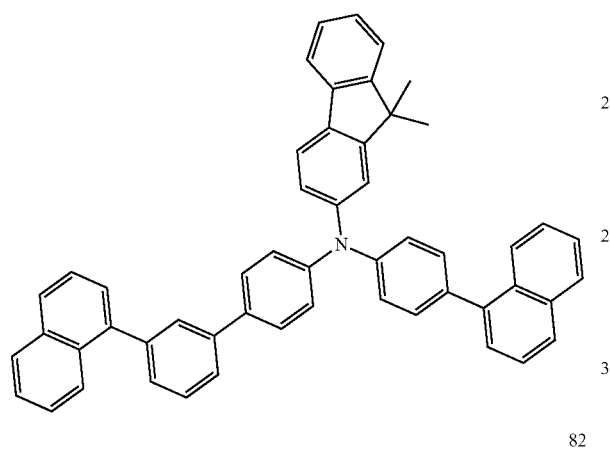
82
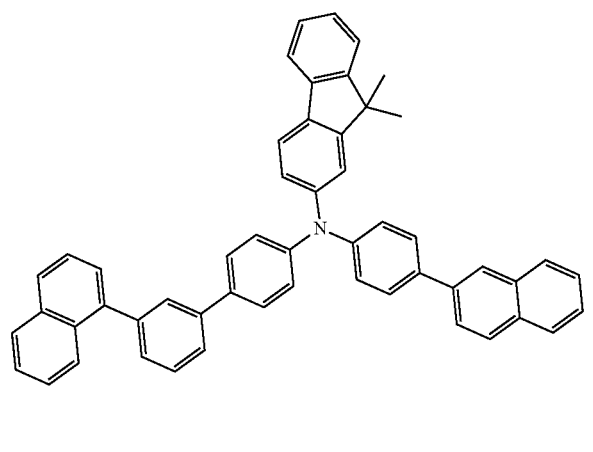
83
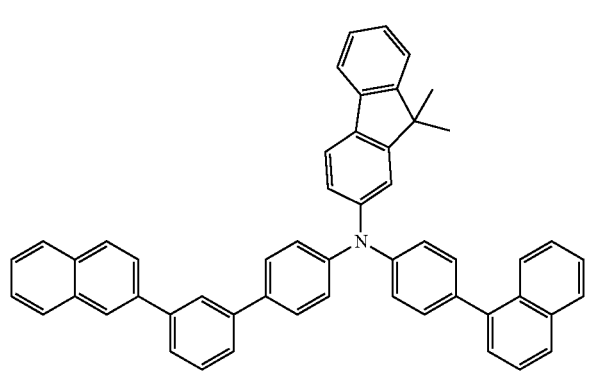
110
-continued
84
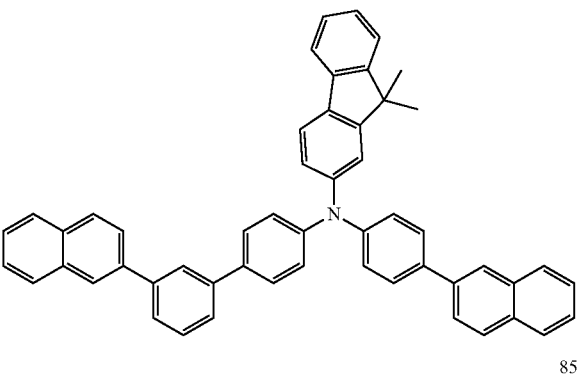
85
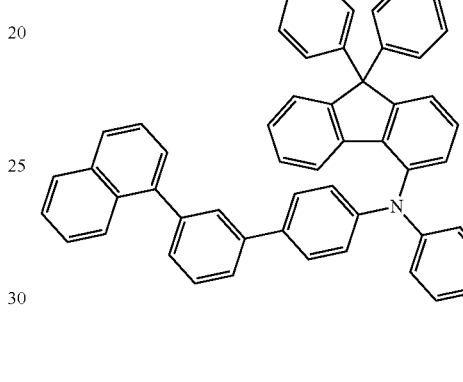
86
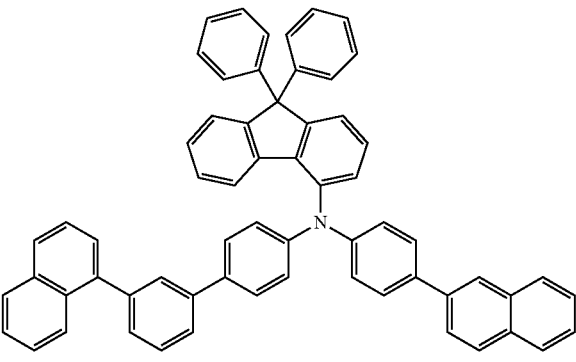
87
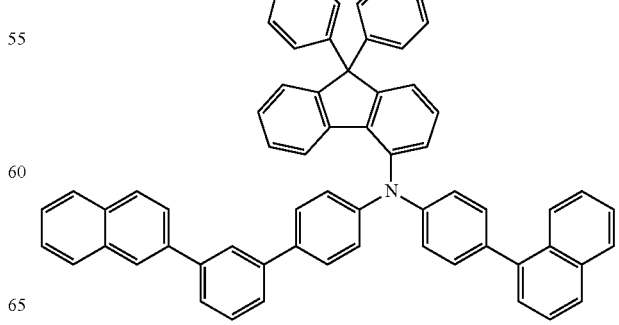

-continued
88
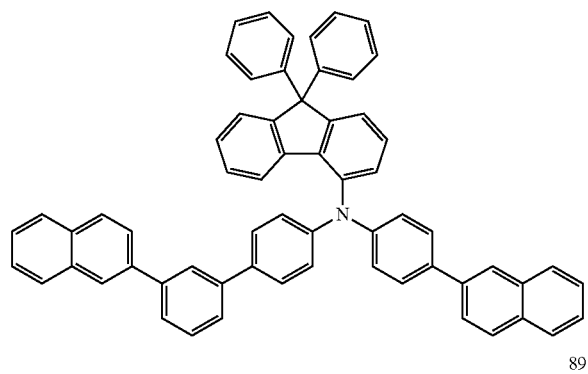
89
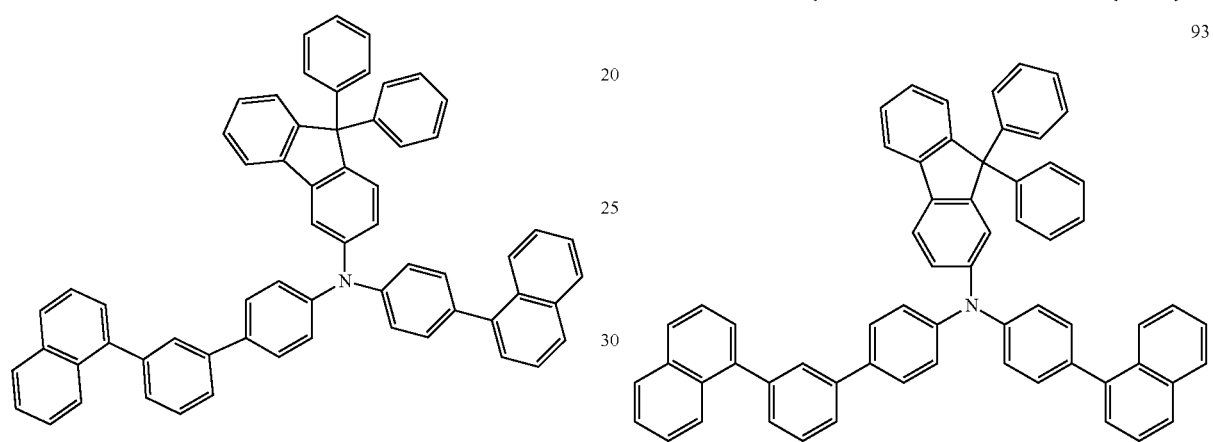
90
91
-continued
92
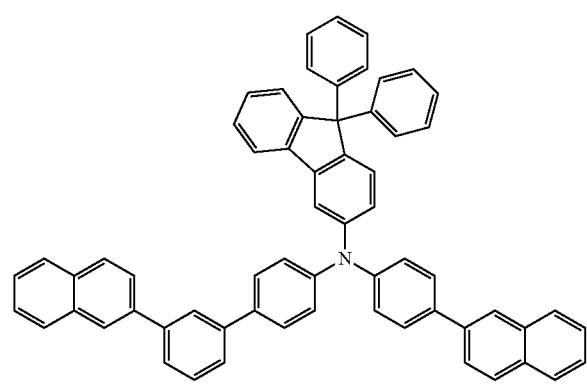
93
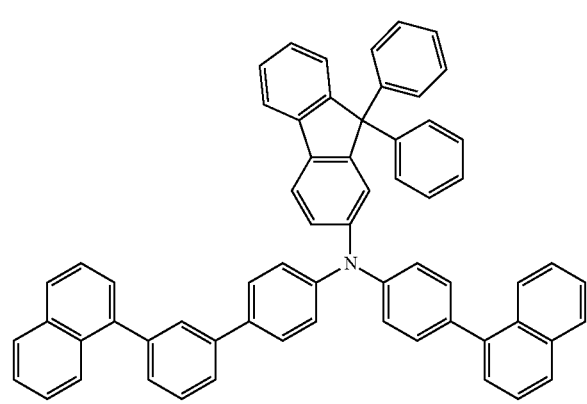
94
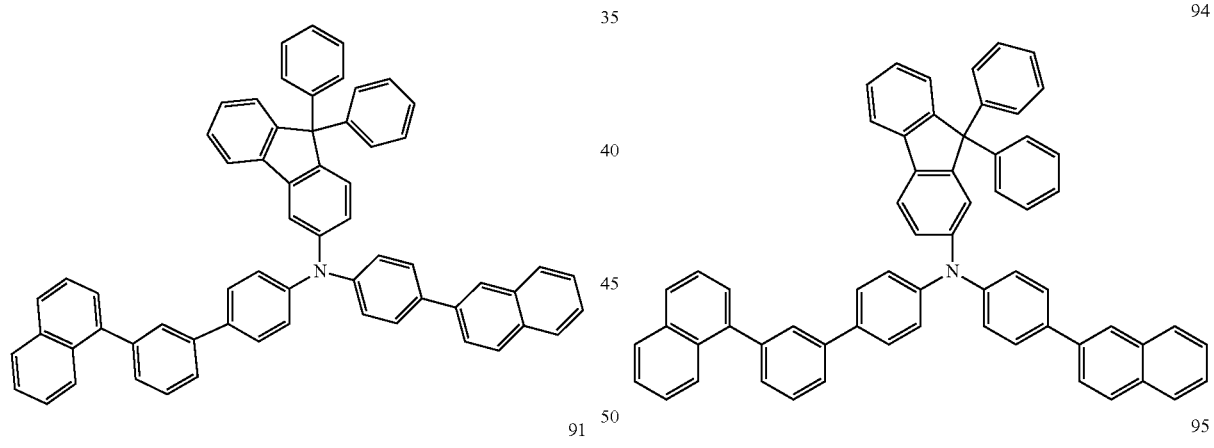
95
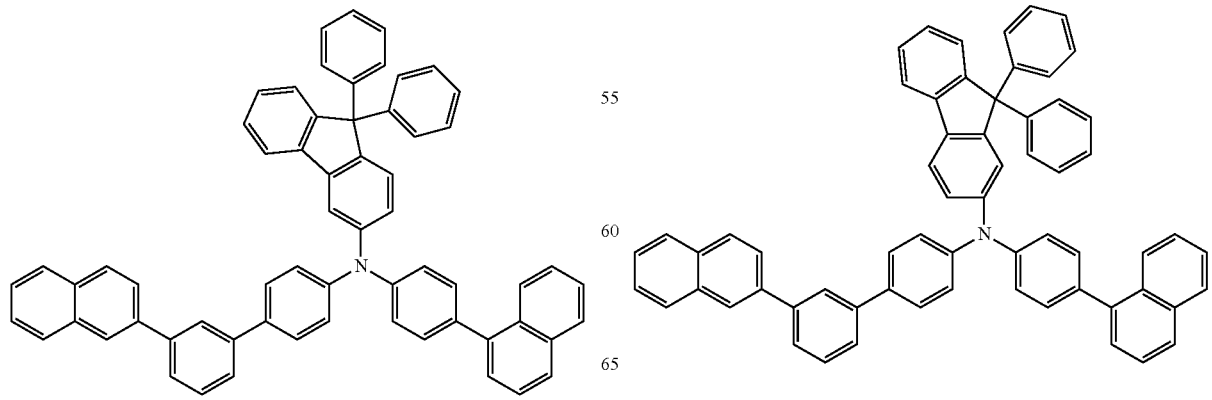

96
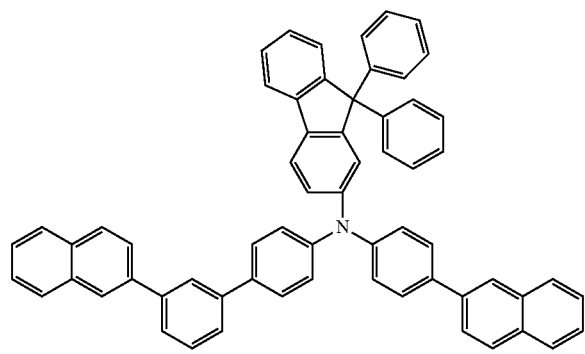
101
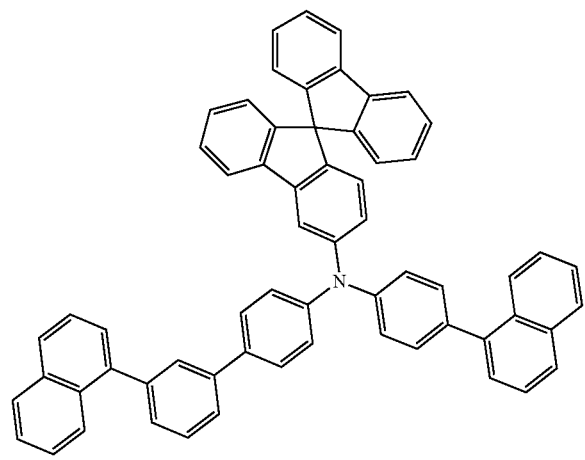
102
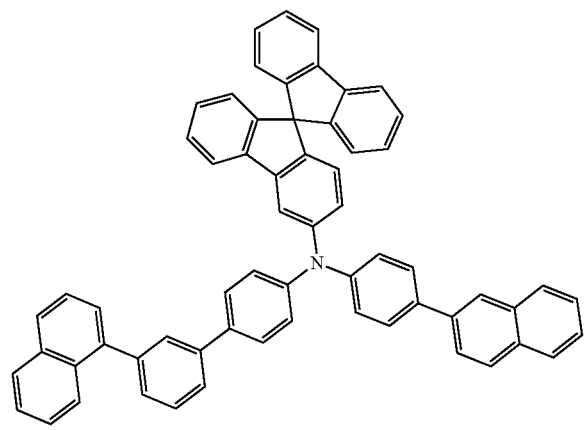
103
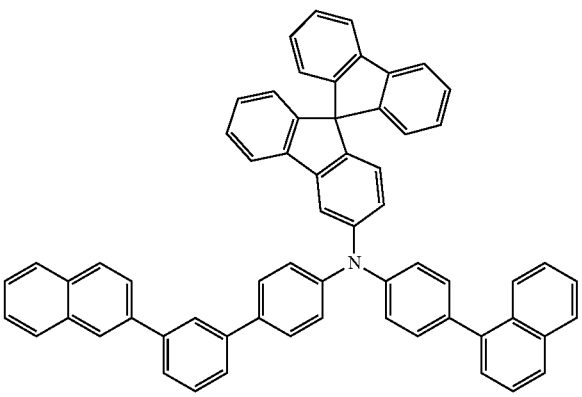
104
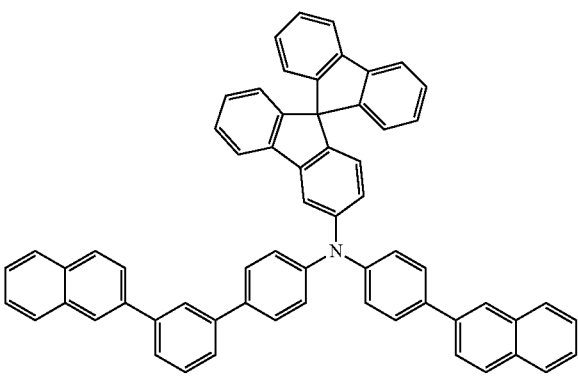
97

98
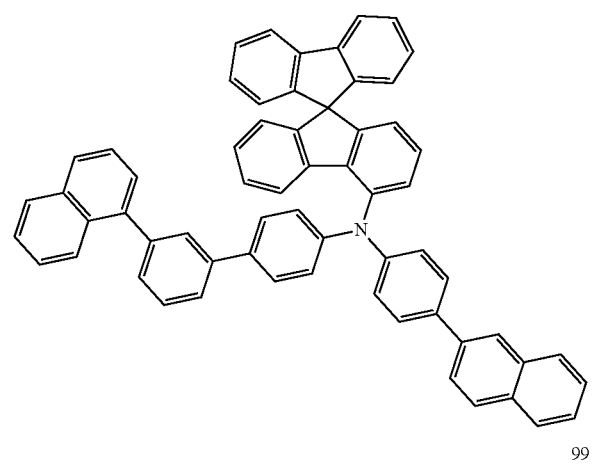
99
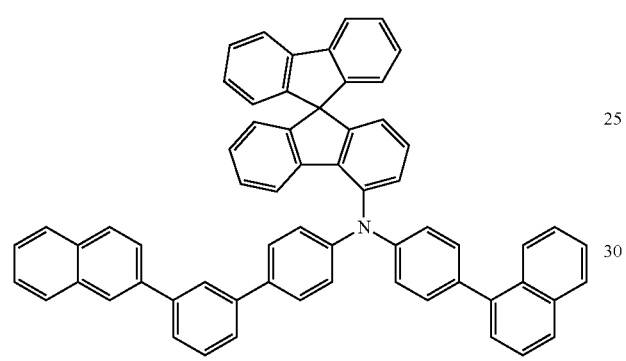
100
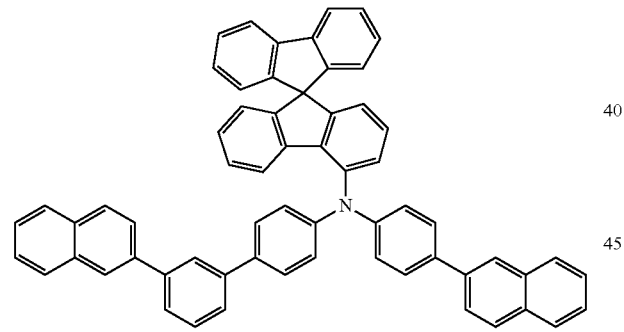
109
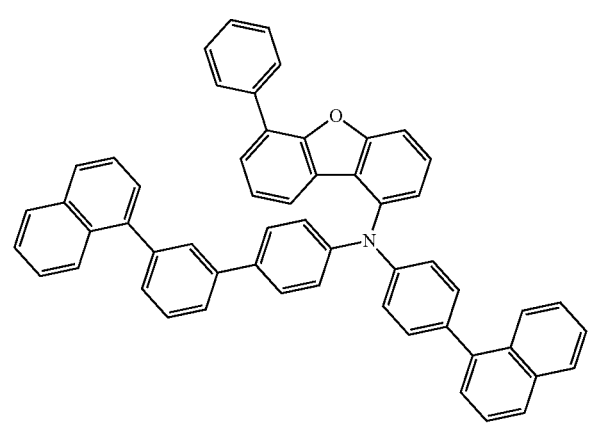
110
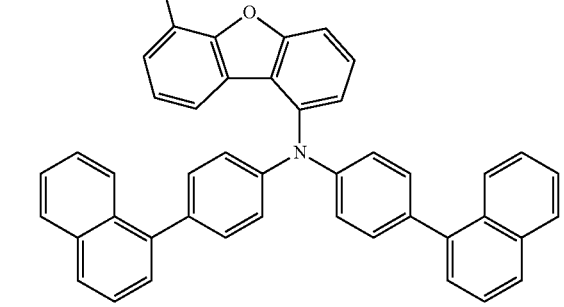
111
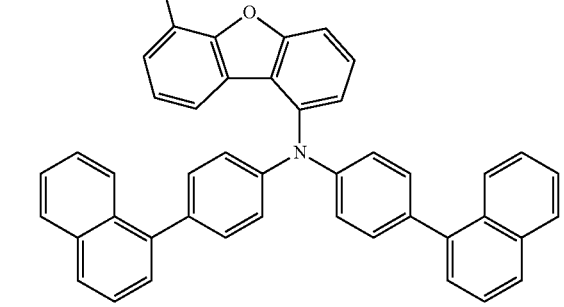
112
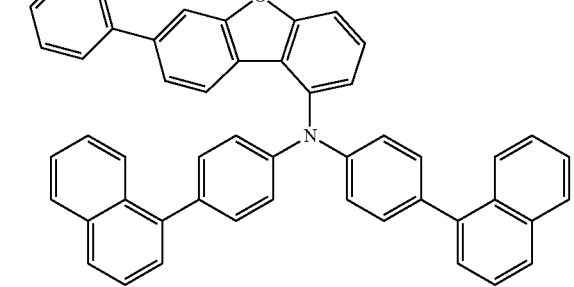
105
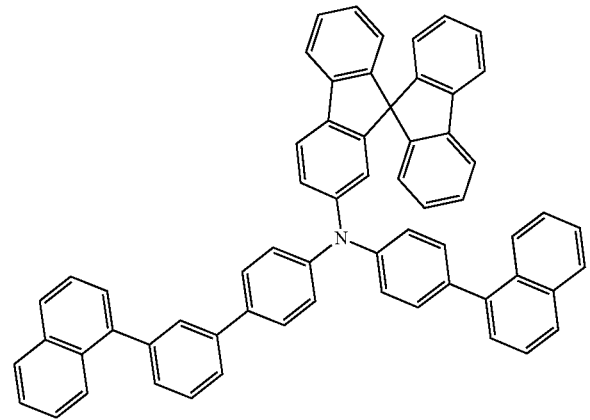

106
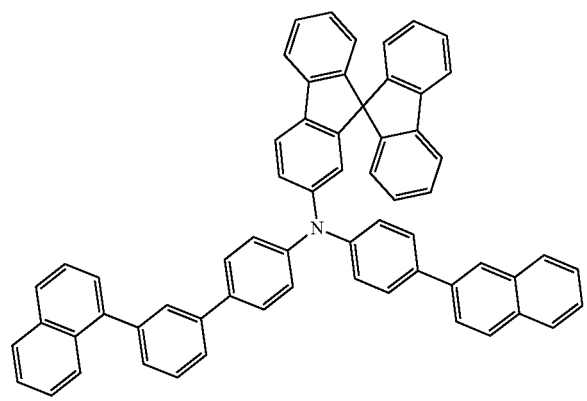
107
114
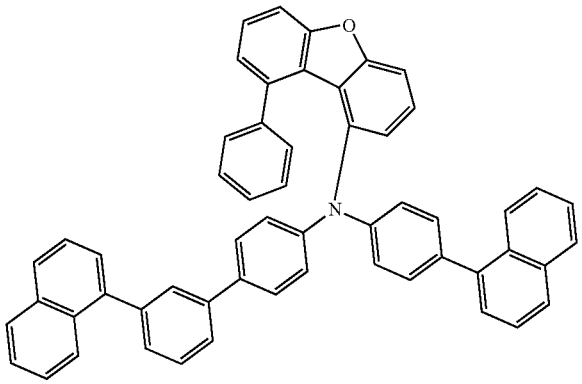
115
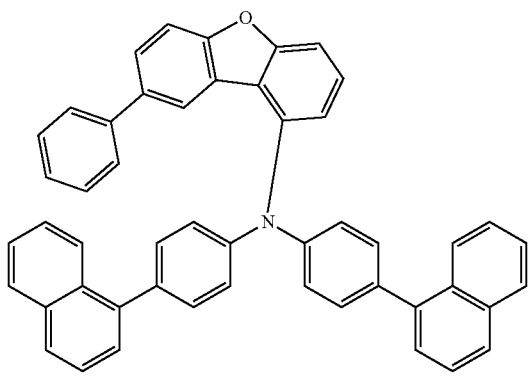
108
116
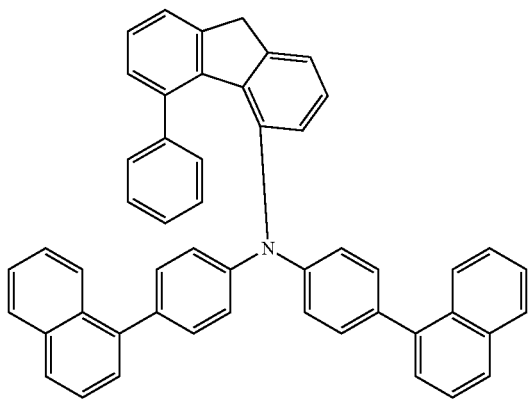
113
117
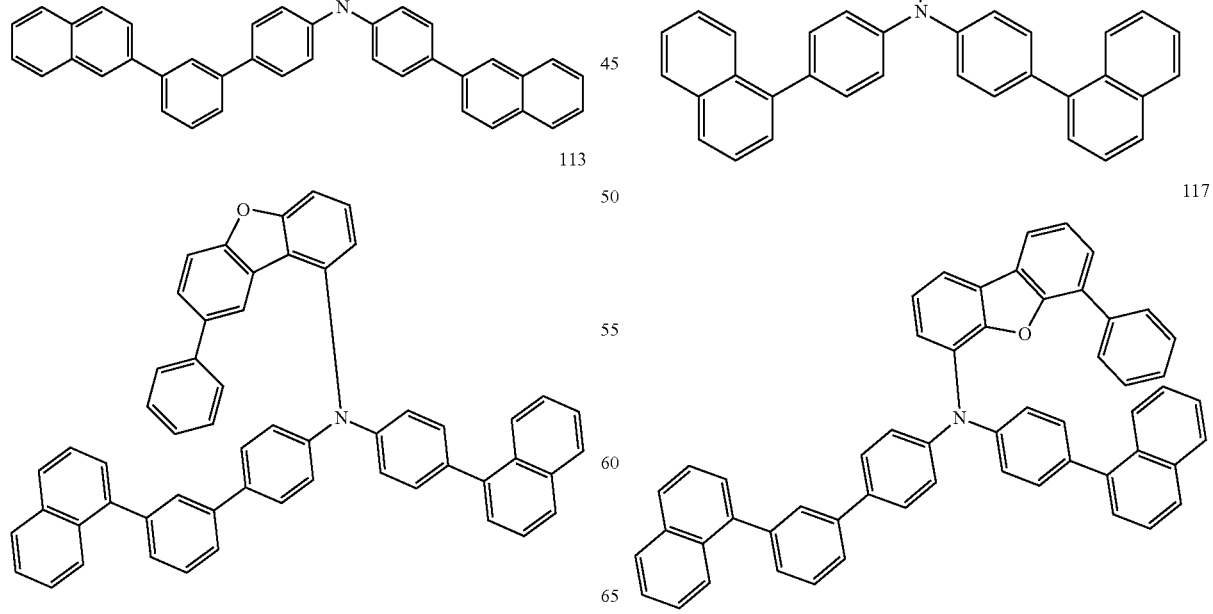

-continued

118

119

120

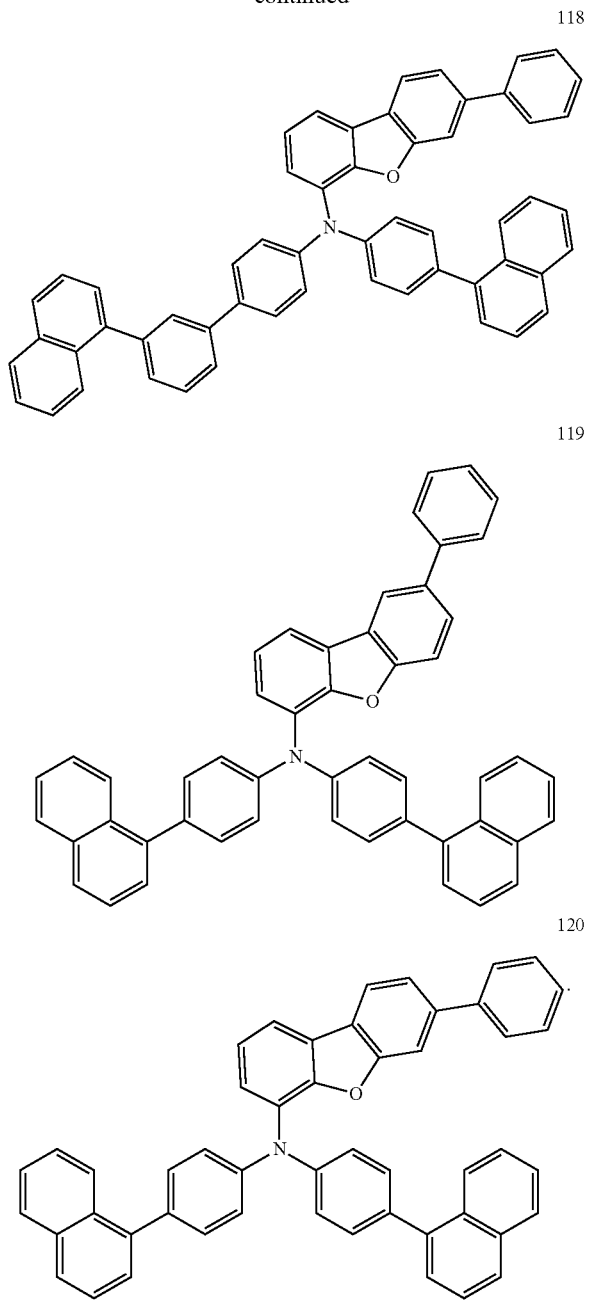

3. The organic electroluminescent device of claim 2 comprising:
an anode:
an emission layer on the anode;
an electron transport layer on the emission layer;
a cathode on the electron transport layer; and
a plurality of layers between the anode and the emission layer,
wherein the material for an organic electroluminescent device is included in at least one layer selected from the plurality of layers between the anode and the emission layer.

4. The organic electroluminescent device of claim 3, wherein the plurality of layers comprises a hole transport layer, and
wherein the material for an organic electroluminescent device is included in the hole transport layer.

5. The organic electroluminescent device of claim 4, wherein a thickness of the hole transport layer is 3 nm or more to 100 nm or less.

6. The organic electroluminescent device of claim 3, wherein the emission layer comprises an anthracene derivative and/or a pyrene derivative.

7. The organic electroluminescent device of claim 6, wherein the anthracene derivative is represented by following Formula 4:

Formula 4

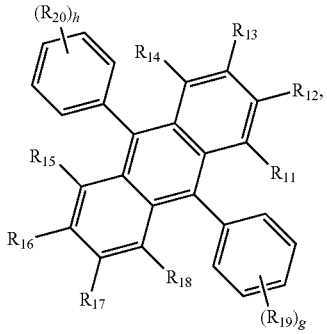

wherein, in Formula 4,
$R_{11}$ to $R_{20}$ are each independently selected from a substituted or unsubstituted aryl group having 6 to 30 ring-forming carbon atoms, a substituted or unsubstituted heteroaryl group having 1 to 30 ring-forming carbon atoms, an alkyl group having a carbon atom number of 1 to 15, a silyl group, a halogen atom, hydrogen, and deuterium, and a plurality of adjacent $R_{11}$ to $R_{20}$ optionally combine with each other to form a ring; and
g and h are each independently an integer from 0 to 5.

8. The organic electroluminescent device of claim 3, wherein the emission layer comprises a dopant material.

9. The organic electroluminescent device of claim 3, wherein the electron transport layer comprises a nitrogen-containing aromatic ring compound, a triazine derivative, an imidazole derivative, or a combination thereof.

10. The organic electroluminescent device of claim 3, wherein a thickness of the electron transport layer is 15 nm or more to 50 nm or less.

* * * * *